(12) United States Patent
Macdessi et al.

(10) Patent No.: US 12,245,819 B2
(45) Date of Patent: Mar. 11, 2025

(54) METHOD OF SURGERY

(71) Applicant: Mako Surgical Corp., Fort Lauderdale, FL (US)

(72) Inventors: Samuel John Macdessi, Haberfield (AU); Darren Chen, Woollahra (AU); William Griffiths-Jones, Devon (GB)

(73) Assignee: Mako Surgical Corp., Weston, FL (US)

( * ) Notice: Subject to any disclaimer, the term of this patent is extended or adjusted under 35 U.S.C. 154(b) by 764 days.

(21) Appl. No.: 17/278,082

(22) PCT Filed: Nov. 29, 2018

(86) PCT No.: PCT/AU2018/000241
§ 371 (c)(1),
(2) Date: Mar. 19, 2021

(87) PCT Pub. No.: WO2020/056443
PCT Pub. Date: Mar. 26, 2020

(65) Prior Publication Data
US 2021/0346036 A1    Nov. 11, 2021

(30) Foreign Application Priority Data
Sep. 19, 2018 (AU) ................................ 2018903520

(51) Int. Cl.
*A61B 34/10* (2016.01)
*A61B 5/107* (2006.01)
(Continued)

(52) U.S. Cl.
CPC ............ *A61B 34/10* (2016.02); *A61B 5/1071* (2013.01); *A61B 17/155* (2013.01);
(Continued)

(58) Field of Classification Search
CPC ................ A61B 5/1071; A61B 17/154; A61B 17/155; A61B 17/157; A61B 17/56; A61B 2017/565; A61B 2090/067; A61B 34/10
See application file for complete search history.

(56) References Cited

U.S. PATENT DOCUMENTS 4,484,975 A    11/1984 McElroy
5,682,886 A    11/1997 Delp et al.
(Continued)

FOREIGN PATENT DOCUMENTS

AU    2015320707 A1    4/2017
AU    2016267404 A1    12/2017
(Continued)

OTHER PUBLICATIONS

Abdel et al., "Coronal alignment in total knee replacement: historical review, contemporary analysis, and future direction", The Bone & Joint Journal, vol. 96-B, No. 7, Jul. 2014, pp. 857-862.
(Continued)

*Primary Examiner* — Larry E Waggle, Jr.
(74) *Attorney, Agent, or Firm* — Lerner David LLP

(57) ABSTRACT

Provided herein are methods of performing knee surgery, which include comparing a lateral distal femoral angle (LDFA) of the knee with a medial proximal tibial angle (MPTA) of the knee and determining a pre-disease alignment of the knee therefrom. Additionally, prognostic and diagnostic methods for use in knee surgery as well as methods of determining an angle of resection for a distal femur and/or a proximal tibia during knee surgery are provided herein. Also provided is an apparatus for assisting a surgeon in performing surgery on a knee of a patient, the apparatus comprising a processor configured for performing the aforementioned methods. A computer-readable medium having stored thereon a computer program, which, when
(Continued)

executed by a computer, causes the computer to perform the aforementioned methods is also provided.

22 Claims, 22 Drawing Sheets

(51) Int. Cl.
  *A61B 17/15* (2006.01)
  *A61B 17/56* (2006.01)
  *A61B 90/00* (2016.01)
(52) U.S. Cl.
  CPC ............ *A61B 17/157* (2013.01); *A61B 17/56* (2013.01); *A61B 90/06* (2016.02); *A61B 2017/565* (2013.01); *A61B 2090/067* (2016.02)

(56) References Cited

U.S. PATENT DOCUMENTS

| | | | |
|---|---|---|---|
| 5,871,018 | A | 2/1999 | Delp et al. |
| 5,995,738 | A | 11/1999 | DiGioia, III et al. |
| 7,094,241 | B2 | 8/2006 | Hodorek et al. |
| 7,787,932 | B2 | 8/2010 | Vilsmeier et al. |
| 7,842,039 | B2 | 11/2010 | Hodorek et al. |
| 8,454,616 | B2 | 6/2013 | Hodorek et al. |
| 8,611,504 | B2 | 12/2013 | Kubiak et al. |
| 8,617,171 | B2 | 12/2013 | Park et al. |
| 8,702,712 | B2 | 4/2014 | Jordan et al. |
| 9,345,548 | B2 | 5/2016 | Schoenefeld et al. |
| 9,532,845 | B1 | 1/2017 | Dossett et al. |
| 9,901,463 | B2 | 2/2018 | Mahfouz |
| 9,913,690 | B2 | 3/2018 | Grimm et al. |
| 2005/0101966 | A1 | 5/2005 | Lavallee |
| 2006/0264731 | A1 | 11/2006 | Murphy |
| 2008/0319448 | A1 | 12/2008 | Lavallee et al. |
| 2013/0166254 | A1 | 6/2013 | Grimm et al. |
| 2015/0230873 | A1 | 8/2015 | Kubiak et al. |
| 2017/0065350 | A1 | 3/2017 | Dossett et al. |
| 2017/0231552 | A1 | 8/2017 | Oosthuizen |
| 2017/0265944 | A1 | 9/2017 | Shupe et al. |
| 2018/0055655 | A1 | 3/2018 | Mahfouz |
| 2018/0235641 | A1 | 8/2018 | McAuliffe et al. |
| 2018/0255321 | A1 | 9/2018 | Hulsken |

FOREIGN PATENT DOCUMENTS

| | | |
|---|---|---|
| AU | 2016306363 A1 | 2/2018 |
| CA | 2993827 A1 | 2/2017 |
| CN | 107106239 A | 8/2017 |
| EP | 1341468 A1 | 9/2003 |
| EP | 1628590 A1 | 3/2006 |
| EP | 3197403 A1 | 8/2017 |
| EP | 3302320 A1 | 4/2018 |
| EP | 3334383 A1 | 6/2018 |
| GB | 2547427 A | 8/2017 |
| JP | 2017028264 A | 2/2017 |
| JP | 2018525201 A | 9/2018 |
| JP | 2018527835 A | 9/2018 |
| KR | 20180039646 A | 4/2018 |
| WO | 2002062249 A1 | 8/2002 |
| WO | 2004070580 A2 | 8/2004 |
| WO | 2014145540 A2 | 9/2014 |
| WO | 2016049151 A1 | 3/2016 |
| WO | 2016187668 A1 | 12/2016 |
| WO | 2017027460 A1 | 2/2017 |

OTHER PUBLICATIONS

Acorn, A.C.O.R. ACORN Annual Report, 2015. 2015 2015; Available from: <http://www.acornregistry.org/images/ACORN_AnnualReport_2015.pdf>.
Ali et al., "Dissatisfied patients after total knee arthroplasty: a registry study involving 114 patients with 8-13 years of followup", Acta Orthop, vol. 85, Issue 3, Apr. 2014, p. 229-233.
Babazadeh et al., "The long leg radiograph is a reliable method of assessing alignment when compared to computer-assisted navigation and computer tomography", The Knee, vol. 20, Issue 4, Aug. 2013, pp. 242-249.
Bellemans et al., "The Chitranjan Ranawat Award: Is Neutral Mechanical Alignment Normal for All Patients? The Concept of Constitutional Varus", Clinical Orthopaedics and Related Research, vol. 470, No. 1, Jan. 2012, pp. 45-53.
Berend et al., "The Chetranjan Ranawat Award: Tibial Component Failure Mechanisms in Total Knee Arthroplasty", Clinical Orthopaedics and Related Research, vol. 428, Nov. 2004, pp. 26-34.
Boonen B, Kerens B, Schotanus MG, Emans P, Jong B, Kort NP. Inter-observer reliability of measurements performed on digital long-leg standing radiographs and assessment of validity compared to 3D CT-scan. The Knee. 2016;23(1):20-4.
Bowman et al., "Inter-observer and intra-observer reliability of mechanical axis alignment before and after total knee arthroplasty using long leg radiographs", The Knee, vol. 23, Issue 2, Mar. 2016, pp. 203-208.
Calliess et al., "PSI kinematic versus non-PSI mechanical alignment in total knee arthroplasty: a prospective, randomized study", Knee Surgery, Sports Traumatology, Arthroscopy, vol. 25, Issue 6, Jun. 2017, pp. 1743-1748.
Chareancholvanich et al., "A prospective randomised controlled study of patient-specific cutting guides compared with conventional instrumentation in total knee replacement", The Bone & Joint Journal, vol. 95-B, No. 3, Mar. 2013, pp. 354-359.
Chauhan et al., "Computer-assisted total knee replacement. A controlled cadaver study using a multi-parameter quantitative CT assessment of alignment (the Perth CT Protocol)", The Journal Bone & Joint Surgergy, British vol. 86-B, No. 6, Aug. 2004, pp. 818-823.
Choi et al., "Patient Satisfaction after Total Knee Arthroplasty, Knee Surgery & Related Research", vol. 28, Issue 1, Mar. 2016, pp. 1-15.
Churches et al., Arthroplasty Clinical Outcomes Registry National (ACORN) Annual Report 2016, Ingham Institute for Applied Medical Research, 2017 Available from http://www.acornregistry.org/images/Acorn-Annual-Report-2016-v12.pdf.
Colebatch et al., "Effective measurement of knee alignment using AP knee radiographs", The Knee, vol. 16, Issue 1, Jan. 2009, pp. 42-45.
Cooke et al., "Frontal Plane Knee Alignment: A Call for Standardized Measurement", The Journal of Rheumatology, vol. 34, No. 9, Sep. 2007, pp. 1796-1801.
D'Lima DD, Chen PC, Colwell CW, Jr. Polyethylene contact stresses, articular congruity, and knee alignment. Clinical orthopaedics and related research. 2001(392):232-8.
Dossett et al., "A randomised controlled trial of kinematically and mechanically aligned total knee replacements: two-year clinical results", The Bone & Joint Journal, vol. 96-B, No. 7, Jul. 2014, pp. 907-913.
Dossett et al., "Kinematically versus mechanically aligned total knee arthroplasty", Orthopedics, vol. 35, No. 2, Feb. 2012, pp. e160-e169.
Dunbar et al., "I can't get no satisfaction after my total knee replacement: rhymes and reasons", The Bone & Joint Journal, vol. 95-B, Issue 11, Nov. 1, 2013, pp. 148-152.
Fanget et al., "Coronal alignment in total knee arthroplasty: just how important is it?", The Journal of Arthroplasty, vol. 24, Issue 6, Sep. 2009, pp. 39-43.
Gustke et al., "A new method for defining balance: promising short-term clinical outcomes of sensor-guided TKA", The Journal of Arthroplasty, vol. 29, May 2014, pp. 955-960.
Gustke et al., "Increased satisfaction after total knee replacement using sensor-guided technology", The Bone & Joint Journal, vol. 96-B, Issue 10, Oct. 2014, pp. 1333-1338.
Hetaimish et al., "Meta-Analysis of Navigation vs Conventional Total Knee Arthroplasty", The Journal of Arthroplasty, vol. 27, Issue 6, Jun. 2012, pp. 1177-1182.
Holme et al., "Computed tomography scanogram compared to long leg radiograph for determining axial knee alignment", Acta Orthopaedica, vol. 86, Issue 4, Jan. 2015, pp. 440-443.

(56) References Cited

OTHER PUBLICATIONS

Howell et al., "Does a kinematically aligned total knee arthroplasty restore function without failure regardless of alignment category?", Clinical Orthopaedics and Related Research, vol. 471, Issue 3, Mar. 2013, pp. 1000-1007.
Hutt et al., "Kinematic TKA using navigation: Surgical technique and initial results", Orthopaedics & Traumatology: Surgery & Research, vol. 102, Issue 1, Feb. 2016, pp. 99-104.
Insall et al., "The total condylar knee prosthesis. A report of two hundred and twenty cases", The Journal of Bone & Joint Surgery, American Volume, vol. 61, No. 2, Feb. 1979, pp. 173-180. Abstract Only Inlcuded.
International Search Report from PCT/AU2018/000241 mailed Dec. 21, 2018, 4 pages.
Jeffery et al., Coronal alignment after total knee replacement. The Journal of bone and joint surgery British volume. 1991;73(5):709-14.
Kellgrenet al., Radiological assessment of osteo-arthrosis. Ann Rheum Dis, 1957. 16(4): p. 494-502.
Keshmiri et al., The influence of component alignment on patellar kinematics in total knee arthroplasty. Acta orthopaedica. 2015;86(4):444-50.
Lee et al., "Kinematic alignment is a possible alternative to mechanical alignment in total knee arthroplasty", Knee Surg Sports Traumatol Arthrosc, vol. 25, Apr. 2017, pp. 3467-3479.
Li et al., "Polyethylene Damage Increases With Varus Implant Alignment in Posterior-stabilized and Constrained Condylar Knee Arthroplasty", Clinical Orthopaedics and Related Research, vol. 475, Issue 12, Dec. 2017, pp. 2981-2991.
Macdessi et al. "How Accurately Can Soft Tissue Balance Be Determined in Total Knee Arthroplasty?", The Journal of Arthroplasty, vol. 34, Issue, Feb. 2, 2019, pp. 290-294.e1.
Mannan et al., Favourable rotational alignment outcomes in PSI knee arthroplasty: A Level 1 systematic review and meta-analysis. The Knee. 2016;23(2):186-90.
Mason, J.B., et al., Meta-analysis of alignment outcomes in computer-assisted total knee arthroplasty surgery. J Arthroplasty, 2007. 22(8): p. 1097-106.
Meneghini et al., "Can Intraoperative Sensors Determine the "Target" Ligament Balance? Early Outcomes in Total Knee Arthroplasty", The Journal of Arthroplasty, vol. 31, Issue 10, Oct. 2016 pp. 2181-2187.
Nam et al., "Patient dissatisfaction following total knee replacement: a growing concern?", The Bone & Joint Journal, vol. 96-B, No. 11 Supple A, Nov. 1, 2014, pp. 96-100.
Paley et al., [Principles of deformity correction around the knee]. Orthopade. 2000;29(1):18-38.
Paley, D., "Principles of Deformity Correction", 2003, Heidelberg, Germany, Springer-Verlag.
Park et al., "The Inadequacy of Short Knee Radiographs in Evaluating Coronal Alignment After Total Knee Arthroplasty", The Journal of Arthroplasty, vol. 31, Issue 4, Apr. 2016, pp. 878-882.
Parratte et al., "Effect of postoperative mechanical axis alignment on the fifteen-year survival of modern, cemented total knee replacements", The Journal Bone & Joint Surgery, Sep. 2010, vol. 92, Issue 12, pp. 2143-2149.
Raju et al., Wear patterns of tibiofemoral articulation in osteoarthritic knees: analysis and review of literature. Archives of orthopaedic and trauma surgery. 2012;132(9):1267-71.
Ritter et al., "Postoperative alignment of total knee replacement. Its effect on survival", Clinical Orthopaedics and Related Research, vol. 299, Jan. 1994, pp. 153-156. Abstract Only Included.

Sakellariou et al., "Risk Assessment for Chronic Pain and Patient Satisfaction After Total Knee Arthroplasty", Orthopedics, vol. 39, Issue 1, Jan. 2016, pp. 55-62. Abstract Included Only.
Schnaser et al., "The Position of the Patella and Extensor Mechanism Affects Intraoperative Compartmental Loads During Total Knee Arthroplasty: A Pilot Study Using Intraoperative Sensing to Guide Soft Tissue Balance", The Journal of Arthroplasty, vol. 30 Issue 8, Aug. 2015, pp. 1348-1353 e3.
Schulze et al., "[Satisfaction after total knee arthroplasty. Comparison of 1990-1999 with 2000-2012]", Der Orthopade, vol. 42, No. 10, Sep. 30, 2013, pp. 858-865. Abstract Included Only.
Scott et al., "Predicting dissatisfaction following total knee arthroplasty in patients under 55 years of age", The Bone & Joint Journal, vol. 98-B, No. 12, Dec. 2016, pp. 1625-1634.
Shelton et al., Do varus or valgus outliers have higher forces in the medial or lateral compartments than those which are in-range after a kinematically aligned total knee arthroplasty? limb and joint line alignment after kinematically aligned total knee arthroplasty. The bone & joint journal. 2017;99-b(10):1319-28.
Sikorski, J.M., "Alignment in total knee replacement", The Journal of Bone & Joint Surgery, British vol. 90-B, No. 9, Sep. 2008, pp. 1121-1127.
Slevin et al., Coronal femoral TKA position significantly influences in vivo patellar loading in unresurfaced patellae after primary total knee arthroplasty. Knee surgery, sports traumatology, arthroscopy : official journal of the ESSKA. 2017;25(11):3605-10.
Stronach et al., "Patient-specific total knee arthroplasty required frequent surgeon-directed changes", Clinical Orthopaedics and Related Research, vol. 471, Issue 1, Jan. 2013, pp. 169-174.
Thienpont et al. "Efficacy of Patient-Specific Instruments in Total Knee Arthroplasty: A Systematic Review and Meta-Analysis", Journal Bone & Joint Surgery, vol. 99, Issue 6, Mar. 2017, pp. 521-530.
Thienpont et al., A systematic review and meta-analysis of patient-specific instrumentation for improving alignment of the components in total knee replacement. The bone & joint journal. 2014;96-b(8):1052-61.
Victor et al., "Patient-specific guides do not improve accuracy in total knee arthroplasty: a prospective randomized controlled trial", Clinical Orthopaedics and Related Research, vol. 472, Issue 1, Jan. 2014, pp. 263-271.
Waterson et al., "The early outcome of kinematic versus mechanical alignment in total knee arthroplasty: a prospective randomised control trial", The Bone & Joint Journal, vol. 98-B, No. 10, Oct. 2016, pp. 1360-1368.
Werner et al., Rullkoetter PJ. The effect of valgus/varus malalignment on load distribution in total knee replacements. Journal of biomechanics. 2005;38(2):349-55.
Williams et al., "Early postoperative predictors of satisfaction following total knee arthroplasty", The Knee, vol. 20, Issue 6, Dec. 2013, pp. 442-446.
Young et al., "The Chitranjan S. Ranawat Award : No. Difference in 2-year Functional Outcomes Using Kinematic versus Mechanical Alignment in TKA: A Randomized Controlled Clinical Trial", Clin Orthop Relat Res, vol. 33, Issue 10, Supplement, Oct. 2017, p. e115.
Zhang et al. Alignment of the lower extremity mechanical axis by computer-aided design and application in total knee arthroplasty. International journal of computer assisted radiology and surgery. 2016;11(10):1881-90.
Krackow Kenneth A: "The Measurement and Analysis of Axial Deformity at the Knee", The Homer Stryker Center, Jan. 1, 2008, pp. 1-58, XP055851059, Retrieved from the Internet: URL:https://www.medschool.lsuhsc.edu/ortho/docs/ How%20to%20Measure%20Knee%20Alignment.pdf [retrieved on Oct. 13, 2021].

Arithmetic HKA = MPTA − LDFA

METHOD OF SURGERY

CROSS-REFERENCE TO RELATED APPLICATIONS

The present application is a national phase entry under 35 U.S.C. § 371 of International Application No. PCT/AU2018/000241 filed Nov. 29, 2018, published in English, which claims priority from Australian Provisional Application No. AU 2018903520 filed Sep. 19, 2018, all of which are incorporated herein by reference.

FIELD

THIS INVENTION described herein relates generally to a method of surgery. In particular, the invention is directed to a method of knee surgery and, in particular, total knee replacement that achieves pre-disease alignment of the knee for optimal soft tissue balancing and appropriate joint line restoration.

BACKGROUND

Total knee arthroplasty (TKA) or total knee replacement (TKR) is a surgical technique in which a surgical implant is inserted to replace the knee joint. Typically, TKA/TKR is a successful and long lasting surgical procedure but 10-20% of patients express some dissatisfaction regarding the outcome of the procedure or suffer from persistent pain. The skilled artisan would recognize that to achieve a good clinical outcome with TKR, correct implant sizing and alignment, optimal soft tissue balancing, equal flexion and extension gaps and joint line restoration are required.

The standard technique in knee arthroplasty is to cut the tibia and femur perpendicular to the mechanical axis of the limb and parallel to the floor, creating a rectangular extension gap. The external rotation of the femoral component compensates for the loss of an assumed 3 degrees of tibial varus and produces a rectangular flexion gap. This long-established gold standard technique has remained largely unchanged for the last 30 years and is thought to provide the best mechanical environment for the longevity of the prosthesis. During this time, there has been a steady evolution of prosthesis design and the survivorship of the implants has improved significantly. Latest registry data suggests an <10% revision rate at 20 years. Over the same period the patient reported outcomes have not benefited from the same improvements, as noted above.

These improvements in implant survivorship in TKA and the corresponding lack of progress in outcomes has led some to suggest a shift in technique favoring recreation of the patients own anatomy at the expense of the ideal mechanical environment for the prosthesis. This was first described as kinematic alignment by Howell et al. Notwithstanding this, the distribution of lower limb alignment in the asymptomatic population is very different from the deformity present in patients that require total knee arthroplasty (TKA) (Bellemans et al., 2012). Progressive joint space loss during the disease process leads to exaggeration of the hip knee ankle (HKA) angle with a broader spread of deformity in this population.

Accordingly, many patient specific mapping systems use proprietary algorithms, the details of which are often not clear to the surgeon, and most require costly and otherwise non-clinically indicated 3D imaging (Young et al., 2017; Waterson et al., 2016; Dossett et al., 2012; Calliess et al., 2017). With the rise in prominence of kinematic techniques in TKA that aim to restore this constitutional alignment, accurate and relatively straightforward techniques to estimate this pre-disease alignment are required.

SUMMARY

The present invention is broadly directed to a method of performing knee surgery and, in particular, TKR. The method may be performed prior to resection of the knee bones for precise kinematic or constitutional realignment of the hip-knee-ankle angle (HKA) by way of coupling measurement of the lateral distal femoral angle (LDFA) and the medial proximal tibial angle (MPTA). The invention is further directed to prognostic and diagnostic methods for use in knee surgery as well as methods of determining an angle of resection for a distal femur and/or proximal tibia during knee surgery.

In a first aspect, the invention is directed to a method of performing surgery on a knee of a patient, including the steps of:

(a) comparing a lateral distal femoral angle (LDFA) of the knee with a medial proximal tibial angle (MPTA) of the knee; and (b) determining a pre-disease alignment of a femur and/or a tibia of the knee based at least partly on the comparison in (a).

Suitably, the method of the present aspect further includes the initial step of determining the LDFA and/or the MPTA from an image of the knee. Preferably, the step of determining the LDFA includes determining:

(a) a first alignment axis from one or a plurality of first anatomical indicators; and (b) a femoral joint line from one or a plurality of second anatomical indicators; on the image of the knee.

In particular embodiments, the first alignment axis is or comprises a femoral mechanical axis. In this regard, the one or a plurality of first anatomical indicators are suitably selected from the group consisting of a central portion of a femoral head, a central portion of a proximal femoral shaft, an intramedullary canal insertion point, a deepest portion of a trochlear groove and a central portion of an intercondylar notch.

In one embodiment, the one or plurality of second anatomical indicators are selected from the group consisting of a distal portion of a medial condyle and a distal portion of a lateral condyle.

Suitably, the step of determining the MPTA includes determining:

(a) a second alignment axis from one or a plurality of third anatomical indicators; and (b) a tibial joint line from one or a plurality of fourth anatomical indicators; on the image of the knee.

In a preferred embodiment, the second alignment axis is or comprises a tibial mechanical axis. With respect to such embodiments, the one or a plurality of third anatomical indicators are suitably selected from the group consisting of a central portion of a line extending between medial and lateral tibial spines, a central portion of a talus, a central portion of a distal tibial shaft and an anterior cruciate ligament tibial attachment point.

In one embodiment, the one or plurality of fourth anatomical indicators are selected from the group consisting of a proximal portion of a medial tibial plateau, a proximal portion of a lateral tibial plateau, a central portion of a lateral meniscus and a central portion of a medial meniscus.

Suitably, step (a) of the present method comprises subtracting the LDFA from the MPTA to define a pre-disease hip-knee-ankle angle (HKA). Preferably, the method of the current aspect further includes the step of classifying the pre-disease alignment of the knee based at least in part on the pre-disease HKA. More preferably, the pre-disease alignment is classified as:
  (a) valgus if the pre-disease HKA is positive in value;
  (b) varus if the pre-disease HKA is negative in value; or
  (c) neutral if the pre-disease HKA is substantially zero.

Suitably, step (a) of the present method comprises adding the LDFA and the MPTA to define a pre-disease joint line obliquity value. Preferably, the method of the current aspect further includes the step of classifying a pre-disease joint line of the knee based at least in part on the pre-disease joint line obliquity value. More preferably, the pre-disease joint line is classified as:
  (a) an apex distal joint line if the pre-disease joint line obliquity value is less than 180°;
  (b) an apex proximal joint line if the pre-disease joint line obliquity value is greater than 180°; or
  (c) a neutral joint line if the pre-disease joint line obliquity value is substantially equal to 180°.

The method of present aspect suitably further includes the step of determining a distal resection plane of the femur and/or a proximal resection plane of the tibia from at least partly the pre-disease HKA and/or the pre-disease joint line obliquity value.

In related embodiments, the present method further includes the step of performing:
  (a) a distal femoral resection based at least partly on the distal resection plane; and/or
  (b) a proximal tibial resection based at least partly on the proximal resection plane.

In a second aspect, the invention provides a method of determining a pre-disease alignment of a femur and/or a tibia of a knee, including the step of:
  (a) comparing a lateral distal femoral angle (LDFA) of the knee with a medial proximal tibial angle (MPTA) of the knee;
  wherein the pre-disease alignment of the knee is determined based at least partly on the comparison in (a).

In a third aspect, the invention provides a method of determining a prognosis for a patient with knee disease, including the steps of:
  (a) comparing a lateral distal femoral angle (LDFA) of the knee with a medial proximal tibial angle (MPTA) of the knee;
  (b) determining a pre-disease alignment of the femur and/or the tibia of the knee based at least partly on the comparison in (a),
  wherein the pre-disease alignment indicates or correlates with the prognosis for the patient.

In a fourth aspect, a method of determining a resection plane of a femur and/or a tibia of a knee, including the steps of:
  (a) comparing a lateral distal femoral angle (LDFA) of the knee with a medial proximal tibial angle (MPTA) of the knee; and
  (b) determining a pre-disease alignment of the femur and/or the tibia of the knee based at least partly on the comparison in (a);
  to thereby determine the resection plane.

The method of second, third and fourth aspects suitably further includes the initial step of determining the LDFA and/or the MPTA from a image of the knee. Preferably, the step of determining the LDFA includes determining:
  (a) a first alignment axis from one or a plurality of first anatomical indicators; and
  (b) a femoral joint line from one or a plurality of second anatomical indicators; on the image of the knee.

With respect to the aforementioned aspects, the methods suitably further include the initial step of obtaining the image of the knee. In one preferred embodiment, the image is or comprises a long leg radiograph.

For the three aforementioned aspects, the first alignment axis suitably is or comprises a femoral mechanical axis. Preferably, the one or a plurality of first anatomical indicators are selected from the group consisting of a central portion of a femoral head, a central portion of a proximal femoral shaft, an intramedullary canal insertion point, a deepest portion of a trochlear groove and a central portion of an intercondylar notch. In particular embodiments, the one or plurality of second anatomical indicators are selected from the group consisting of a distal portion of a medial condyle and a distal portion of a lateral condyle.

Referring to the second, third and fourth aspects, the step of determining the MPTA suitably includes determining:
  (a) a second alignment axis from one or a plurality of third anatomical indicators; and
  (b) a tibial joint line from one or a plurality of fourth anatomical indicators; on the image of the knee.

For the three aforementioned aspects, the second alignment axis suitably is or comprises a tibial mechanical axis. Preferably, the one or a plurality of third anatomical indicators are selected from the group consisting of a central portion of a line extending between medial and lateral tibial spines, a central portion of a talus, a central portion of a distal tibial shaft and an anterior cruciate ligament tibial attachment point. In related embodiments, the one or plurality of fourth anatomical indicators are selected from the group consisting of a proximal portion of a medial tibial plateau, a proximal portion of a lateral tibial plateau, a central portion of a lateral meniscus and a central portion of a medial meniscus.

Suitably, in regards to the method of the second, third and fourth aspects, step (a) comprises subtracting the LDFA from the MPTA to define a pre-disease hip-knee-ankle angle (HKA). Preferably, the present method further includes the step of classifying the pre-disease alignment of the knee based at least in part on the pre-disease HKA. More preferably, the pre-disease alignment is classified as:
  (a) valgus if the pre-disease HKA is positive in value;
  (b) varus if the pre-disease HKA is negative in value; or
  (c) neutral if the pre-disease HKA is substantially zero.

In particular embodiments of the three aforementioned aspects, step (a) comprises adding the LDFA and the MPTA to define a pre-disease joint line obliquity value. Preferably, the present methods further include the step of classifying a pre-disease joint line of the knee based at least in part on the pre-disease joint line obliquity value. More preferably, the pre-disease joint line is classified as:
  (a) an apex distal joint line if the pre-disease joint line obliquity value is less than 180°;
  (b) an apex proximal joint line if the pre-disease joint line obliquity value is greater than 180°; or
  (c) a neutral joint line if the pre-disease joint line obliquity value is substantially equal to 180°.

Suitably, the methods of the above three aspects further include the step of determining the resection plane of the femur and/or tibia from at least partly the pre-disease HKA and/or the pre-disease joint line obliquity value. In particular embodiments, the resection plane is one or more of a proximal tibial resection plane, a distal femoral resection plane, a posterior femoral resection plane and/or an anterior femoral resection plane.

For the aforementioned aspects, the pre-disease alignment suitably facilitates soft tissue balancing of the knee.

In a fifth aspect, the invention provides an apparatus for assisting a surgeon in performing surgery on a knee of a patient, the apparatus comprising a processor configured for comparing a lateral distal femoral angle (LDFA) of the knee with a medial proximal tibial angle (MPTA) of the knee and determining a pre-disease alignment of the femur and/or the tibia of the knee based at least partly on the comparison.

Suitably, the apparatus is for use in the method of the first, second, third and fourth aspects.

In a sixth aspect, the invention provides a computer-readable medium having stored thereon a computer program, which, when executed by a computer, causes the computer to perform the method of the first, second, third and fourth aspects.

It will be appreciated that the indefinite articles "a" and "an" are not to be read as singular indefinite articles or as otherwise excluding more than one or more than a single subject to which the indefinite article refers.

As used herein, unless the context requires otherwise, the words "comprise", "comprises" and "comprising" will be understood to mean the inclusion of a stated integer or group of integers but not the exclusion of any other non-stated integer or group of integers.

BRIEF DESCRIPTION OF THE DRAWINGS

In order that the present invention may be readily understood and put into practical effect, reference will now be made to the accompanying illustrations.

DETAILED DESCRIPTION

Figure 1:
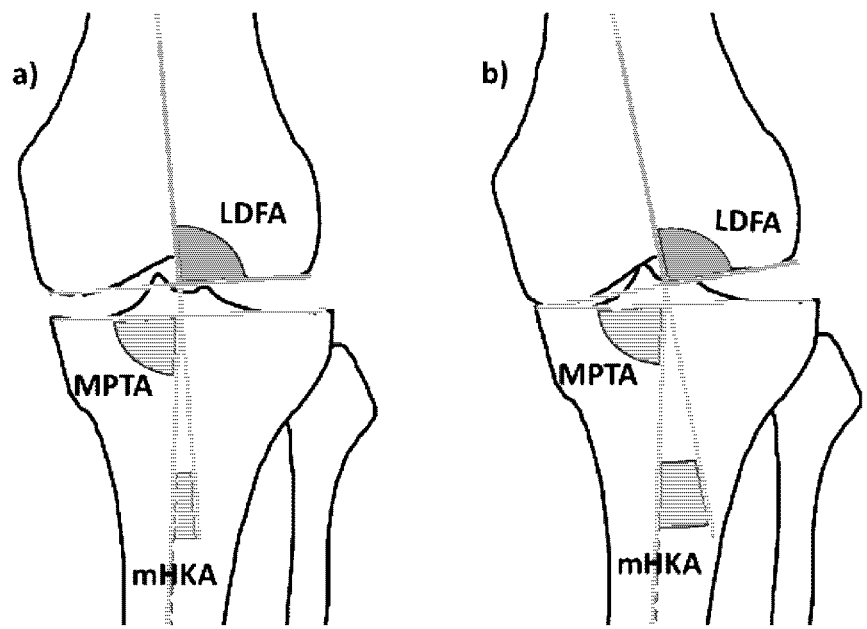
FIG. 1: a) Diagram demonstrating the LDFA, MPTA and mHKA in a knee with preserved joint space and mild varus alignment. b) Diagram of the same knee following degenerative loss of medial joint space, showing a change in mHKA and no change to LDFA and MPTA.

The present invention relates to a method of knee surgery and, in particular, TKR/TKA, that includes assessing the lateral distal femoral angle (LDFA) and the medial proximal tibial angle (MPTA) of a patient's knee so as to achieve an appropriate constitutional or kinematic alignment of the HKA prior to one or more bone resections being mapped or performed. The invention is further directed to prognostic and diagnostic methods for use in knee surgery as well as methods of determining an angle of resection for a distal femur and/or proximal tibia during knee surgery.

While the principles described herein are based on methods of knee surgery for humans, this invention may also be extended to other mammals such as livestock (e.g. cattle, sheep), performance animals (e.g. racehorses) and domestic pets (e.g. dogs, cats), although without limitation thereto.

In one aspect, the invention resides in a method of performing surgery on a knee of a patient, including the steps of:
(a) comparing a lateral distal femoral angle (LDFA) of the knee with a medial proximal tibial angle (MPTA) of the knee;
(b) determining a pre-disease alignment of a femur and/or a tibia of the knee based at least partly on the comparison in (a).

As generally used herein, the term "lateral distal femoral angle" refers to an angle formed from the intersection of a mechanical axis and a knee joint line or articular surface of a distal femur. The LDFA can also be expressed in degrees of valgus (or varus) from a 90 degree angle relative to the mechanical axis (e.g., 1.8 degrees valgus), and can then also be referred to as the femoral joint angle. The LDFA generally has a normal value of 88° (range 85°-90°; e.g., 85, 85.5, 86, 86.5, 87, 87.5, 88, 88.5, 89, 89.5, 90 degrees and any range therein).

By "medial proximal tibial angle" is meant an angle between a mechanical axis and a knee joint line or articular surface of a proximal tibia. The MPTA generally has a normal value of 87° (range 85°-90°; e.g., 85, 85.5, 86, 86.5, 87, 87.5, 88, 88.5, 89, 89.5, 90 degrees and any range therein).

The term "pre-disease alignment" refers to that alignment of a knee joint, particularly in respect of a coronal alignment of the knee joint, prior to the onset of a disease in the patient's knee. To this end, it will be appreciated that implant planning in knee surgery can be complicated when the knee joint is subject to a disease state, such as osteoarthritis, that causes defects (e.g., osteophytes, capsular adhesions, osteochondral defects (OCD), and the like) that prevent the bones of the limb from achieving a desired alignment, such as a neutral alignment. For example, when a person with a healthy knee joint is in a standing position and the joint bears weight, the femur and tibia are typically neutrally aligned such that the centre of the femoral head (i.e., the hip centre), the centre of the knee joint (i.e., the knee centre), and the centre of the ankle joint (i.e., the ankle centre) are in line. This results in a neutral leg alignment (i.e., a neutral limb pose) in which the position and/or orientation of the femur and/or the tibia result in both the medial and lateral femoral condyles articulating with the tibial articular surface. In contrast, when a person has disease in one or more compartments of the knee joint (e.g., medial and/or lateral), the diseased compartment may collapse, causing the limb to adopt a non-neutral or misaligned pose.

Accordingly, a primary goal of implant planning is to determine a placement of implant components that will sufficiently correct the pre-existing disease state such that proper or appropriate joint kinematics are restored. Appropriate joint kinematics can vary from person to person based on the unique anatomy of each individual. For example, appropriate joint kinematics may be achieved by planning the implant components such that, after the implants are installed, the limb is in an appropriate or desired pre-disease alignment (e.g., alignment of the femur and/or tibia is restored to its pre-disease state). In particular embodiments, the pre-disease alignment is or comprises a neutral alignment or a near neutral alignment for the patient in question As such, the invention provides, in part, a method that can be utilized for determining a pre-disease or constitutional alignment of a lower limb and knee joint when, for example, degenerative arthritis or other degenerative joint disease is present therein. This constitutional or pre-disease alignment can then be used to determine one or more resection planes to be applied during knee surgery for appropriate implant planning. This method may generally be performed using patient-specific anatomical information or data obtained from a patient-specific image or representation of their knee joint (or lower limb) in extension. It will be appreciated, however, that one or both of, for example, LDFA and MPTA, as well as further anatomical information from a patient can be assessed or determined from a patient's knee in flexion or indeed throughout its entire range of motion.

In certain embodiments, the pre-disease alignment is configured so as to facilitate, at least partly, return of the knee to an appropriate and/or balanced soft tissue tension when in extension and/or flexion. Balanced soft tissue tension requires placing the soft tissues surrounding and/or interconnecting the bones of the knee, such as that of the medial and lateral knee, at an approximately equal or similar tension relative to one another when the femur and its corresponding tibia are placed in a desired pre-disease alignment as determined by the surgeon. Preferably, an appropriate soft tissue tension is approximately equal or similar to the physiological tension of these soft tissues in the native knee at rest. In this regard, a patient's soft tissue tension may be compared to that of a control or reference sample or population. Non-limiting examples of the soft tissues surrounding and/or interconnecting the bones of the knee include the medial and lateral collateral ligaments, the anterior and posterior cruciate ligaments, the posteromedial and posterolateral ligamentous structures and the posterior capsule. It will be appreciated that the present invention is not to be limited to any particular means of measuring soft tissue tension of the knee, which may include, for example, an arthrometer, a dynamometer, radiography, MRI, computer assisted surgery and a knee joint tension meter.

The term "determining" includes any form of measurement, and includes determining if an element is present or not. As used herein, the terms "determining", "measuring", "evaluating", "assessing" and "assaying" are used interchangeably and include quantitative and qualitative determinations. Determining may be relative or absolute.

Preferably, the patient-specific anatomical data of the knee is obtained when the limb is in full extension (i.e., approximately 180 degrees). The skilled artisan, however, would appreciate that this may not be possible or feasible in all patients, owing, for example, to the presence of pre-existing disease or deformities of the limb. By way of example, a patient with a flexion deformity or contracture of the knee may be physically unable to fully straighten or extend the knee. Accordingly, in certain embodiments, the anatomical data of the limb is obtained when the limb is not fully extended.

In particular embodiments, the method of the present aspect further includes the initial step of determining the LDFA and/or the MPTA from a patient-specific image of the knee. Suitably, a patient-specific image, and hence patient-specific anatomical data, is obtained pre-operatively using one or more non-invasive imaging modalities, such as radiological imaging, computerised tomography (CT)/computerised axial tomography (CAT), magnetic resonance imaging (MRI), inclusive of full limb MRI, ultrasound and/or other conventional means. The patient-specific anatomical data obtained therefrom may then be pre-processed and/or converted to form a patient-specific model or image of the knee joint. Such a patient-specific model may include a two-dimensional model (e.g., radiographs, 2D slices of MRI) and/or a three dimensional model (e.g., a three-dimensional (3D) computer aided design (CAD) model). Preferably, the patient-specific anatomical data, including LDFA and MPTA is determined or measured from a radiograph or radiological image. Even more preferably, the patient-specific image is or comprises a long leg radiograph.

In particular embodiments, the method of the present aspect further includes the step of obtaining a scan or image, such as a radiograph, of a patient's limb. This may include, for example, a full scan or image of a patient's limb. For economical or efficiency purposes, however, one or more partial scans of a patient's limb may be used rather than a full limb scan. In this regard, the exact location of each partial scan relative to a patient's limb may be carefully noted to ensure that the scans are spaced apart in all directions correctly before determining one or more of the indicators and/or axes (e.g., a tibial mechanical axis, a femoral mechanical axis) provided herein. Furthermore, one or more partial scans may be utilised when a particular landmark, such as the true femoral head centre or a midline of the tibial spines, cannot be determined and/or has been compromised due to trauma or gross deformation.

Suitably, the patient-specific image and the patient-specific anatomical data derived therefrom is used to determine a LDFA and/or a MPTA from one or a plurality of anatomical indicators of a patient's knee prior to determining a constitutional or pre-disease HKA for said patient. In this regard, a proximal portion and a distal portion of a patient's limb are typically identified. The patient's first alignment axis may then be determined by projecting and extending an imaginary line between the identified proximal and distal portions. Further, it would be appreciated that additional anatomical indicators therebetween may be used in determining the first alignment axis of a patient's limb and the relationship between the overall axis and the intercalated segments thereof (e.g., the femoral and tibial mechanical axes).

The step of determining the LDFA suitably includes determining:
 (a) a first alignment axis from one or a plurality of first anatomical indicators; and
 (b) a femoral joint line from one or a plurality of second anatomical indicators; on the patient-specific image of the knee. Preferably, the first alignment axis is or comprises a femoral mechanical axis or an axis substantially parallel thereto. It will be understood that a femoral mechanical axis typically refers to a line that extends from a centre of a femoral head to a centre of an intercondylar notch of a distal femur as assessed in a frontal or coronal plane.

It will be appreciated that the femoral mechanical axis and/or the femoral joint line can be determined by any method or anatomical indicator/s known in the art. In particular embodiments, however, the one or a plurality of first anatomical indicators are selected from the group consisting of a central portion of a femoral head, a central portion of a proximal femoral shaft, an intramedullary canal insertion point, a deepest portion of a trochlear groove and a central portion of an intercondylar notch. Further to this, the one or plurality of second anatomical indicators are suitably selected from the group consisting of a distal portion of a medial condyle and a distal portion of a lateral condyle.

It will be apparent to the skilled artisan that the femoral joint line is generally at an angle of about 85 degrees to about 95 degrees relative to the first alignment axis of the femur. In particular embodiments, the femoral joint line is at an angle of about 85, 86, 87, 88, 89, 90, 91, 92, 93, 94, 95 degrees or any range therein, relative to the first alignment axis of the femur. In particular embodiments, the femoral joint line is substantially perpendicular (i.e., about 90 degrees relative) to the first alignment axis of the femur.

The step of determining the MPTA suitably includes determining:
 (a) a second alignment axis from one or a plurality of third anatomical indicators; and
 (b) a tibial joint line from one or a plurality of fourth anatomical indicators; on the patient-specific image of the knee. Preferably, the second alignment axis is or comprises a tibial mechanical axis or an axis substantially parallel thereto. As used herein, a tibial mechanical axis generally refers to a line from a centre of a tibial plateau to a centre of a talus, although it will be understood that the tibial mechanical axis and/or the tibial joint line can be determined by any method or anatomical indicator/s as are known in the art.

In some embodiments, the one or a plurality of third anatomical indicators are selected from the group consisting of a central portion of a line extending between medial and lateral tibial spines, a central portion of a talus, a central portion of a distal tibial shaft and an anterior cruciate ligament tibial attachment point. By way of example, the central portion of the line extending between the medial and lateral tibial spines or intercondylar eminence can be determined, at least in part, by a line extending between a lateral intercondylar tubercle and a medial intercondylar tubercle. Accordingly, the central portion of the medial and lateral tibial spines may be the midpoint of this line extending between the two intercondylar tubercles.

Additionally, the one or plurality of fourth anatomical indicators are suitably selected from the group consisting of a proximal portion of a medial tibial plateau, a proximal portion of a lateral tibial plateau, a central portion of a lateral meniscus and a central portion of a medial meniscus.

Again, it will be appreciated that the tibial joint line is generally at an angle of about 85 degrees to about 95 degrees relative to the second alignment axis of the tibia. In particular embodiments, the tibial joint line is at an angle of about 85, 86, 87, 88, 89, 90, 91, 92, 93, 94, 95 degrees or any range therein, relative to the second alignment axis of the tibia. In one embodiment, the tibial joint line is substantially perpendicular (i.e., about 90 degrees relative) to the second alignment axis of the tibia.

With regards to the femoral and/or tibial shafts, any central portion/s or point/s along the shaft, such as proximal, middle or distal central portions, may be used as an anatomical indicator (i.e., first and/or third anatomical indicators) by the skilled person in performing the method of the present aspect.

It will be readily understood that the present invention should not be limited to the specific examples of anatomical indicators provided herein (i.e., first, second, third and/or fourth anatomical indicators). Rather, the term "anatomical indicator" as used herein refers to a readily identifiable feature, specific area and/or landmark within or on a limb, such as an arm or leg, and/or a bone, such as a femur or tibia. In this regard, the anatomical indicators used for determining, for example, a tibial mechanical axis, a femoral mechanical axis, a femoral joint line and a tibial joint line, are not to be limited to those anatomical indicators provided herein, but may also include other anatomical indicators as are known in the art.

Suitably, step (a) of the present method includes the step of subtracting the LDFA from the MPTA to define a pre-disease hip-knee-ankle angle (HKA). To this end, it will be understood that the term "hip-knee-ankle angle" refers to an angle formed by the femoral mechanical axis and the tibial mechanical axis. A HKA is preferably measured or determined from a full-length lower-limb radiograph and in healthy adults with a neutral alignment, the HKA is typically between 1.0° and 1.5° of varus (e.g., 1.0, 1.1, 1.2, 1.3, 1.4, 1.5 degrees and any range therein).

In one embodiment, the method of the present aspect further includes the step of classifying the pre-disease alignment of the knee based at least in part on the pre-disease HKA. Preferably, the pre-disease alignment is classified as:
 (a) valgus if the pre-disease HKA is positive in value;
 (b) varus if the pre-disease HKA is negative in value; or
 (c) neutral if the pre-disease HKA is substantially zero.

As will be appreciated by the skilled artisan, a varus alignment (e.g., a varus pre-disease alignment) refers to an inward angulation of a distal portion of a tibia on a coronal limb image, as measured by the HKA, whilst a valgus alignment (e.g., a valgus pre-disease alignment) refers to an outward angulation of a distal portion of a tibia on a coronal limb image, as measured by the HKA.

In certain embodiments, step (a) of the method of the present aspect suitably includes adding or summing the LDFA and the MPTA to define a pre-disease joint line obliquity value or angle. It will be understood that the term "joint line obliquity" or "joint line angle" can be defined as the angle between the mechanical axis of the limb (e.g., the tibial mechanical axis, the femoral mechanical axis) and a line which best parallels or indicates the joint space or line of the knee (e.g., the pre-disease joint line).

Depending on the joint line obliquity value or angle, the joint line can then be further categorized as, for example, (i) an apex distal joint line (i.e., a varus joint line) in which the joint line is rotated medially or inwardly relative to the knee so as to define an obtuse angle with respect to the mechanical axis of the limb; (ii) an apex proximal joint line (i.e., a valgus joint line) in which the joint line is rotated laterally or outwardly relative to the knee so as to define an acute angle with respect to the mechanical axis of the limb; or (iii) or a neutral joint line in which the joint line is substantially perpendicular to the mechanical axis of the limb.

In view of the above, the method may then further include the step of classifying a pre-disease joint line of the knee based at least in part on the pre-disease joint line obliquity value. Preferably, the pre-disease joint line is classified as:
 (a) an apex distal joint line if the pre-disease joint line obliquity value is less than 180°;
 (b) an apex proximal joint line if the pre-disease joint line obliquity value is greater than 180°; or
 (c) a neutral joint line if the pre-disease joint line obliquity value is substantially equal to 180°.

In certain embodiments, the method of the present aspect further includes the step of determining one or more of an anterior resection plane, a posterior resection plane and a distal resection plane of the femur and/or a proximal resection plane of the tibia from at least partly the pre-disease HKA and/or the pre-disease joint line obliquity value.

Referring to the above, once the pre-disease alignment of the knee in question has been determined, any coronal realignment (if required) of the extended or flexed tibia relative to the tibial and/or femoral mechanical axes can then be performed on, for example, a patient-specific model of the patient's limb. Preferably, the degree and type of any deformity and/or defect, such as varus and valgus, of the knee joint in question are assessed on the patient-specific model. This then allows for a determination of the amount of varus or valgus rotation (i.e. medial or lateral rotation of the tibia relative to its corresponding femur in a coronal arc) that is required for angular correction of the tibia, femur and/or the knee joint line relative to, for example, the tibial and/or femoral mechanical axes, so as to return the knee joint to the pre-disease alignment.

In one embodiment, the method of the present aspect further includes the step of rotating the tibia of the extended limb in a coronal plane relative to the femur, such that the tibial joint line and the femoral joint line are substantially parallel. It would further be appreciated that the method may further include the step of translating the tibia of the extended limb in a coronal plane relative to the femur to facilitate alignment of the knee joint. Accordingly, following such rotation and/or translation of the tibia, the tibial mechanical axis and the femoral mechanical axis are then returned to a pre-disease alignment, which can be a varus alignment, a valgus alignment or a neutral alignment depending upon the particular patient's anatomy.

Preferably, sagittal alignment and/or axial rotation of the tibia and/or femur are unchanged from their native or pre-operative state, as per the patient-specific anatomical data, after aligning the femur and/or tibia of said limb with the pre-disease alignment determined therefrom. It will be appreciated by the skilled artisan, however, that in order to achieve optimal coronal alignment additional translational and/or rotational correction or alignment of the knee joint may be required so as to account for, at least in part, any deformity caused by, for example, osteoarthritis.

A distal, posterior and/or anterior resection plane of the femur may then be established on a patient-specific model from the pre-disease alignment of the knee and a profile or dimension of a femoral component or prosthesis to be fitted on the femur. By way of example, a profile or dimension may be selected from one or more standard prosthetic devices, or custom prosthetic devices. The profile or dimension may be obtained from one or more product lines which may be from one or more implant manufacturers as are known in the art. Said profile or dimension typically indicates the size and/or positioning of one or more bony resections needed to fit a particular standard or custom prosthetic device. Preferably, the profile or dimension is of a prosthesis that has been sized and fitted appropriately for best coverage, bone conservation, flexion gap stability, patella tracking and/or placement without anterior femoral notching. In this regard, the distal resection plane is appropriately aligned on the patient-specific model relative to the pre-disease alignment.

A proximal resection plane of the tibia may also be established from a patient-specific model of the patient's knee similar to that described above for the resection planes of the femur. By way of example, the proximal resection plane of the tibia can be determined from at least partly the distal resection plane of the femur, the joint line and/or one or more dimensions of a femoral prosthesis and/or tibial prosthesis. To this end, and similar to that described above for the distal resection plane, the profiles, or one or more dimensions thereof, of the femoral and tibial prostheses may be superimposed onto the patient-specific model of the affected knee joint. Typically, the proximal resection plane of the tibia is determined from the distal resection plane and appropriate positioning of the femoral and tibial prostheses on the femur and tibia respectively of the patient-specific model that allows for suitable articulation therebetween. Generally, the proximal resection plane is also appropriately aligned on the patient-specific model relative to the pre-disease alignment.

It will be appreciated by the skilled person that the proximal resection plane may possess an anteroposterior slope when viewed in the sagittal plane. This slope is typically appropriate to the prosthesis to be fitted on the tibia and the individual patient's anatomy. Generally, this slope of the proximal resection plane is between about 0 and about 15 degrees, including, but not limited to, 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0 degrees or any range therein.

As used herein, the terms "approximately", "substantially" and "about" refer to tolerances or variances associated with numerical values recited herein. The extent of such tolerances and variances are well understood by persons skilled in the art. Typically, such tolerances and variances do not compromise the structure, function and/or implementation of the devices and methods described herein.

Further to the above, the method of the present aspect may further include the step of performing:
- (a) an anterior femoral resection based at least partly on the anterior resection plane;
- (b) a posterior femoral resection based at least partly on the posterior resection plane;
- (c) a distal femoral resection based at least partly on the distal resection plane; and/or
- (d) a proximal tibial resection based at least partly on the proximal resection plane.

It will be appreciated that the aforementioned resections of the femur and/or tibia can be performed by any means, such as cutting blocks, known in the art.

In another aspect, the invention resides in a method of determining a pre-disease alignment of a femur and/or a tibia of a knee, including the step of:
- (a) comparing a lateral distal femoral angle (LDFA) of the knee with a medial proximal tibial angle (MPTA) of the knee;
- wherein the pre-disease alignment of the knee is determined based at least partly on the comparison in (a).

In a related aspect, the invention provides a method of determining a prognosis for a patient with knee disease, including the steps of:
- (a) comparing a lateral distal femoral angle (LDFA) of the knee with a medial proximal tibial angle (MPTA) of the knee;
- (b) determining a pre-disease alignment of the femur and/or the tibia of the knee based at least partly on the comparison in (a);
- wherein the pre-disease alignment indicates or correlates with the prognosis for the patient.

The terms "prognosis" and "prognostic" are used herein to include making a prognosis, which can provide for predicting a clinical outcome (with or without medical and/or surgical treatment), selecting an appropriate course of treatment and/or surgery (or whether treatment or surgery would be effective) and/or monitoring a current treatment and potentially changing the treatment. This may be at least partly based on the pre-disease alignment of the patient's knee. A prognosis may also include a prediction, forecast or anticipation of any lasting or permanent physical or psychological effects of any disease or pathology, such as arthritis, present in the patient's knee prior to, for example, TKR surgery. Furthermore, prognosis may include one or more of determining a likelihood, potential or occurrence of implant failure, surgical responsiveness, implementing appropriate treatment regimes and/or achieving appropriate soft tissue balance. It will be appreciated that a positive prognosis typically refers to a beneficial clinical or surgical outcome or outlook, such as long-term implant success without the need for revision surgery, whereas a negative prognosis typically refers to a negative clinical or surgical outcome or outlook, such as patient dissatisfaction, persistent pain, implant failure and the need for revision surgery.

In a further related aspect, the invention provides a method of determining a resection plane of a femur and/or a tibia of a knee, including the steps of:
- (a) comparing a lateral distal femoral angle (LDFA) of the knee with a medial proximal tibial angle (MPTA) of the knee; and
- (b) determining a pre-disease alignment of the femur and/or the tibia of the knee based at least partly on the comparison in (a)
to thereby determine the resection plane.

Suitably, the resection plane is determined based at least partly on the pre-disease alignment determined in (b).

In yet another aspect, the invention resides in a method for facilitating soft tissue balancing of a knee for surgery, including the steps of:
- (a) comparing a lateral distal femoral angle (LDFA) of the knee with a medial proximal tibial angle (MPTA) of the knee; and
- (b) determining a pre-disease alignment of the femur and/or the tibia of the knee based at least partly on the comparison in (a);
- wherein the pre-disease alignment facilitates soft tissue balancing of the knee.

In this regard, it will be appreciated that an appropriate soft tissue balance or tension need not be substantially equal across the knee. To this end, the difference between a first soft tissue tension of a lateral knee portion or compartment and a second soft tissue tension of a medial knee portion or compartment is preferably 20 psi or less (e.g., 20, 19, 18, 17, 16, 15, 14, 13, 12, 11, 10, 9, 8, 7, 6, 5, 4, 3, 2, 1, 0 psi and any range therein), more preferably 15 psi or less and even more preferably 10 psi or less. Suitably, the first and/or second soft tissue tensions is 40 psi or less (e.g., 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, 0 psi and any range therein).

Additionally, the skilled artisan will understand that assessment or measurement of the soft tissue tension or pressure across the knee, including the first and second soft tissue tensions, may be performed by any pressure sensor device or method known in the art, such as the Verasense™ pressure sensor described in Example 3.

It will further be appreciated that the assessment or measurement of soft tissue balance or tension can be assessed throughout the range of motion of the knee in question. In particular embodiments, assessment or measurement of soft tissue balance or tension is performed when the knee is at 0 to 90 degrees of flexion (e.g., 0, 5, 10, 15, 20, 25, 30, 35, 40, 45, 50, 55, 60, 65, 70, 75, 80, 85, 90 degrees and any range therein).

The statements which follow apply equally to the four aforementioned aspects of the invention.

In particular embodiments, the aforementioned methods further include the initial step of determining the LDFA and/or the MPTA from a patient-specific image of the knee. Additionally, the above methods may further include the initial step of obtaining the patient-specific image of the knee, such as those hereinbefore described. Preferably, the patient-specific image is or comprises a long leg radiograph.

In certain embodiments, the step of determining the LDFA includes determining.
- (a) a first alignment axis from one or a plurality of first anatomical indicators; and
- (b) a femoral joint line from one or a plurality of second anatomical indicators; on the patient-specific image of the knee.

In one preferred embodiment, the first alignment axis is or comprises a femoral mechanical axis.

Again, it will be appreciated that the femoral mechanical axis and/or the femoral joint line can be determined by any method or anatomical indicator/s known in the art, such as those hereinbefore described. Suitably, the one or a plurality of first anatomical indicators are selected from the group consisting of a central portion of a femoral head, a central portion of a proximal femoral shaft, an intramedullary canal insertion point, a deepest portion of a trochlear groove and a central portion of an intercondylar notch. Additionally, the one or plurality of second anatomical indicators are suitably selected from the group consisting of a distal portion of a medial condyle and a distal portion of a lateral condyle.

For the three aforementioned aspects, the step of determining the MPTA suitably includes determining:
(a) a second alignment axis from one or a plurality of third anatomical indicators; and
(b) a tibial joint line from one or a plurality of fourth anatomical indicators; on the patient-specific image of the knee.

In one preferred embodiment, the second alignment axis is or comprises a tibial mechanical axis.

Similar to the above, it will be appreciated that the tibial mechanical axis and/or the tibial joint line can be determined by any method or anatomical indicator/s known in the art, such as those hereinbefore described. In particular embodiments, the one or a plurality of third anatomical indicators are selected from the group consisting of a central portion of a line extending between medial and lateral tibial spines, a central portion of a talus, a central portion of a distal tibial shaft and an anterior cruciate ligament tibial attachment point. In certain embodiments, the one or plurality of fourth anatomical indicators are selected from the group consisting of a proximal portion of a medial tibial plateau, a proximal portion of a lateral tibial plateau, a central portion of a lateral meniscus and a central portion of a medial meniscus.

Suitably, step (a) of the method of the above aspects comprises subtracting the LDFA from the MPTA to define a pre-disease hip-knee-ankle angle (HKA). Preferably, the aforementioned methods further include the step of classifying the pre-disease alignment of the knee based at least in part on the pre-disease HKA. In particular embodiments, the pre-disease alignment is classified as:
(a) valgus if the pre-disease HKA is positive in value;
(b) varus if the pre-disease HKA is negative in value; or
(c) neutral if the pre-disease HKA is substantially zero.

In some embodiments, step (a) comprises adding the LDFA and the MPTA to define a pre-disease joint line obliquity value. In this regard, the present methods suitably further include the step of classifying a pre-disease joint line of the knee based at least in part on the pre-disease joint line obliquity value. Preferably, the pre-disease joint line is classified as:
(a) an apex distal joint line if the pre-disease joint line obliquity value is less than 180°;
(b) an apex proximal joint line if the pre-disease joint line obliquity value is greater than 180°; or
(c) a neutral joint line if the pre-disease joint line obliquity value is substantially equal to 180°.

In certain embodiments, the present methods further include the step of determining a resection plane of the femur and/or tibia from at least partly the pre-disease HKA and/or the pre-disease joint line obliquity value. Preferably, the resection plane is one or more of a proximal tibial resection plane, a distal femoral resection plane, a posterior femoral resection plane and/or an anterior femoral resection plane.

Further to the above, the method of three aforementioned aspects suitably further includes the step of performing:
(a) an anterior femoral resection based at least partly on the anterior resection plane;
(b) a posterior femoral resection based at least partly on the posterior resection plane
(c) a distal femoral resection based at least partly on the distal resection plane; and/or
(d) a proximal tibial resection based at least partly on the proximal resection plane.

In another aspect, the invention provides an apparatus for assisting a surgeon performing surgery on a knee of a patient, the apparatus comprising a processor configured for comparing a lateral distal femoral angle (LDFA) of a knee with a medial proximal tibial angle (MPTA) of the knee and determining a pre-disease alignment of the femur and/or the tibia of the knee based at least partly on the comparison.

Suitably, the apparatus of the present aspect is for use in the method of any one of the aforementioned aspects.

Figure 36:
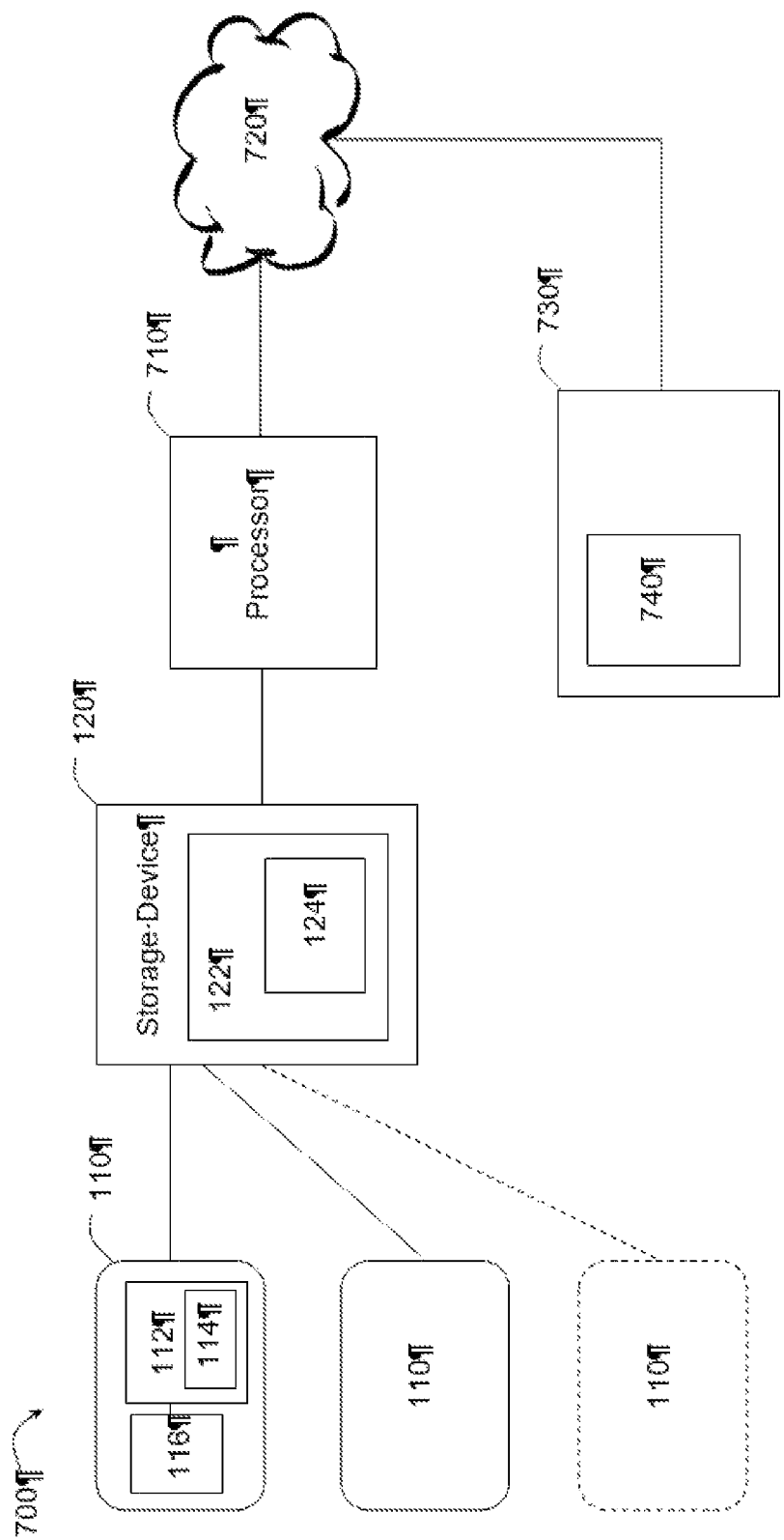
FIG. 36: illustrates an apparatus according to one embodiment of the invention.

FIG. 36 illustrates an apparatus or system 700 according to one embodiment of the invention. The apparatus 700 comprises a processor 710 in communication with one or more input devices 110 and a storage device 120. The processor 710 generates one or more reports 740 based on user input of patient-specific anatomical data, such as one or more of the femoral mechanical axis, the femoral joint line, the tibial mechanical axis, the tibial joint line, the MTPA and the LDFA, entered via the input device 110. In alternative embodiments, the processor 710 is further configured to automatically determine from, for example, a patient-specific image (e.g., a long leg radiograph) of the particular knee in question the LDFA and/or the MPTA, which may be received by the input device 110. In this regard, the processor 710 can be adapted to identify one or more of the anatomical indicators described herein from the patient-specific image of the knee in question. The processor 710 can, for example, form part of a server which comprises the storage device 120 or be a separate computing device that is in communication with the storage device 120.

In particular embodiments, the processor forms part of a computer, such as be a personal computer (PC), a tablet PC, a set-top box (STB), a Personal Digital Assistant (PDA), a cellular telephone, a web appliance, a network router, switch or bridge, or any computer capable of executing a set of instructions (sequential or otherwise) that specify actions to be taken by that computer, as are known in the art. The term "computer" shall also be taken to include any collection of computer that individually or jointly execute a set (or multiple sets) of instructions to perform any one or more of the methodologies discussed herein. The computer can operate as a standalone device or may be connected (e.g. networked) to other computers. In a networked deployment, the computer may operate in the capacity of a server, as described earlier, or a client computer in a server-client network environment, or as a peer computer in a peer-to-peer (or distributed) network environment.

The processor 710 provides a graphical user interface (GUI) 730 comprising the one or more reports 740 via a communications network 720, for example, to a computing device of a user or administrator. The one or more reports can include one or more metrics or readouts for, for example, determining a pre-disease alignment of the knee and/or one or more resection planes of the tibia and/or femur, as previously described, based on the patient-specific anatomical data. In some embodiments, the one or more reports include one or more visualisations or classifications of pre-disease alignment of the knee joint, as hereinbefore described, generated based on the patient-specific anatomical data and the GUI 730 can comprise one or more controls to select the one or more visualisations to be displayed.

The storage device 120 can comprise a computer memory 122 which can be, for example, a computer readable medium (e.g., software embodying or utilised by any one or more of the methodologies or functions described herein), such as, one or more hard disk drives or solid state drives. The computer memory 122 stores the patient-specific anatomical data. The computer memory 122 can also comprise computer readable code components 124 that when selectively executed by the processor 710 implements one or more aspects of the present invention, such as, generating aspects of the GUI 730 and providing the GUI 730 via the communications network 720.

Each input device 110 can comprise a computer memory 112 which can be, for example, a computer readable medium. The computer memory 112 comprises computer readable code components 114 (e.g., software embodying or utilised by any one or more of the methodologies or functions described herein) that when selectively executed by a processor 116 implements one or more aspects of the present invention, such as, generating and displaying the GUI 730 and receiving inputs, such as patient-specific anatomical data, via the input device 110. In some embodiments, the computer memory 112 stores the patient-specific anatomical data at the survey device 110 prior to transmitting the data to the storage device 130. The computer readable code components 114 may further be transmitted or received over a network via the communications network 720 utilising any one of a number of well-known transfer protocols (e.g., HTTP, UDP, TCP, USSD, FTP).

In one further aspect, the invention resides in a computer-readable medium, such as a non-transitory computer-readable medium, having stored thereon a computer program, which, when executed by a computer, causes the computer to perform the method of any one of the aforementioned aspects.

Throughout the specification the aim has been to describe the preferred embodiments of the invention without limiting the invention to any one embodiment or specific collection of features. It will therefore be appreciated by those of skill in the art that, in light of the instant disclosure, various modifications and changes can be made in the particular embodiments exemplified without departing from the scope of the present invention.

All computer programs, algorithms, patent and scientific literature referred to herein is incorporated herein by reference.

The following non-limiting examples illustrate the methods and apparatus of the invention. These examples should not be construed as limiting: the examples are included for the purposes of illustration only.

Example 1

Arithmetic HKA: A Method of Estimating Constitutional Lower Limb Alignment in the Arthritic Patient

Introduction

The distribution of lower limb alignment in the asymptomatic population is very different to that seen in patients that require total knee arthroplasty (TKA) (1). Progressive, asymmetric joint space narrowing during the disease process leads to exaggeration of the hip knee ankle (HKA) angle beyond changes due to bony deformity.

With the rise in prominence of kinematic techniques in TKA that aim to restore constitutional (pre-arthritic) alignment, accurate and straightforward techniques to estimate this are required. Many patient specific mapping systems use proprietary algorithms, the details of which are often not clear to the surgeon, and most require costly and otherwise non-clinically indicated 3D imaging (2-5).

We disclose in this Example a method of estimating the pre-arthritic constitutional alignment of the lower limb using long leg radiographs called the "arithmetic HKA". We validate this technique by comparing normal population alignment data against a sample of patients with established arthritis. The present Example illustrates that the arithmetic HKA is a reliable technique for estimating the pre-arthritic alignment of the lower limb when degenerative arthritis is present.

Methods

The asymptomatic population used in this comparison were 250 young healthy adults aged between 20 and 27 used in a previous cross-sectional prevalence study (1). These participants were recruited in a European country at high school and university campuses as well as movie theatres and job recruitment bureaus between October 2009 and March 2010. Fifty percent of the volunteers were female. Only healthy volunteers with no history of orthopaedic injury or disease were asked to participate. Both limbs were imaged and included in this population to give data from 500 knees.

The arthritic population consisted of 500 consecutive patients presenting for TKA at a private hospital in New South Wales, Australia, between October 2016 and March 2018. Only the knee to be operated on was analysed. These patients were aged between 44 and 88 years with a mean age of 66 years. 62% of patients in this group were female. Patients were included regardless of their underlying diagnosis and any previous history of surgery or trauma.

Radiographic Measurements

All of the healthy volunteers underwent full-leg standing digital radiography using the technique described by Paley (6). The volunteers stood barefoot in the "stand at attention" position with the feet together and the patellae orientated forward. The x-ray beam was centred on the knee with the tube at a distance of 305 cm. Three 350×430 mm cassettes were placed immediately behind the subject and the AGFA MIMOSA VIPS 1.3.00 software package (Agfa-Gevaert, Mortsol, Belgium) was used for digital stitching. A setting of 500 mA and a kilovoltage of 75 kV were used as the standard and individually adapted where necessary. The whole pelvis was included in the radiographs.

The arthritic patients underwent full-leg standing radiography as part of their routine pre-operative work-up. The x-rays were performed in a single radiology department using the same patient positioning technique as described above. The tube to knee distance was approximately 250 cm. Three 430 m×430 mm cassettes were placed behind the patient. Philips Digital Diagnostics Software (Philips Healthcare, North Ryde, Australia) was used for digital stitching. Kilovoltage settings varied between 70 kV and 85 kV per cassette. Once again, the whole pelvis was included in the radiograph.

Measurements were taken by a single observer in the asymptomatic group and by 2 observers in the arthritic group, using the same methodology, described below, which has been shown to have high inter- and intra-observer reliability (7).

The centre of the femoral head was determined using digital templating with concentric circles. The centre of the knee was determined as the intersection of the midline between the tibial spines and the midline between the femoral condyles. The centre of the ankle was defined as the mid-width of the talus. The mechanical axis of the femur was defined as the line from the centre of the femoral head to the centre of the knee. The mechanical axis of the tibia was defined as the line from the centre of the knee to the centre of the ankle.

The mechanical hip-knee-ankle angle (mHKA) was defined as the angle formed by the mechanical axes of the femur and tibia. The mHKA was expressed as a deviation from 180 degrees with a negative value for varus and a positive value for valgus alignment.

The lateral angle formed between the mechanical axis of the femur and the knee joint line of the distal femur was defined as the lateral distal femoral angle (LDFA). The medial proximal tibial angle (MPTA) was defined as the medial angle formed between the mechanical tibial axis and the knee joint line of the proximal tibia.

The joint line convergence angle (JLCA) was defined as the angle formed by the knee joint lines of the distal femur and proximal tibia. This was expressed as negative if the angle was formed laterally (medial joint space larger than lateral; valgus) and positive if the angle was formed medially (varus).

The Arithmetic HKA (aHKA)

FIG. 1 illustrates the change in coronal alignment and mHKA during medial compartment narrowing in degenerative arthritis. In this case, the already negative mHKA decreases further as the alignment of the limbs moves further from neutral. In the absence of significant bone loss, the MPTA and LDFA do not change during this process.

Figure 2:
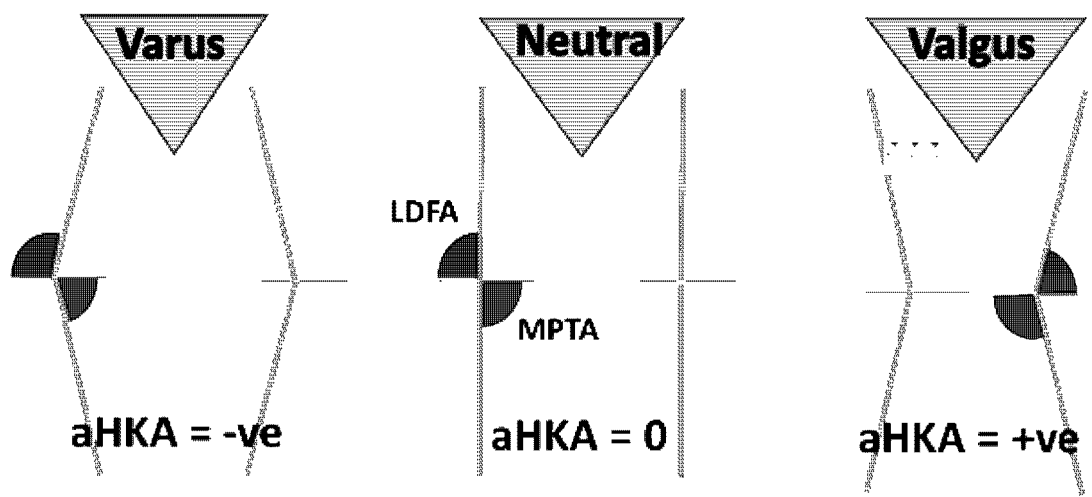
FIG. 2: Diagram illustrating the relationship between the LDFA and MPTA in varus, neutral and valgus lower limb alignment with the aHKA.

The arithmetic HKA is calculated by subtracting the LDFA from the MPTA. FIG. 2 illustrates that when these two angles are equal, the result is 0 and the mechanical axis of the limb passes through the centre of the knee. If the MPTA is greater than the LDFA, then the aHKA is positive, indicating a pre-disease valgus alignment of the limb. If the LDFA is greater than the MPTA then the aHKA is negative, indicating a varus limb alignment.

The calculation of the aHKA is not reliant on changes that occur at the joint space. However, the mHKA varies as asymmetric joint space loss occurs. The aHKA makes the assumption that in a parallel joint line, the aHKA equals the mHKA. Hence, the aHKA can be used to estimate pre-disease alignment.

Outcomes

We will compare the means, standard deviation and distributions of the following outcomes in a step-wise fashion in order to validate the aHKA.
1. The mHKA of the asymptomatic group will be compared to the mHKA of the arthritic group. This is to demonstrate that the mHKA changes with established knee arthritis.
2. The mHKA and aHKA will be compared in the asymptomatic group. The aim is to determine if the aHKA gives a reasonable estimation of pre-disease (normal) mechanical alignment of the limb.
3. The aHKA of both the asymptomatic and arthritic groups will be compared. This is to test the study hypothesis that the aHKA can estimate the pre-disease alignment of the limb by sharing a similar distribution.

Lastly, we will compare the means and distributions of the MPTA, LDFA, mHKA and aHKA between the two groups, and perform 2 tailed t-tests with unequal variance to test for significance. The hypothesis is that while the MTPA, LDFA, and therefore the aHKA will be similar between the two groups, the mHKA will be significantly different.

Results

Figure 3:
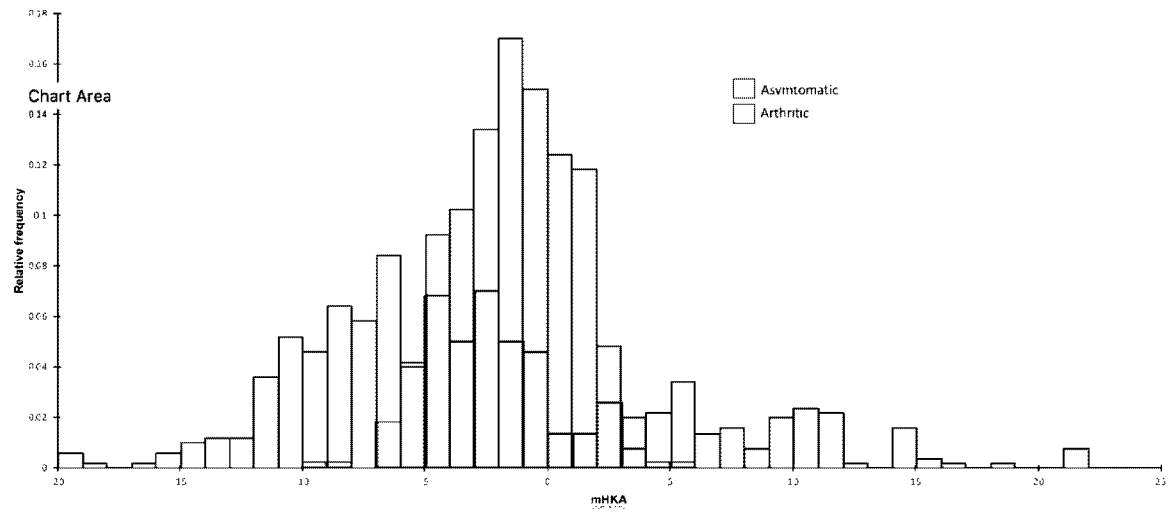
FIG. 3: Histogram of mHKA in Asymptomatic and Arthritic patients.

The difference in distribution of the mHKA of asymptomatic and arthritic patient groups is shown in the histogram in FIG. 3.

Figure 4:
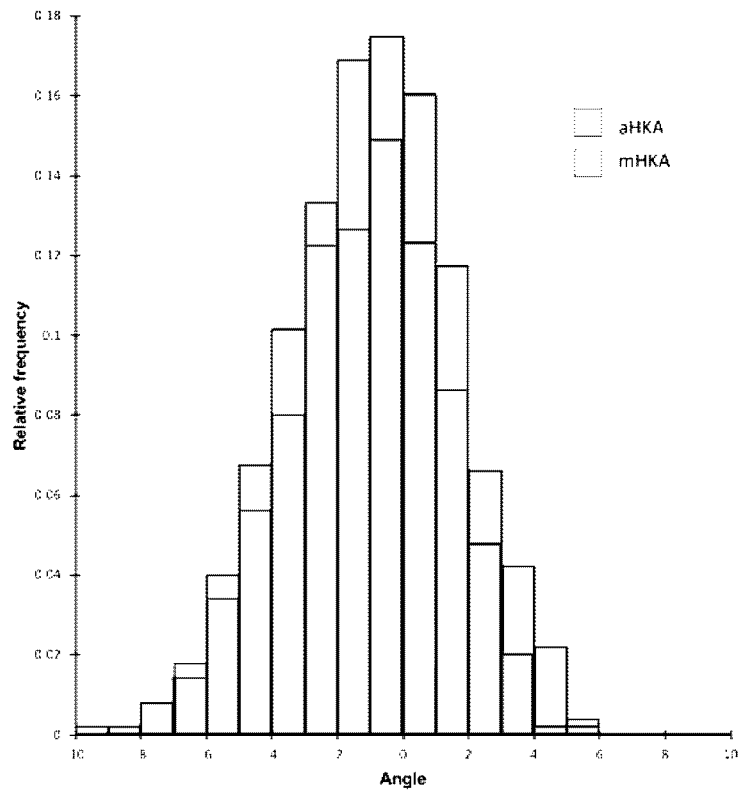
FIG. 4: aHKA vs mHKA for the asymptomatic group.

The aHKA was calculated for the asymptomatic patients and compared to the mHKA for the group. The histogram in FIG. 4 demonstrates that the distribution remains similar for these two variables.

Figure 5:
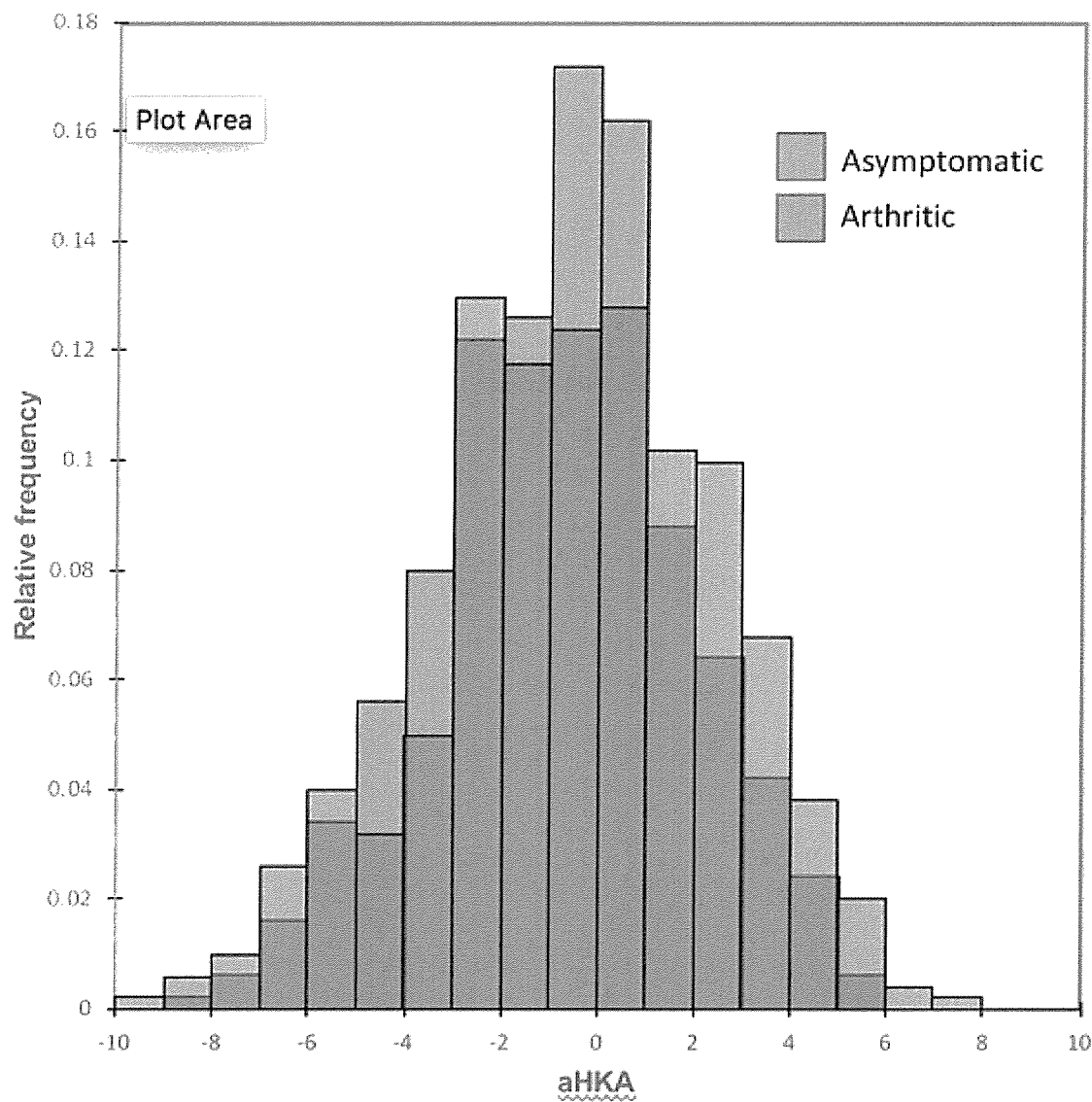
FIG. 5: aHKA in both asymptomatic and arthritic group.
Figure 6:
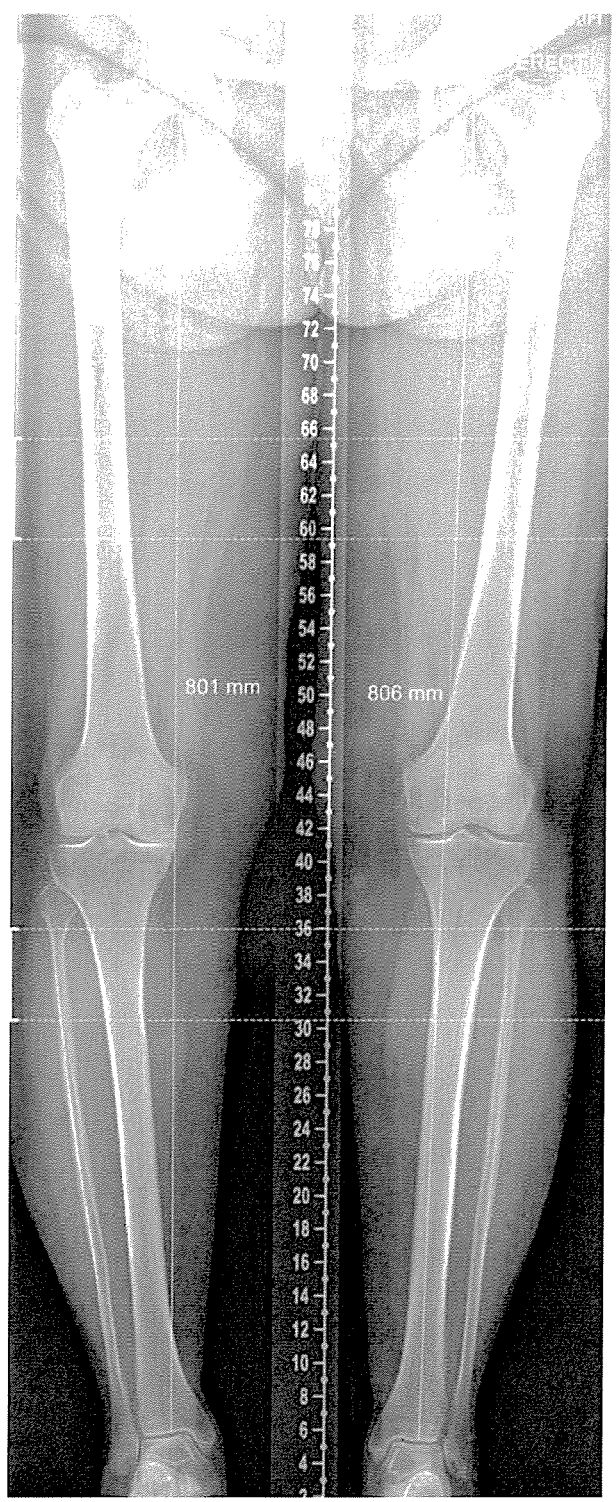
FIG. 6: Full length lower limb standing radiograph. Grade 4 Kellgren and Lawrence tibiofemoral osteoarthritis of right knee. Grade 1 tibiofemoral osteoarthritis left knee, serving as matched control.

The histogram in FIG. 5 allows direct comparison of the aHKA of both the asymptomatic and the arthritic patient groups.

There was no significant difference between the means of both groups for MPTA and the LDFA. There was a significant difference between the mHKA of both groups but the aHKA was statistically similar (Table 1).

TABLE 1

Table of results of radiographic and calculated measurements for both groups in degrees.

|  | Asymptomatic | Arthritic | p-value | Confidence interval (95%) |
| --- | --- | --- | --- | --- |
| MPTA | 87.04 (+/−2.07) | 87.32 (+/−2.14) | 0.0700 | −0.50 to 0.02 |
| LDFA | 87.90 (+/−1.74) | 88.09 (+/−2.06) | 0.2621 | −0.38 to 0.10 |
| mHKA | −1.33 (+/−2.34) | −2.88 (+/−7.39) | <0.0001 | 0.83 to 2.18 |
| aHKA | −0.87 (+/−2.54) | −0.77 (+/−2.84) | 0.5497 | −0.43 to 0.23 |

Results expressed as mean (+/−Std. Dev.)

Conclusion

Whilst the distribution of the mHKA of the normal population and pre-arthroplasty patients are very different, the aHKA for both groups is similar. There is no significant difference between the aHKA of the two groups, demonstrating that this calculation provides an accurate estimation of the pre-disease alignment of the limb. As techniques evolve in TKA surgery that are centred around restoring the constitutional alignment, the arithmetic HKA is a planning tool that enables prediction of the pre-arthritic HKA.

The aHKA is only an estimation of constitutional alignment. As described above, it assumes that the distal femoral and proximal tibial joint lines are parallel in the normal knee. The joint line convergence angle (JLCA) was measured in the asymptomatic group. The mean was −0.51 and the standard deviation 1.05. This indicates that the medial joint space is on average slightly wider than the lateral and when this is taken into account, the aHKA tends to underestimate the varus alignment and overestimate the valgus. This can be seen in FIG. 2, as the comparison between the aHKA and mHKA of the normal population shows a slight shift towards the right (valgus) end of the curve. This was not felt to be clinically relevant as 0.5 degrees is well within the margin of error of most measurement and cutting tools. In the interests of simplicity, the JLCA has been discounted from the calculation.

Another limitation in the technique is its accuracy in the presence of bone loss. At this point the MPTA and LDFA will change and the accuracy of the aHKA will be affected. The authors believe that in all but the most severe cases, features such as the bone on the periphery of the joint and the morphology of the remaining joint line allows a reasonable estimation of the degree of bone loss and allows the calculation to provide a useful guide as to the constitutional (pre-arthritic) alignment of the limb. This is reflected in the fact that the arthritic population included in this study did not exclude patients with significant bone loss.

In addition, we found a significant difference in means between the mHKA of the asymptomatic and arthritic groups. We would anticipate with a more equal number of varus and valgus knees in the arthritic cohort, that the mean difference would be negligible, whilst the variance would be increased as was noted. However, this finding most likely represents the predominance of varus knees presenting for TKA surgery in most populations.

Lastly, the two samples of normal and arthritic knees were not matched with regards to age, geographical location, racial background or gender. Despite this, we did not find any significant difference in the aHKA, MTPA and LDFA between normal and arthritic knee samples. This suggests that this tool is generalisable amongst other population sets as a predictor of the pre-arthritic alignment.

The validation of the arithmetic HKA demonstrates that this simple and cost-effective method can be used to estimate constitutional alignment of the lower limb following the onset of arthritis. This is of particular interest to those surgeons aiming to restore this alignment during TKA.

REFERENCES

1. Bellemans J, Colyn W, Vandenneucker H, Victor J. The Chitranjan Ranawat award: is neutral mechanical alignment normal for all patients? The concept of constitutional varus. Clin Orthop Relat Res. 2012; 470(1):45-53.
2. Young S W, Walker M L, Bayan A, Briant-Evans T, Pavlou P, Farrington B. The Chitranjan S. Ranawat Award: No Difference in 2-year Functional Outcomes Using Kinematic versus Mechanical Alignment in TKA: A Randomized Controlled Clinical Trial. Clin Orthop Relat Res. 2017; 475(1):9-20.
3. Waterson H B, Clement N D, Eyres K S, Mandalia V I, Toms A D. The early outcome of kinematic versus mechanical alignment in total knee arthroplasty: a prospective randomised control trial. Bone Joint J. 2016; 98-B(10):1360-8.
4. Dossett H G, Swartz G J, Estrada N A, LeFevre G W, Kwasman B G. Kinematically versus mechanically aligned total knee arthroplasty. Orthopedics. 2012; 35(2): e160-9.
5. Calliess T, Bauer K, Stukenborg-Colsman C, Windhagen H, Budde S, Ettinger M. PSI kinematic versus non-PSI mechanical alignment in total knee arthroplasty: a prospective, randomized study. Knee Surg Sports Traumatol Arthrosc. 2017; 25(6):1743-8.
6. Paley D, Pfeil J. [Principles of deformity correction around the knee]. Orthopade. 2000; 29(1): 18-38.
7. Colebatch A N, Hart D J, Zhai G, Williams F M, Spector T D, Arden N K. Effective measurement of knee alignment using AP knee radiographs. Knee. 2009; 16(1):42-5.

Example 2

The Arithmetic HKA: An Algorithm to Determine the Constitutional Limb Alignment in the Arthritic Knee Introduction Attempts to reproduce the constitutional alignment of the knee has recently gained popularity in total knee arthroplasty (TKA) surgery. The technique, termed kinematic alignment aims to restore both hip-knee-ankle (HKA) angle as well as joint line obliquity by reconstruction of the native distal femoral and proximal tibial articular surface joint lines. The concept is centred around preserving the three-dimensional knee kinematics and maintaining collateral ligament balance through a range of motion [1]. However, there are conflicting results in the literature on whether this technique improves clinical outcomes. In addition, there is currently no consensus on alignment boundaries amongst studies [2-5].

In 2012, a paper was published on the normal lower limb alignment and the concept of constitutional varus [6]. In that paper, only 66% of males and 80% of females had a HKA angle within −3° and +3° range, the boundaries that are currently accepted as best standard practice in mechanical alignment targets in total knee arthroplasty surgery [7-9]. In addition, one third of males had 3 or more degrees of constitutional varus. The study also noted that the mean HKA was approximately −1.3°, with males demonstrating greater constitutional varus than females.

For those aiming to restore the constitutional alignment of the lower limb when performing TKA, determination of the lower limb alignment once arthritis is established becomes more difficult. We have previously described a calculation, referred to as the "arithmetic HKA" (aHKA) in a cross-sectional study comparing 500 arthritic knees awaiting TKA surgery to 500 normal knees in Example 1. The calculation subtracts the lateral distal femoral angle (LDFA) from the medial proximal tibial angle (MPTA). Although as expected, the mechanical HKA (mHKA) in the arthritic cohort was significantly different between the two groups, the aHKA had a statistically similar centrality and dispersion to the mHKA to the normal population. This supports the concept that the aHKA calculation may be a valid predictive tool for determining pre-arthritic alignment. However, this study did not undertake matched comparisons to validate this concept because of the nature of the study design. As such, validation of the aHKA is imperative on a patient-by-patient basis.

The purpose of this study is to determine if the arithmetic HKA can determine the constitutional alignment of the lower limb when arthritis has developed by using the opposite radiographically normal limb as the comparator. The primary hypothesis is that the aHKA in the arthritic knee is similar to the mechanical HKA in the opposite limb when there is no arthritis present. If the arithmetic HKA is found to be predictive of the lower limb constitutional alignment prior to the onset of arthritis, then it will add further support to this tool being used for those surgeons wishing to perform kinematic alignment techniques.

Methods

Study Design

The radiographs of patients who had undergone either unicompartmental or total knee arthroplasty for end stage degenerative osteoarthritis were screened. In this study, the contralateral knee presenting with no significant tibiofemoral osteoarthritis was used as the control. The radiographs were taken from an imaging database of two orthopaedic surgeons who performed the surgeries. Ethics approval was obtained prior to commencement of the study.

Inclusion criteria were that the operated limb had to have Grade III or IV Kellgren and Lawrence tibiofemoral osteoarthritis indicative of moderate or severe joint space loss. In addition, grade 0 or I Kellgren and Lawrence changes, defined as nil or doubtful joint space loss on the contralateral side served as the normal knee control [10]. Patients were excluded if they had undergone a prior contralateral total or unicompartmental knee arthroplasty, if there was any extra-articular deformities of the femur or the tibia, if the patient had undergone a prior femoral or tibial osteotomy, and if there were prior intra- or extra-articular fractures of the femur or tibia.

Radiographic Technique

Standing full-length lower limb radiographs that included the pelvis were taken in one radiology unit using the technique described by Paley [11]. Positioning was in the "stand at attention" position with both patellae facing forward. Three 430 mm cassettes were used to undertake the examination and digital stitching was undertaken using the Philips Digital Diagnostics Software (Philips Healthcare, North Ryde, Australia). The tube to knee distance was approximately 250 cm. Kilovoltage settings varied between 70 kV and 85 kV per cassette.

Radiographic Parameters

The mechanical axis (MA) of the femur was defined as a line from the centre of the femoral head to the centre of the distal femur. The MA of the tibia was defined as a line at the midpoint of the tibia at the level of the knee joint to the centre of the tibial plafond. The LDFA was the lateral angle subtended by the MA of the femur and a line drawn across the articular surface of the distal femur at the most distal points of the lateral and medial femoral condyles. Similarly, the MPTA was the angle subtended medially by the MA of the tibia and a line drawn across the most prominent points of the lateral and medial tibial plateaus. The mechanical hip knee ankle angle (mHKA) was defined as the angular difference between the MA of the femur and MA of the tibia with varus represented as a negative value and valgus as positive value.

The arithmetic HKA is calculated by subtracting the LDFA from the MPTA (FIG. 1). This calculation has been validated in Example 1 to be capable of predicting the constitutional alignment at a population-based level. It however ignores the joint line convergence angle (JLCA) which shows slight convergence to the medial side of the knee of approximately 0.5° and has been shown to cause a slight valgus difference between the aHKA and mHKA in paired samples. For both simplicity and the fact that its value is considered to be within the margin of measurement error, it is ignored in the calculation of the aHKA.

One author (DS) screened the imaging database for patients who met the general requirements for inclusion. The radiographs were then reassessed, and agreement had to be reached between two authors (SM and DS) in order for the radiograph to be included. Firstly, the criteria for both arthritis in the one knee and no arthritis in the contralateral knee was assessed. In addition, the image quality with regards to rotation was to be met. We assessed rotational symmetry by 1. the patella being positioned symmetrically facing forward, 2. the lesser trochanters having a similar shape, and 3. the proximal tibiofibular joints having similar overlap. In addition, significant fixed flexion deformity of the arthritic limb was assessed by noting asymmetry of the knee intercondylar outline. If the radiographs were of poor quality due to patient positioning or they did not meet the inclusion criteria, then they were excluded.

All measurements were performed by an orthopaedic fellow (DS). A senior author (DC) undertook a subgroup analysis of 15 patients, repeated at one-week intervals to assess for inter- and intra-observer agreement.

Outcomes

The primary outcome is a comparison of the arithmetic HKA of the arthritic knee (aHKA-OA) to the mechanical HKA of the normal side (mHKA-N) as a prediction of the constitutional alignment of the lower limb prior to development of joint deformity. In addition, we will analyse the accuracy of the arithmetic HKA in determining constitutional alignment with deformities of greater than 8 degrees compared to deformities less than 8 degrees.

Sample Size Calculation

Our prior research has found that the aHKA in the normal population (aHKA-N) is −0.87° of varus with a standard deviation of 2.54°. A mean difference of 1.5° between the aHKA-N and aHKA-OA groups was felt to be within the standard error on both radiographic measurements and also when surgical osteotomies are created at the time of knee arthroplasty. In addition, we felt that a mean difference of 1.5° or less between groups would be indicative of parity between mHKA-N and aHKA-OA on clinical grounds. Based on these measures, we required a minimum of 46 paired radiographs to determine if a true difference existed between the sides.

Statistical Analysis

Descriptive statistics were used for calculation of means, standard deviations, and 95% confidence intervals. Matched pairs t-tests were used for comparison of means between the aHKA-OA and mHKA-N assuming normality of distribution on Shapiro-Wilk's test and Q-Q plots. Independent two tailed t-tests were used for analysis of mean differences in deformities greater and less than 8 degrees, as well as gender differences. Levels of inter-observer and intra-observer agreement between two observers were calculated by Pearson's correlation coefficients. A p-value was set at <0.05.

Results

Sixty-five patients had radiographs that met the initial inclusion criteria based on arthritic disease in one knee and normal or doubtful joint space loss in the contralateral knee. We excluded fourteen radiographs; nine were due to rotational asymmetry, two were due to the presence of prior femoral or tibial fractures resulting in extra-articular angular deformities, two were due to the presence of significant asymmetrical lateral distal femoral valgus most likely from juvenile physeal growth arrest, and one was due to asymmetric anteroposterior joint radiographic projectional differences from the presence of a flexion contracture in the arthritic knee. Our final analysis was of fifty-one radiographs and 102 limbs. The demographics of the study group are presented in Table 2.

The mean mechanical HKA of the normal knee was −1.19 degrees of varus (standard deviation 2.91 degrees). There was a significant difference between male and female knees with male knees having greater constitutional varus (mean−2.24 degrees; SD 2.65 degrees) than females (mean 0.00 degrees; SD 2.76 degrees). In addition, female knees had a statistically greater tendency for valgus alignment than males with respect to LFDA in both normal and arthritic limbs, as well as aHKA and mHKA in normal limbs (Table 3). The aHKA of the normal limb was in slight valgus compared to the mechanical HKA of the normal limb, with some of this difference being most likely contributed to by the JLCA which may contribute approximately 0.5 degrees of more valgus with the aHKA.

TABLE 2

Demographics of study group

| | |
|---|---|
| Mean Age (years) | 69 |
| Gender Ratio (M:F) | 28:23 |
| Laterality of arthritic knee (L:R) | 28:23 |
| Mean Height (cm) | 170.3 |
| Mean Weight (kg) | 86.0 |
| Mean BMI | 29.6 |

M = male,
F = female,
L = left,
R = right,
BMI = body mass index;
cm = centimetres;
kg = kilograms

TABLE 3

Radiographic parameters for all knees and differences between genders

| | All knees Mean ± SD | Male knees (n = 27) Mean ± SD | Female knees (n = 24) Mean ± SD | p value between genders |
|---|---|---|---|---|
| aHKA-OA (°) | −1.53 ± 3.27 | −2.22 ± 3.15 | −0.76 ± 3.30 | 0.11 |
| mHKA-OA (°) | −4.64 ± 5.2 | −5.52 ± 4.20 | −3.65 ± 6.08 | 0.21 |
| LDFA-OA (°) | 88.23 ± 2.61 | 88.97 ± 2.37 | 87.39 ± 2.66 | 0.02* |
| MPTA-OA (°) | 86.75 ± 2.55 | 86.85 ± 2.76 | 86.63 ± 2.35 | 0.75 |

TABLE 3-continued

Radiographic parameters for all knees and differences between genders

| | All knees Mean ± SD | Male knees (n = 27) Mean ± SD | Female knees (n = 24) Mean ± SD | p value between genders |
|---|---|---|---|---|
| aHKA-N (°) | −0.47 ± 3.06 | −1.43 ± 3.09 | 0.62 ± 2.69 | 0.01* |
| mHKA-N (°) | −1.19 ±2.91 | −2.24 ± 2.65 | 0.00 ± 2.76 | 0.005* |
| LDFA-N (°) | 87.49 ± 2.21 | 88.28 ± 2.02 | 86.60 ±2.12 | 0.006* |
| MPTA-N (°) | 87.00 ± 2.21 | 86.85 ± 2.70 | 87.18 ± 1.52 | 0.60 |

Figure 7:
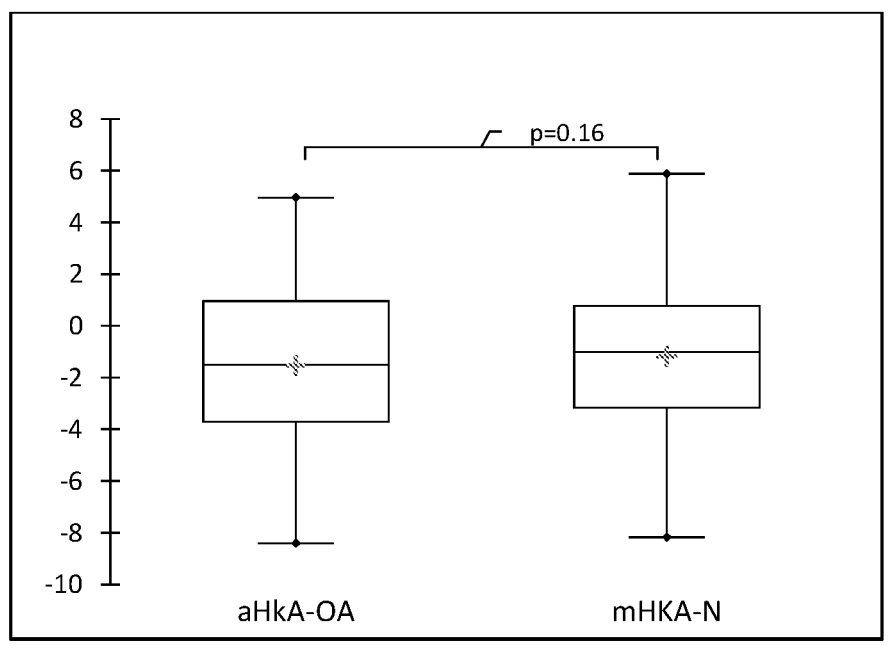
FIG. 7: Box Plots of aHKA-OA and mHKA-N knees. Vertical axis in degrees; negative angular values represent varus.

OA = arthritic limb;
N = normal limb;
aHKA = arithmetic hip-knee-ankle angle;
mHKA = mechanical hip-knee-ankle angle;
LDFA = lateral distal femoral angle;
MPTA = medial proximal tibial angle;
SD = standard deviation; minus values indicate varus;
*= significant p values Primary Outcome: aHKA-OA Versus m-HKA-N There was no significant difference between aHKA-OA and mHKA-N with a mean angular difference of −0.35 degrees (p=0.16, matched pairs t-test; 95% confidence interval −0.84 to 0.15 degrees). Analysis of data using Shapiro-Wilk tests and Q-Q plots confirmed normal distribution (p=0.57). When assessing differences between the aHKA-OA and mHKA-N between genders, females displayed a slightly higher trend where the aHKA was in more valgus compared to the mHKA-N. However, the differences between sexes were low and not statistically significant (mean difference 0.78 degrees, p=0.11; independent samples t-test). See Table 4 and FIG. 7.

TABLE 4

Summary of primary outcome difference between aHKA-OA and mHKA-N

| Variable | Mean ± SD | Range | 95% CI | p value |
|---|---|---|---|---|
| aHKA-OA (°) | −1.53 ± 3.27 | −8.41 to 4.96 | −2.45 to −0.61 | 0.16 |
| mHKA-N (°) | −1.19 ± 2.92 | −8.17 to 5.88 | −2.00 to −0.37 | (matched pairs t-test) −0.92 |
| Mean Difference Overall (°) | −0.35 ± 0.36 | N/A | −0.84 to 0.15 | N/A |
| Mean Difference Males (°) | −0.02 ± 1.77 | −3.04 to 4.28 | −0.19 to 1.76 | 0.11 (independent samples t-test) |
| Mean Difference Females (°) | 0.76 ± 1.68 | −1.66 to 4.75 | | |

SD = standard deviation;
CI = confidence interval;
N/A = not applicable

Relationship Between Deformity Severity and aHKA-OA Prediction of mHKA-N

The difference between aHKA-OA and mHKA-N was compared in those with deformities less than or equal to 8 degrees and deformities greater than 8 degrees (see table 5). There were 15 cases in the cohort with arthritic deformity of greater than 8 degrees. The mean difference between groups was 1.38 degrees which was statistically significant (p=0.009; 95% CI 0.25 to 2.39). There was no significant difference in variance between the two groups (Fishers F test; p=0.375, 95% CI −0.49 to 5.47).

TABLE 5

Analysis of difference between aHKA-OA and mHKA-N based on deformity severity

| | Mean Difference in aHKA-OA and mHKA-N ± SD (°) | Range (°) | 95% CI (°) | p value |
|---|---|---|---|---|
| Deformity > 8° (n = 15) | 1.32 ± 1.87 | −3.04 to 4.75 | 0.28 to 2.35 | 0.009* |
| Deformity < 8° (n = 36) | −0.06 ± 1.56 | −2.41 to 4.28 | −0.59 to 0.47 | |
| Difference in means between groups | 1.38 | N/A | 0.35 to 2.39 | N/A |

SD = standard deviation;
CI = confidence interval;
* = significant p values;
N/A = not applicable

Intra-Observer and Inter-Observer Agreement

Intra-observer agreement between measures one week apart was high with Pearson's R coefficient of 0.88 (p<0.0001) for observer one and 0.78 (p=0.0006) for observer 2. Similarly, inter-observer agreement at weeks one and two was high with a Pearson's R coefficient of 0.75 (p=0.001) and 0.74 (p=0.002) respectively. See Table 6.

TABLE 6

Intra-observer and Inter-observer agreement measures

| Observer 1 and 2 Agreement | Mean ± SD (°) | Min (°) | Max (°) | Pearson's R | Pearson's R 95% CI (°) | p value |
|---|---|---|---|---|---|---|
| 1 intra-observer agreement | 0.51 ± 1.9<br>0.57 ± 1.59 | −2.06<br>−2.09 | 4.75<br>4.04 | 0.88 | 0.66-0.96 | <0.0001* |
| 2 intra-observer agreement | 1.00 ± 1.77<br>1.03 ± 2.2 | −1.98<br>−1.78 | 4.02<br>5.84 | 0.78 | 0.45-0.92 | 0.0006* |
| 1-2 inter-observer week 1 agreement | 0.51 ± 1.9<br>1.00 ± 1.77 | −2.06<br>−1.98 | 4.75<br>4.02 | 0.74 | 0.37-0.91 | 0.001* |
| 1-2 inter-observer week 2 agreement | 0.57 ± 1.59<br>1.03 ± 2.2 | −2.09<br>−1.78 | 4.04<br>5.84 | 0.74 | 0.37-0.91 | 0.002* |

SD = standard deviation;
CI = confidence interval;
* = p values indicating statistically significant levels of agreement; all data in degrees

Discussion

As surgical techniques in the field of knee arthroplasty evolve, it is now increasingly recognised that attempting to more closely restore the constitutional alignment may reduce the requirement for significant ligament balancing, and potentially return the soft tissue envelope to a more physiologic state. To date however, the capacity to determine the constitutional knee alignment once joint space loss, deformity and in more advanced cases bone erosion and subluxation has developed has not been defined. Having a planning tool to determine the constitutional alignment prior to performing surgical resections of the distal femur and proximal tibia would be invaluable to surgeons aiming to restore the knee to its pre-arthritic alignment.

The mechanical HKA in an arthritic knee varies considerably to the mechanical HKA prior to the onset of the tibiofemoral osteoarthritis. In our prior study comparing two large population samples, we were able to demonstrate that when the arithmetic HKA was applied to an arthritic sample requiring TKA, the arthritic sample demonstrated similar centrality and dispersion when compared to the normal group. The purpose of this study was to validate the arithmetic HKA as a tool to predict the pre-arthritic alignment once arthritis has occurred by comparing the arithmetic HKA in an arthritic knee to the mechanical HKA in the normal contralateral knee. In this way, we aimed to validate the arithmetic HKA's predictive capability on an individual basis, as the constitutional alignment from one individual to another is highly variable.

This study found that the arithmetic HKA in the arthritic knee was capable of predicting the mechanical alignment in the contralateral normal knee within 0.35 degree. This was within the margin of error of 1.5 degrees that was set as a target at the onset of this study which we believe is within the measurement error range in the general population, as well as being within the surgical resection accuracy at the time of performing total knee arthroplasty. This result supports the use of the arithmetic HKA algorithm in determining the constitutional alignment once arthritis has occurred.

The calculation had similar accuracy between males and females, although we noted a trend for the aHKA to be in slightly more valgus in females when compared to male knees where both the aHKA-OA and mHKA-N were more closely aligned. It is likely that this difference relates to the finding that female knees had a statistically lower LDFA angle (greater distal femoral valgus) than males, both when comparing this angle in normal knees and arthritic knees between sexes. This finding was different to the results noted in the 2012 paper on normal knee alignment where the MPTA was significantly different between sexes, but the LDFA was not.

When looking at its capacity to determine the constitutional alignment in more advanced deformities, we found that there was a greater difference between the aHKA-OA and mHKA-N in those knees with deformities outside of 8 degrees when compared to knees with lesser deformity. This mean difference was 1.32 degrees, and although being within our defined margin of error, the upper boundary of the 95% confidence interval was 2.35 degrees. It is probable that the capacity of the arithmetic HKA to determine the constitutional alignment in more advanced states is lower. This makes intuitive sense as when arthritis progresses, bone erosion may alter the landmarks for determination of the LFDA and MPTA, both of which are required for calculation of the aHKA. In addition, there is increased likelihood of joint flexion contractures which may subtly alter the extension surface articular topography for landmark referencing that will contribute to measurement error. The other consideration is that this difference may have been related to a sampling error as there were only 15 patients who had deformities greater than 8 degrees.

In the present Example, the calculation of the arithmetic HKA was performed using high quality full length lower limb alignment radiographs with accurate stitching of cassette stitching. The benefit of this imaging modality is that it is less costly, has lower radiation dosing and is more readily available than computed tomography. It also allows for weight bearing assessment of limb deformity, although the calculation in itself is not affected by this issue due to the fact that it references off bony landmarks. The arithmetic HKA has not been validated with computed tomographic or magnetic resonance imaging, although it is possible that these more advanced imaging modalities may offer increased accuracy by controlling for rotational and sagittal limb positioning issues that may increase measurement error. Secondly, the calculations in this study were performed on a web-based imaging platform that we believe is more accurate than manual templating on the plain radiographs. Thirdly, we excluded all patients with poor quality imaging, and hence this needs to be considered when interpreting the results of the study and clinical applicability. It is critical that the clinician individually scrutinises the quality of the imaging, and if this cannot be guaranteed, then they should not be relied upon for calculation of the constitutional alignment.

Conclusion

A technique to determine the constitutional alignment of the knee when arthritis is established is of importance to knee arthroplasty surgeons. The results of this study support the use of the arithmetic HKA for prediction of the constitutional alignment in the arthritic knee. The calculation has similar accuracy between genders and potentially greater accuracy with lesser degrees of deformity.

REFERENCES

1. Howell, S. M., et al., *Does a kinematically aligned total knee arthroplasty restore function without failure regardless of alignment category?* Clin Orthop Relat Res, 2013. 471(3): p. 1000-7.

2. Calliess, T., et al., *PSI kinematic versus non-PSI mechanical alignment in total knee arthroplasty: a prospective, randomized study.* Knee Surg Sports Traumatol Arthrosc, 2017. 25(6): p. 1743-1748.

3. Dossett, H. G., et al., *Kinematically versus mechanically aligned total knee arthroplasty.* Orthopedics, 2012. 35(2): p. e160-9.

4. Waterson, H. B., et al., *The early outcome of kinematic versus mechanical alignment in total knee arthroplasty: a prospective randomised control trial.* Bone Joint J, 2016. 98-b(10): p. 1360-1368.

5. Young, S. W., et al., *The Chitranjan S. Ranawat Award: No Difference in 2-year Functional Outcomes Using Kinematic versus Mechanical Alignment in TKA: A Randomized Controlled Clinical Trial.* Clin Orthop Relat Res, 2017. 475(1): p. 9-20.

6. Bellemans, J., et al., *The Chitranjan Ranawat award: is neutral mechanical alignment normal for all patients? The concept of constitutional varus.* Clin Orthop Relat Res, 2012. 470(1): p. 45-53.

7. Berend, M. E., et al., *The Chetranjan Ranawat Award: Tibial Component Failure Mechanisms in Total Knee Arthroplasty.* Clinical Orthopaedics and Related Research®, 2004. 428: p. 26-34.

8. Fang, D. M., M. A. Ritter, and K. E. Davis, *Coronal alignment in total knee arthroplasty: just how important is it?* J Arthroplasty, 2009. 24(6 Suppl): p. 39-43.

9. Ritter, M. A., et al., *Postoperative alignment of total knee replacement. Its effect on survival.* Clin Orthop Relat Res, 1994(299): p. 153-6.

10. Kellgren, J. H. and J. S. Lawrence, *Radiological assessment of osteo-arthrosis.* Ann Rheum Dis, 1957. 16(4): p. 494-502.

11. Paley, D., *Principles of Deformity Correction.* 2003, Heidelberg, Germany: Springer-Verlag.

Example 3

Restoring the Constitutional Alignment of the Knee with a Restrictive Kinematic Protocol Improves Soft Tissue Balance During Total Knee Arthroplasty Introduction Total knee arthroplasty (TKA) is a successful operation for treating pain and improving mobility in end-stage degenerative arthropathy. Despite advances in implant design and surgical technique, up to 20% of patients are less than satisfied, rating the outcome of their knee arthroplasty as fair or poor [1-3]. Outcomes registries such as the Arthroplasty Clinical Outcomes Registry (ACORN) in Australia [4] and the Swedish Knee Arthroplasty Register [5] report similar rates of dissatisfaction. The causes of this dissatisfaction are not clearly understood but are likely to be multifactorial, with surgical factors such as instability, malalignment, patellofemoral maltracking and stiffness regularly cited as potential contributors [3, 5-8].

The traditional technique of achieving alignment in TKA is to resect the distal femoral and proximal tibial joint surfaces perpendicular to the long axis of each bone. This is termed the "mechanical alignment" method. External rotation of the femoral resections off the posterior aspect of the femur compensates for the loss of the normal varus alignment of the proximal tibia, leading to parallel cuts with the knee both in extension and flexion. The knee joint is parallel to the floor with the weight bearing axis of the lower limb passing through the middle of the knee joint. These conventional cuts have long been believed to create the best mechanical environment for the function and longevity of the prosthesis.

Advances over recent decades in fixation, manufacturing and improved wear characteristics of the bearing surfaces of total knee prostheses have led to a steady improvement in survivorship of the implants [9]. During this time, however, outcomes have remained consistent, with 15-20% of patients continuing to be dissatisfied with their joint replacement [1-3]. This satisfaction plateau has led some to question the need to focus on creating the ideal mechanical environment for the implant, and instead to suggest ways to accurately recreate the constitutional (or pre-arthritic) alignment of the knee, and thereby achieve improved patient outcomes [10].

In 2012, Bellemans introduced the concept of 'constitutional varus' and demonstrated the wide range of limb alignments in the normal population [11]. Subsequent to this, the "kinematic alignment" method was described by Howell et al. The aim of this method is to recreate the constitutional knee joint by recreating the movement around three axes that make up normal knee motion [12]: a transverse axis in the femur about which the tibia flexes and extends; a transverse axis in the femur about which the patella moves; and a longitudinal axis in the tibia about which the tibia internally and externally rotates on the femur. In order to achieve this, the bone resections are made parallel to the surface of distal femur, posterior femur and proximal tibia, as opposed to perpendicular to the long axis of each bone. The theory is that a knee aligned to the patient's native anatomy will be better balanced and therefore will require little if any adjustment of the soft tissue envelope to achieve normal knee motion [10]. There remains conflicting evidence on whether kinematic alignment techniques improve clinical outcomes in TKA [13-16].

Intra-operative sensors are a new technology that allows the surgeon to precisely quantify soft tissue balance in TKA throughout a range of motion [17]. Using these advances, there is evidence that a balanced TKA may lead to improved patient outcomes [18, 19]. Notably, there has been no work on whether restoring the constitutional alignment with kinematic techniques leads to a more balanced knee than the mechanical alignment method despite this being considered the major contributor to purported improved outcomes with this technique.

The aim of this study was to determine whether ligament balance is more readily achieved by restoring the constitutional alignment versus the traditional method using mechanical alignment. The determination of knee balance is via the use of compartmental pressure sensor data as an objective and quantifiable measure of knee balance. The primary hypothesis of this trial is that knees aligned to restore a patient's constitutional alignment within a restrictive kinematic safe zone will have a lower intercompartmental pressure difference at 10 degrees of knee flexion compared to those aligned with a neutral mechanical axis and a horizontal joint line. Our secondary hypothesis is that knee balance with a restrictive kinematic protocol would be improved at higher degrees of knee flexion and also that less balancing procedures would be needed in this group. The results of this trial will aim to inform future clinical practice regarding soft tissue balance and kinematic alignment strategies in total knee arthroplasty.

Methods and Analysis

Study Design

We conducted a randomized controlled, parallel-group superiority trial comparing intra-operative soft tissue balance in TKAs implanted using a Kinematic Alignment (KA) technique as the intervention group versus those aligned by Mechanical Alignment (MA) as the control group. The study protocol received ethics approval (Bellberry Limited Ethics Committee; #2017-12-911) and was registered with the Australian New Zealand Clinical Trials Registry (#ACTRN12617001627347p).

Two knee arthroplasty surgeons (SJM, DBC) performed all surgeries at one hospital. During the enrolment period, all patients whom primary TKA was indicated were screened for eligibility by the individual surgeon and their teams. Although the surgeons were not be blinded to the allocation, the participants, assessors and statisticians were blinded to enable unbiased collection of patient-reported and functional outcomes as future studies on this patient group will define any patient perceived benefits.

Patients were considered eligible for inclusion if they were indicated for either primary unilateral or bilateral total knee arthroplasty with a diagnosis of osteoarthritis, inflammatory arthritis or post-traumatic osteoarthritis. Exclusion criteria were those patients requiring revision TKA and patients with a prior grade 3 ligamentous knee injury to posterolateral corner (PLC) or lateral collateral ligament (LCL). Grade 3 medial collateral ligament (MCL) injuries treated conservatively were included so long as they were deemed by the surgeon to have healed with a maximum of Grade 1 laxity. Any patient with prior femoral, tibial or patellofemoral osteotomies, or extra-articular femoral or tibial malunions with deformity greater than 5 degrees in any plane were excluded. Lastly, any patients who were unable to provide consent or fulfil the study requirements due to cognitive incapacity or English-language deficiency were excluded.

Interventions

In the KA group, the surgeon performed the initial bony resections according to a restrictive kinematic plan that was defined prior to randomization (see Pre-operative Planning) In the MA group, the surgeon performed the initial bony resections aiming for tibial and femoral component position perpendicular to the mechanical axis of the bone and an overall hip-knee-ankle (HKA) angle of 0 degrees.

Pre-Operative Planning

All patients underwent pre-operative weight-bearing, long leg alignment radiographs. These were taken using the technique described by Paley [20]. Pre-operative HKA angle, Medial Proximal Tibial Angle (MPTA) and Lateral Distal Femoral Angle (LDFA) was measured for the operative knee using techniques described by Bellemans [11].

This 'restrictive zone' for this study was defined as 86 to 93 degrees for recreation of both the LDFA and the MPTA and −5 degrees varus to +4 degrees valgus for the HKA. The authors set the parameters of the 'restrictive zone' centred on the means from Bellemans' study describing the normal distribution of these angles [11] and also based on studies comparing analysis of alignment against survivorship by Parratte [21] and Ritter [22]. It was felt by the senior knee arthroplasty authors that this safe zone would allow approximately 70% of patients in the KA group to have their constitutional alignment restored according to data from Bellemans et al., whilst minimizing the risk of significant component malalignment that may increase the risk of implant failure. It has also been the experience of our group that errors of up to 1 degree commonly occur in individual implant positioning with the use of optical navigation. This could result in undesirable alignment errors of up to +/−5 degrees for implant positioning, and up to +/−6 degrees for HKA.

Proximal tibial and distal femoral resection angles were measured using a software-based measurement tool. If the pre-operative plan required LDFA and MPTA resections that would lead to an HKA outside of the safe zone of −5 to +4 degrees, then the LDFA and MPTA were proportionally adjusted so the total HKA did not exceed the safe zone threshold. In order to reduce the risk of implant subsidence or loosening in the presence of osteoporotic bone, patients with a documented history of osteoporosis requiring bone anti-resorptive therapies, patients with documented insufficiency fractures or patients greater than 80 years of age had the angle range for LFDA and MPTA narrowed to 87 to 93 degrees and a HKA safe zone of −4 to +3 degrees.

Surgical Technique

The Legion posterior-stabilized fully cemented total knee arthroplasty system was used with patellar resurfacing (Smith & Nephew, Memphis, TN). The distal femoral and proximal tibial resections were made as per the allocated group. Femoral component rotation was initially set in the KA group parallel to the native posterior condylar axis and in the MA group parallel to the surgical transepicondylar axis. In the KA group, if the planned tibial cut angle had been reduced in order to fall within the safe zone, then the femoral component was externally rotated by the same amount that the tibial cut was reduced in order to rebalance the flexion gap. A secondary check of flexion gap symmetry was undertaken using a gap tensiometer.

All TKAs were implanted using full optical navigation (OrthoMap Precision Navigation, Stryker, Kalamazoo, MI, USA) to improve accuracy as well as ensuring consistency between groups. Trial components were inserted prior to any soft tissue release (other than those required by a standard medial parapatellar approach). During trialling, the surgeon determined the most suitable size of tibial insert. The extensor mechanism was approximated using a towel clip as this has been shown to alter knee ligament tension compared to when the patella is displaced laterally [23]. The knee was then cycled through a full range of movement. Assessment of knee extension with the computer navigation system was performed concurrently to ensure that an extension loss of no more than 5 degrees was apparent.

Following this, a pressure "sensor" (VERASENSE™, OrthoSensor, Dania Beach, FL, USA) that quantifies intercompartmental pressure loads and tibiofemoral contact points was inserted matching the same size and thickness of the trial insert. The surgeon supported the posterior thigh with one hand and rested the heel in the other to reduce the amount of varus and valgus stress placed on the knee. The initial knee compartmental pressures were recorded at 10, 45 and 90 degrees of knee flexion using the optical navigation to confirm the flexion angles. These steps were repeated by one surgical assistant in all cases to assess interobserver reliability and consistency. All data measurements were then recorded by a non-operative member of the surgical team.

The surgeon then undertook final balancing of the total knee arthroplasty by standard operating techniques using the sensor. All knees were balanced to achieve an intercompartmental pressure difference of 15 psi or less at all 3 flexion angles which has been validated in prior studies to correlate to improved patient outcomes [17]. In general, a bone recut was performed if the absolute pressure in one compartment was greater than 60 psi, or an intercompartmental pressure difference was greater than 40 psi between compartments. If the intercompartmental pressure difference was less than 40 psi and greater than 15 psi, then a soft tissue release was performed. The aim was to achieve a final intercompartmental pressure difference of less than 15 psi with pressure in any compartment less than 40 psi at all three flexion angles.

Allocation

A 1:1 randomization scheme was generated using the computerized program at Randomization.com (http://www-.randomization.com). Permutated blocks were used, with a block size of 4 and 33 blocks allowing for randomization of a potential 132 subjects. Sealed, opaque envelopes contained card with the words "Kinematic Alignment" or "Mechanical Alignment". There was no external information indicating which option was contained on the card within.

Pre-operative planning was undertaken on each patient for both the intervention and control arms of the study Immediately after induction of anaesthesia, a member of the surgical team opened the next envelope in the randomization sequence from a locked box kept in theatre, and the patient was allocated to either the KA or MA group. Bilateral procedures were included, and randomized once, with both sides being assigned to the same group.

Primary Outcome Measure

The primary outcome measure of this study was initial mean pressure difference between the medial and lateral compartments at 10 degrees of flexion. Because the compartment pressures were assessed by both the operating surgeon and the surgical assistant, the mean difference of the two readings constituted the primary outcome measure.

Secondary Outcome Measures

Initial medial and lateral compartmental pressures were also compared in both groups at 45 degrees and 90 degrees of knee flexion. Optimal knee balance was defined as a pressure difference of less than 15 psi between compartments at 10 degrees, 45 degrees and 90 degrees of knee flexion, with no pressure exceeding 40 psi. The proportion of cases with balanced knees was assessed at each flexion angle.

Requirements for knee balancing was recorded in both groups. This included the frequency of bone recuts for significant imbalance as well as soft tissue releases required for lesser degrees of imbalance. In addition, we recorded the presence of "lift off" (no contact in one compartment) which is indicative of severe imbalance. We defined lift off as agreement between the 2 observers that no pressure was recorded in one compartment in any knee position, and with at least 20 psi of pressure in the contralateral compartment. This was to ensure that the zero value recorded was not due to an overall reduced joint tension, as opposed to significant tightness of the collateral ligament on the contralateral side of the lift off occurring which produces the phenomena of tibiofemoral joint separation. Total operative time from skin incision to wound closure was recorded.

Pre-operative radiographic data recorded included hip-knee-ankle (HKA) angle, lateral distal femoral angle (LDFA) and medial proximal tibial angle (MPTA). Radiographic assessment of post-operative alignment was undertaken using a CT Perth Protocol which has the capacity to determine multiplanar implant positioning [24, 25]. Radiographic parameters included HKA angle, LDFA, MPTA, femoral and tibial sagittal angle, femoral component rotation and tibial component rotation.

Sample Size

The senior authors have previously recorded the initial and final intercompartmental pressures of 280 consecutive TKAs using the VERASENSE™ device. The mean initial 10-degree pressure difference was 30 psi (SD 30 psi). The manufacturers recommend a pressure difference between lateral and medial compartments of less than 15 psi in order for the knee to be balanced. Using a 5% significance, a standard deviation of 30 and an 80% power to detect a difference of 15 psi, a sample size of 125 was required. As the primary outcome measure was an intraoperative measurement, a loss to follow-up assumption was not required.

Statistical Analysis

Descriptive statistics were used to analyze patient demographics including age, gender, side of surgery, body mass index and knee deformity. Normality of data was assessed using Shapiro-Wilk tests and Q-Q plots. Independent and paired samples Student's t-test were used to compare differences in means with continuous variables. The Chi-squared test was used for categorical data analysis as appropriate. Pearson's correlation coefficient was used to compare sensor measures between observers. As the primary outcome for this study was pressure difference recorded after allocation to treatment had occurred, an as-treated analysis was performed in the primary analysis. Statistical significance was set with a p value of <0.05.

Results

Figure 11:
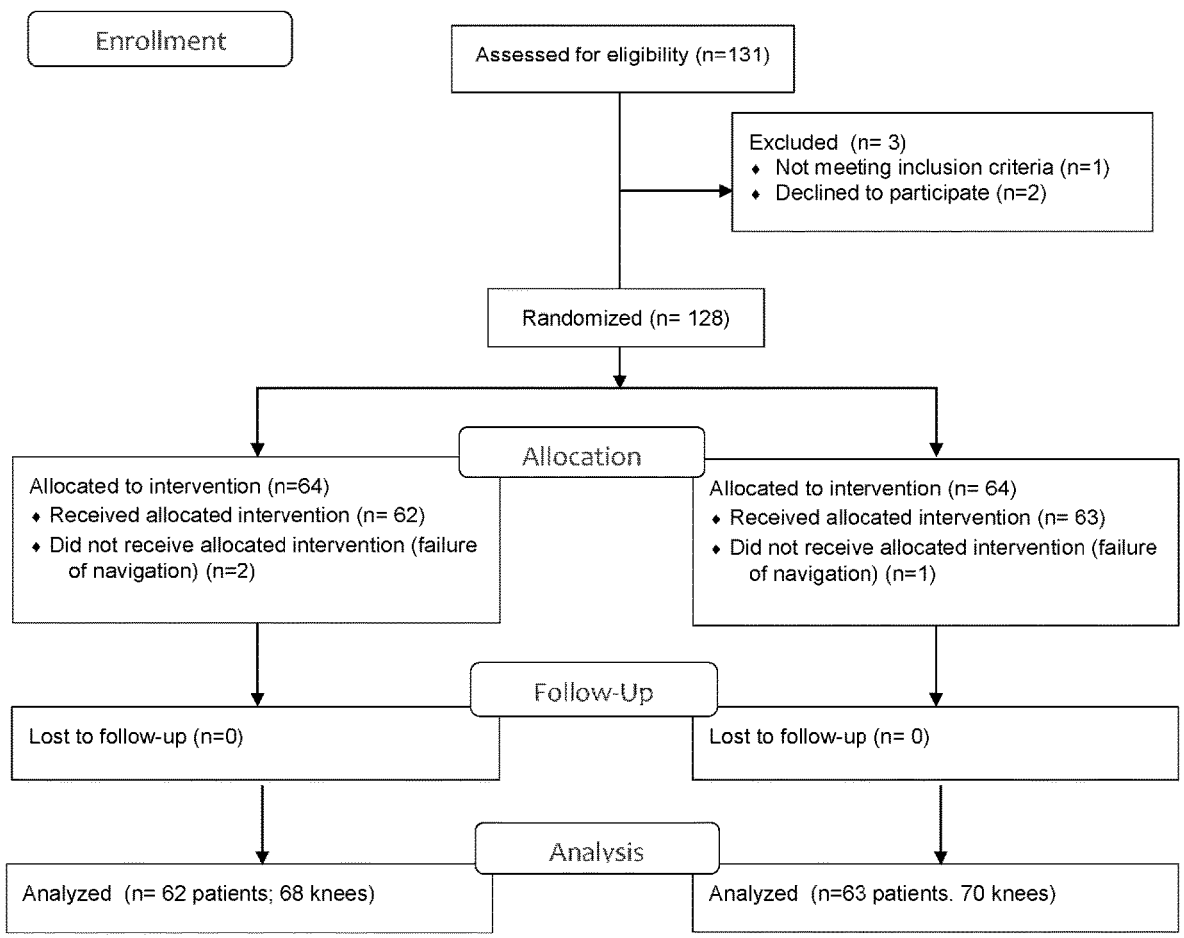
FIG. 11: Consort diagram.

One hundred and thirty one consecutive patients undergoing TKA were assessed for eligibility for inclusion. Two patients refused to participate, and one other patient did not meet the inclusion criteria due to extra-articular long bone deformity related to Paget's disease. Of the 128 patients who were assigned to an intervention, three did not receive the allocated treatment due to failure of the navigation system in those cases. These three patients subsequently underwent TKA using conventional guides and were excluded from final analysis due to failure to assess outcome measures. There were 62 patients (68 knees) in the MA group and 63 patients (70 knees) in the KA group who received the allocated intervention and were analyzed on an as-treated basis (see Consort Diagram in FIG. 11). There were six bilateral procedures in the MA group and seven in the KA group.

The demographics for the study population is presented in Table 7. There were no significant differences between groups with regards to age, gender, laterality, body mass index (BMI) and preoperative limb alignment.

TABLE 7

Patient Demographics

|  | Mechanical Alignment | Kinematic Alignment | p value |
|---|---|---|---|
| Number of patients | 62 | 63 |  |
| Number of TKA cases | 68 | 70 |  |
| Mean age (range) | 69.0 (56-86) | 67.4 (36-89) | 0.322[†] |
| Gender ratio (M:F) | 28:34 | 23:40 | 0.22[*] |
| Side (L:R) | 26:42 | 34:36 | 0.22[*] |
| BMI | 30.1 | 30.2 | 0.88[*] |
| Mean preoperative HKA (degrees) | −3.7 | −2.8 | 0.51[†] |
| HKA range (degrees) | −18 to +15 | −16 to +20 |  |

M = male;
F = female;
L = left;
R = right;
BMI = body mass index;
[†]Independent Students t-test;
[*]Chi square test Comparison of Sensor Measures Between Observers There was moderate to high correlation for pressure sensor measures at each flexion angle between the surgeon (observer 1) and the assistant (observer 2) with all measures being highly correlated (p<0.0001). There was no significant difference in mean pressures recorded between the two observers at any position apart from medial pressures at 45 and 90 degrees (Table 8).

TABLE 8

Interobserver Measures and Correlations at Each Flexion Angle

|  |  | 10° medial | 10° lateral | 45° medial | 45° lateral | 90° medial | 90° lateral |
|---|---|---|---|---|---|---|---|
| Mean Pressure (psi) | Observer 1 | 24.2 | 12.7 | 25.1 | 7.2 | 19.9 | 7.7 |
|  | Observer 2 | 23.2 | 12.3 | 23.1 | 7.9 | 17.6 | 8.2 |
| Range (psi) | Observer 1 | 0-132 | 0-61 | 0-154 | 0-32 | 0-85 | 0-46 |
|  | Observer 2 | 0-143 | 0-62 | 0-138 | 0-36 | 0-69 | 0-44 |
| Mean diference CI (psi) |  | −0.1-2.0 | −0.6-1.4 | 0.7-3.2 | −1.5-0.2 | 1.3-3.4 | −0.9-0.9 |
| Mean difference p value |  | 0.065 | 0.45 | 0.002* | 0.1558 | <0.0001* | 0.9872 |
| Pearson's Correlation Coefficient (R) |  | 0.97 | 0.88 | 0.94 | 0.77 | 0.91 | 0.78 |

TABLE 8-continued

| | 10° medial | 10° lateral | 45° medial | 45° lateral | 90° medial | 90° lateral |
|---|---|---|---|---|---|---|
| Pearson's Correlation CI (R) | 0.95-0.98 | 0.84-0.92 | 0.91-0.95 | 0.69-0.83 | 0.88-0.94 | 0.71-0.84 |
| Pearson's p value | <0.0001* | <0.0001* | <0.0001* | <0.0001* | <0.0001* | <0.0001* |

CI = confidence interval;
*statistically significant p values

Primary Outcome—Mean Intercompartmental Pressure Difference at 10 Degrees

Figure 8:
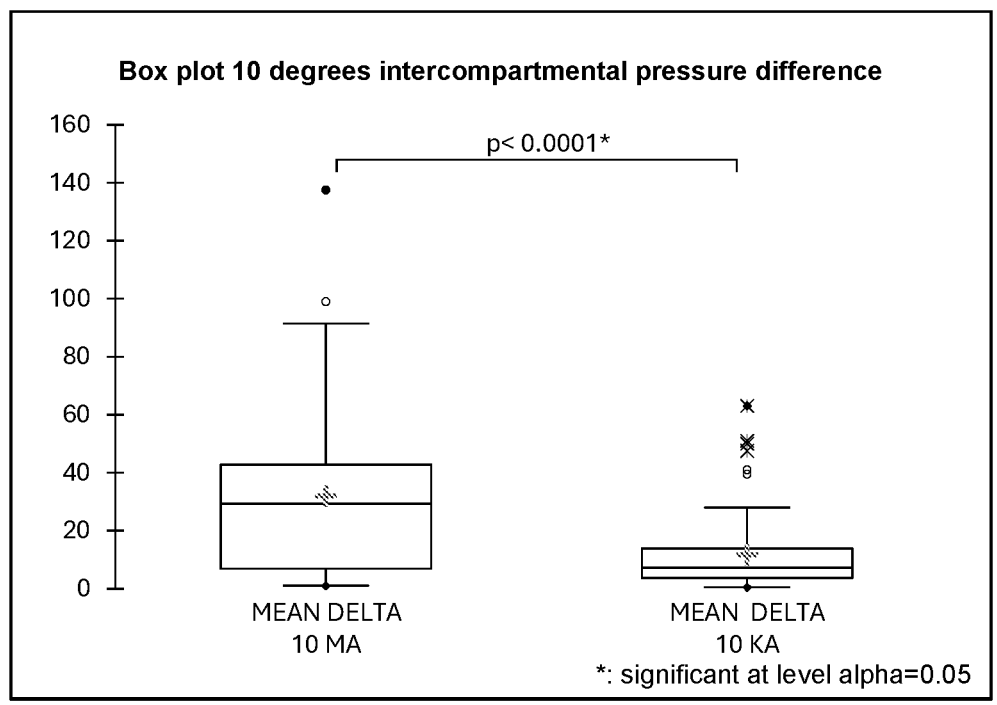
FIG. 8: Box plot mean intercompartmental pressure difference at 10 degrees. Vertical axis units pressure in psi; MA=mechanical alignment; KA=kinematic alignment.

The mean intercompartmental pressure difference at 10 degrees in the MA group was 32.0 psi (range 0-138; SD 28.9) which was unbalanced based on the sensor definition of knee balance of 0-15 psi. The mean intercompartmental pressure difference at 10 degrees in the KA group was 11.7 psi (range 0-63; SD 13.1) which was within the balanced range. The mean intercompartmental pressure difference was 20.3 psi between groups which was statistically significant (p<0.0001; Students t-test; see FIG. 8 box plot).

Intercompartmental Pressure Difference at all Knee Flexion Angles

Figure 9:
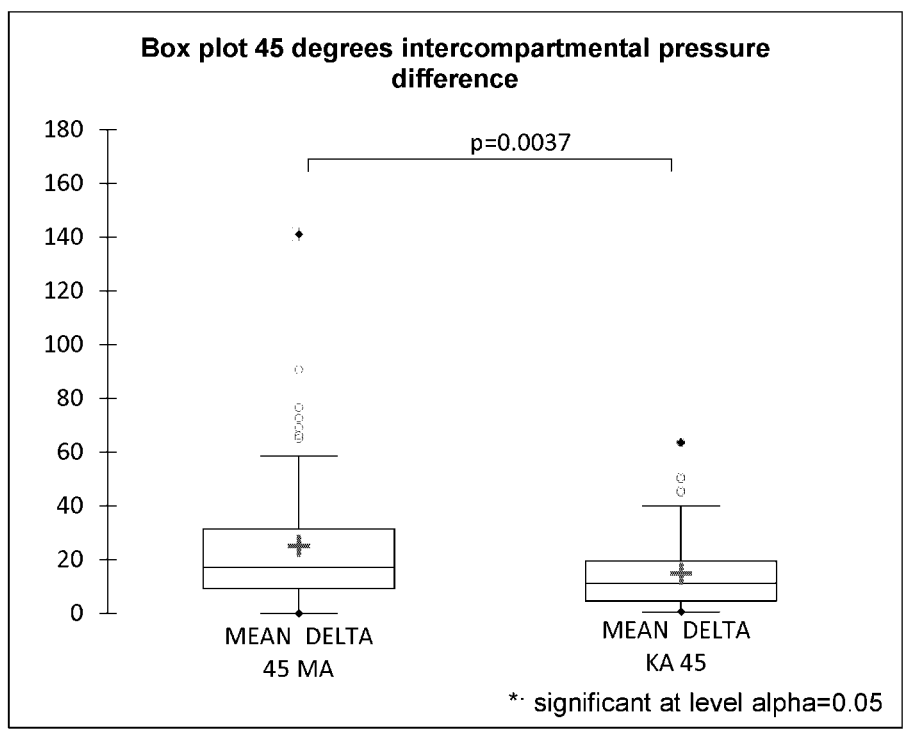
FIG. 9: Box plot of mean intercompartmental pressure difference at 45 degrees. Vertical axis units pressure in psi; MA=mechanical alignment; KA=kinematic alignment
Figure 10:
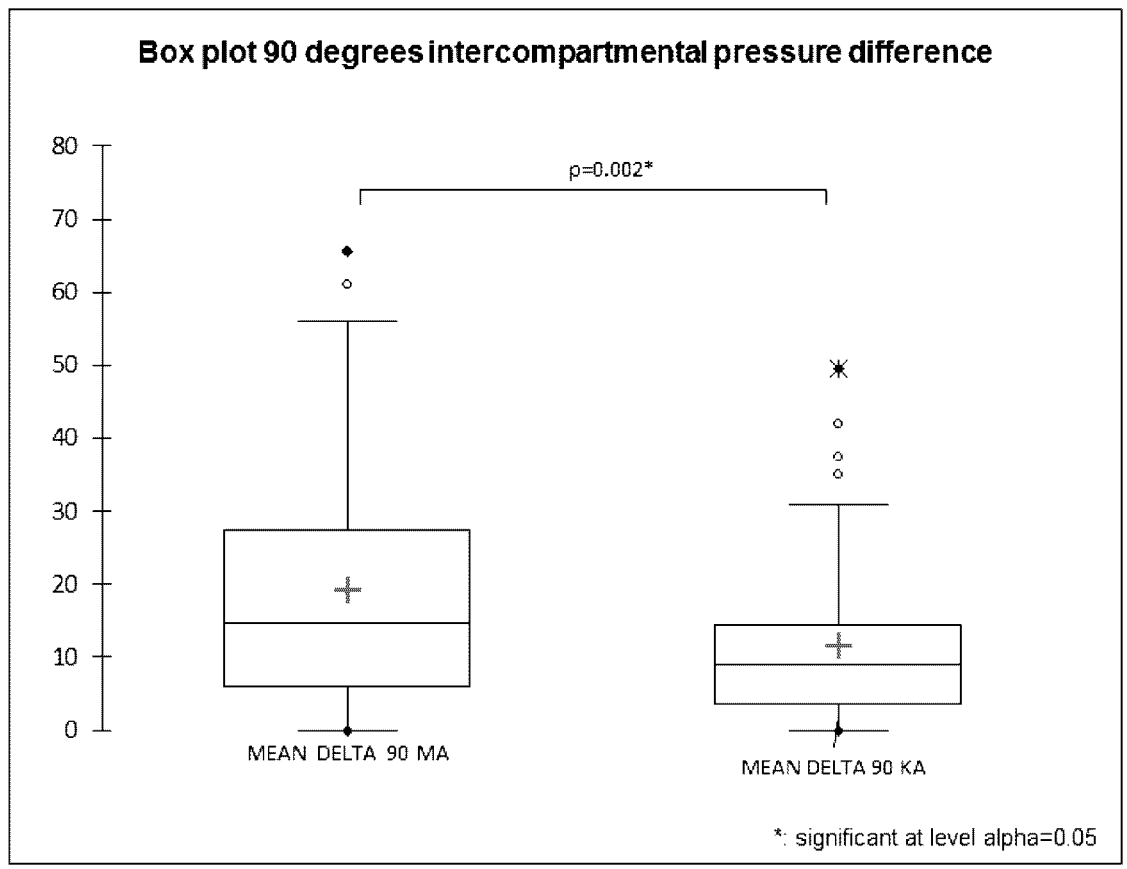
FIG. 10: Box plot of mean intercompartmental pressure difference at 90 degrees. Vertical axis units pressure in psi; MA=mechanical alignment; KA=kinematic alignment.

There was a significant difference in mean intercompartmental pressures at all flexion angles (see table 9, FIG. 9 and FIG. 10 box plots). The MA group had mean intercompartmental pressure differences that were greater than the balanced range of 15 psi at all knee flexion angles. The intercompartmental pressure difference in the KA group was within the balanced range at all knee flexion angles. Table 10 presents the mean of the compartmental pressures for observers 1 and 2 recorded at each position of knee flexion along with standard deviations and ranges.

TABLE 9

Mean intercompartmental pressure difference at all knee flexion angles.

| Mean IC pressure difference | MA (mean psi) | KA (mean psi) | Difference (mean psi) | 95% CI | p value |
|---|---|---|---|---|---|
| 10 degrees | 32.0 | 11.7 | 20.3 | 12.8-27.8 | <0.0001 |
| 45 degrees | 25.2 | 14.8 | 10.3 | 3.4-17.2 | 0.004 |
| 90 degrees | 19.1 | 11.7 | 7.4 | 2.9-12.0 | 0.002 |

IC = intercompartmental;
CI = confidence interval;
MA = mechanical alignment;
KA = kinematic alignment

TABLE 10

Mean compartmental pressures and ranges at all knee flexion angles.

| | 10° medial | 10° lateral | 45° medial | 45° lateral | 90° medial | 90° lateral |
|---|---|---|---|---|---|---|
| MA mean (SD) | 30.0 (30.7) | 13.4 (15.1) | 27.5 (25.9) | 8.6 (7.3) | 21.9 (16.2) | 8.9 (8.2) |
| MA range | 0-138 | 0-62 | 0-146 | 0-32 | 0-71 | 0-45 |
| KA mean (SD) | 17.5 (13.0) | 11.6 (9.3) | 20.8 (13.4) | 9.5 (6.9) | 15.7 (10.8) | 9.7 (6.9) |
| KA range | 0-63 | 0-50 | 0-72 | 0-32 | 0-50 | 0-32 |

SD = standard deviation;
MA = mechanical alignment;
KA = kinematic alignment

Rate of Knee Balance Between Groups

There was a higher proportion of knees that were balanced in the KA group, with 80% having optimal balance (56 of 70 knees) at 10 degrees compared to 35.3% in the MA group (24 of 68 knees). This difference was statistically significant (p<0.0001; Chi square test).

The absolute and relative risks of having an unbalanced knee at each flexion position is presented in table 11. There was a relative risk reduction of 69.1%, 26.5% and 48.4% of knee imbalance by undergoing a total knee arthroplasty with KA versus MA at 10, 45 and 90 degrees respectively.

TABLE 11

Relative Risk of Unbalanced Knee States

| | MA Absolute Risk of Being Unbalanced | KA Absolute Risk of Being Unbalanced | Absolute Risk Reduction | Relative Risk Reduction | p value (MA versus KA absolute risk) |
|---|---|---|---|---|---|
| 10 degrees | 64.7% (n = 44) | 20% (n = `14) | 44.7% | 69.1% | <0.0001 |
| 45 degrees | 54.4% (n = 37) | 40% (n = 28) | 14.4% | 26.5% | 0.09 |
| 90 degrees | 47.1% (n = 32) | 24.3% (n = 17) | 22.8% | 48.4% | 0.005 |

MA = mechanical alignment;
KA = kinematic alignment;
n = number of cases

Requirements for Subsequent Knee Balancing

There was a significantly higher requirement to perform bone recuts, both in isolation, as well as with additional soft tissue releases in the MA group to achieve optimal knee balance (table 12). A total of 48.5% of cases in the MA group required a bone recut to change the knee alignment in order to balance the knee compared to 8.6% in the KA group. Bone recuts were most often tibial based, however femoral recuts and combined femoral and tibial recuts were also required (see table 13).

TABLE 12

Requirements for knee balancing

| Knee Balancing Interventions | MA percentage (n) | KA percentage (n) | p value * |
|---|---|---|---|
| Soft tissue releases only | 14.7% (10) | 22.9% (16) | 0.2209 |
| Bone Recuts Only | 25% (17) | 1.4% (1) | <0.0001 |
| Bone Recuts with Soft Tissue Releases | 48.5% (33) | 8.6% (6) | <0.0001 |

MA = mechanical alignment;
KA = kinematic alignment;
n = number of cases;
* Chi square test

TABLE 13

Analysis of bone recuts per intervention

| | MA percentage (n) | KA percentage (n) | p value* |
|---|---|---|---|
| Tibial recut | 41.2% (28) | 5.7% (4) | <0.0001 |
| Femoral recut | 13.2% (9) | 2.9% (2) | 0.024 |
| Both tibial and femoral recut | 5.9% (4) | 0% (0) | 0.039 |
| Any bone recut | 48.5% (33) | 8.6% (6) | <0.0001 |

MA = mechanical alignment;
KA = kinematic alignment;
n = number of cases;
*Chi square test Presence of Lift Off There was a significantly higher proportion of cases with lift off in the MA group with 42.6% of knees having no contact in one compartment in at least one position compared to 12.9% in the KA group (p<0.0001; Chi square test). When comparing two or more positions of knee flexion where lift off occurred, 26.5% had lift off in the MA group compared to 4.3% in the KA group (p<0.0001; Chi square test).

Operative Time

The mean total operative time in the MA group was 77.6 minutes (SD 12.3, 58-120 minutes) and 79.2 minutes in the KA group (SD 17.0; 58-160 minutes). This difference was not statistically significant (p=0.91; Students t test).

Discussion

There is an evolving trend in total knee arthroplasty to restore the constitutional alignment of the knee as opposed to the traditional technique of mechanical alignment. The common term for this technique is kinematic alignment, with the method attempting to restore the knee alignment around its three axes of motion. The concept behind recreation of the constitutional alignment is that it will restore the pre-arthritic soft tissue tension, and in particular, the collateral ligament tension throughout the range of motion. It is then anticipated that optimization of knee balance may then improve patient perceived outcomes, as knee balance is believed to be a major surgical determinant of improved patient satisfaction. There may also be a benefit of reduced early post-operative morbidity from less soft tissue trauma to ligaments, resulting in reduced pain, bleeding and a reduced potential for iatrogenic knee ligament over-release. To date, there has been no study that has validated whether attempting to restore of the patients constitutional alignment does in fact improve soft tissue balance as well as reducing the requirements for subsequent knee balancing procedures.

The findings of this study support the primary hypothesis that recreating the constitutional alignment within a restrictive safe zone results in a knee that is more objectively more balanced at 10 degrees compared to a mechanically aligned knee with a horizontal joint line. Just over one-third of knees that were mechanically aligned were considered to be balanced at 10 degrees of knee flexion, compared to 80 percent in the kinematic group. It is possible that further improvements in knee balance in the kinematic group noted in this study would have occurred if there was wider restrictive boundaries in place. In addition, we did not exclude patients in this study based on severity of deformity, bone loss or flexion contractures, all of which may have altered the capacity to determine the constitutional alignment. We chose 10 degrees of knee flexion as the position for our primary outcome measure as it is firstly, the position at which radiographic planning is undertaken to perform a kinematic alignment surgery. Secondly, it is also the position at which weight bearing in stance phase most likely plays a role in joint kinematics and associated symptoms of joint laxity.

With regards to secondary outcomes, knee balance in the KA group was also improved at 45 and 90 degrees of flexion, with the mean intercompartmental pressure difference being within the definition of balance in all three positions. In those knees that were mechanically aligned, the knee was considered unbalanced in all three positions with the highest mean pressure differences noted at 10 degrees. In addition, we found significantly fewer requirements to alter the knee alignment in those that were kinematically aligned. However, nearly half of the mechanically aligned knees required a recut of either the tibia, femur or both bones to balance the knee. This further supports the concept that aligning the knee towards its constitutional alignment as a primary goal at surgery may more readily optimize the native soft tissue tension.

The risk of severe knee imbalance in this study was assessed via the presence of lift off. This occurs from significant over-tensioning of the collateral ligament on the contralateral side of the tibiofemoral joint separation and potentially indicates unicompartmental load bearing. Just over one-quarter of all cases that were mechanically aligned demonstrated lift off in two out of three knee flexion positions, versus less than five percent in those that were aligned kinematically. It is yet to be determined whether the increased risk of significant polyethylene wear from lift off related to unicompartmental joint loading over a smaller contact surface area in those knees that are mechanically aligned is more likely to induce premature prosthetic failure than those knees that are aligned kinematically, outside the prior safe zones of the mechanical alignment method, but with more uniform intercompartmental loading.

To date, there have been four randomized controlled trials assessing clinical differences between kinematic and mechanical alignment in total knee arthroplasty [14-16, 26], all of which have had significant methodological flaws. All four studies used patient specific instrumentation (PSI, individually produced cutting guides based on pre-operative imaging) to achieve alignment in the kinematic group. The comparator groups in three of the studies used a combination of intramedullary and extramedullary guides to achieve mechanical alignment [15, 26, 27]. Using different techniques to determine alignment makes comparisons between these techniques difficult. Only one of the studies used the current gold standard of full-optical, computer-assisted navigation in the mechanical group [16, 28]. None of these studies aimed to quantify if there was a difference in knee balance between these two techniques, particularly with the use of sensor-defined compartmental loads.

Studies on PSI in the literature have shown it to be no more accurate, and in many cases less accurate, than traditional guides in achieving soft tissue balance; surgeon-led adjustments were required in more than half of cases in some series [29-31]. A recent meta-analysis found that the use of PSI improved femoral alignment and overall limb alignment, but had higher rates of tibial component malalignment when compared to conventional instrumentation [32].

There is also significant variation in the definition of kinematic in each of these studies. Two of the studies aimed to recreate the original joint line obliquity but neutralise the HKA angle [16, 27]. Only Waterson et al. attempted to correct both the joint line and HKA to the native state [15].

Our study addressed many of these methodological issues of prior studies. Firstly, both groups were surgically aligned using optical navigation as it has been shown to have higher accuracy than other alignment techniques [28, 33]. In addition, we wanted to ensure that the same alignment technique was used in both arms of the trial. Secondly, we chose not only to recreate the HKA angle but also aim to reproduce the joint line obliquity. Thirdly, we used a quantitative outcome measure with sensor monitoring to determine whether knee balance had been restored as the primary outcome to reduce the risk of measurement bias. High interobserver correlations were noted in sensor measures. The sensors also allow the extensor mechanism to be reduced whilst analyzing knee balance. A study by Schnaser and co-authors found that a lateralized extensor mechanism artificially increases lateral compartmental loads compared to when it is reduced and closure is simulated with towel clips using sensor defined compartmental pressure monitoring [23]. In addition, a recent publication from our group found that surgeon defined assessment of knee balance was a poor predictor of knee balance, particularly as knee flexion angles increase [34].

There has been some recent work highlighting the impact of soft tissue balancing on patient satisfaction after TKA. In 2014, Gustke published 2-year follow-up data comparing patient reported outcome measures from a group of TKAs that were determined to be balanced based on intra-operative sensor data and a group that were unbalanced. The unbalanced group had a satisfaction rate of 82.1%, while 96.7% of those that were balanced were satisfied or very satisfied [18].

A study by Meneghini and colleagues retrospectively assessed intercompartmental pressures with sensors following manual ligament balancing in TKA [19]. Only 15% of knees were considered balanced within the defined 15 psi mediolateral difference. A further 57% had an intercompartmental pressure difference of between 15.1 and 75 psi, and a further 28% had a pressure difference greater than 75 psi. The authors found at 4 months, a greater improvement in University of California Los Angeles scores for those knees with pressure differences under 60 psi. No other correlation was noted between compartmental pressures and Knee Society objective, function or satisfaction scores or quality of life measures.

This study has several limitations. Firstly, after determination of knee balance using sensor data, both groups then underwent knee balancing if indicated to achieve a pressure differential of 15 psi or less between compartments. We did this as we felt it was inappropriate to leave a knee unbalanced once sensor data confirmed this. As such, we are unable compare the long-term outcomes of knees aligned with either method as nearly half of all knees mechanically aligned subsequently underwent bone recuts that most likely aligned them closer to their constitutional alignment. However, we aim to report on the clinical outcomes at a minimum of one year to determine if there is any patient perceived differences in knees that are primarily kinematically aligned versus those that are primarily mechanically aligned, with secondary knee balancing when indicated. Although this will inform surgical practice on accepted methods to achieve a balanced knee, it will not determine if either alignment technique without the use of sensors is superior. Secondly, there is still a paucity of evidence on what intercompartmental pressure difference range correlates to improved patient outcomes. Lastly, the costs of using sensor technology to determine and subsequently undertake knee balancing may be prohibitive to its wide spread use. However, for the purposes of this study, it provided an objective measure of knee balance.

The results of this study confirm that attempts to restore the patient's constitutional alignment improves knee balance when compared to traditional mechanical alignment. Kinematic alignment TKA performed within a restrictive safe zone also reduced the requirements for further knee balancing as well as the risk of significant knee imbalance. The clinical and functional outcomes of these new strategies require further high-quality randomized trials and long-term follow-up to evaluate efficacy, safety and revision risk associated with this technique.

Conclusion

Recreation of the patient's constitutional alignment resulted in a balanced knee more readily than when mechanical alignment was undertaken in total knee arthroplasty. The requirement for subsequent knee balancing, particularly with use of bone recuts was significantly reduced when kinematic techniques were undertaken within a restrictive safe zone. The rate of significant knee imbalance, particularly with lift off was higher in those knees that were mechanically aligned.

REFERENCES

1. Ali, A., et al., *Dissatisfied patients after total knee arthroplasty: a registry study involving 114 patients with 8-13 years of followup*. Acta Orthop, 2014. 85(3): p. 229-33.
2. Choi, Y. J. and H. J. Ra, *Patient Satisfaction after Total Knee Arthroplasty*. Knee Surg Relat Res, 2016. 28(1): p. 1-15.
3. Williams, D. P., et al., *Early postoperative predictors of satisfaction following total knee arthroplasty*. Knee, 2013. 20(6): p. 442-6.
4. ACORN, A.C.O.R. *ACORN Annual Report, 2015*. 2015 2015; Available from: http://www/acornregistry.org/images/ACORN_AnnualReport_2015.pdf.
5. Dunbar, M. J., G. Richardson, and O. Robertsson, *I can't get no satisfaction after my total knee replacement: rhymes and reasons*. Bone Joint J, 2013. 95-b(11 Suppl A): p. 148-52.
6. Sakellariou, V. I., et al., *Risk Assessment for Chronic Pain and Patient Satisfaction After Total Knee Arthroplasty*. Orthopedics, 2016. 39(1): p. 55-62.
7. Nam, D., R. M. Nunley, and R. L. Barrack, *Patient dissatisfaction following total knee replacement: a growing concern?* Bone Joint J, 2014. 96-B(11 Supple A): p. 96-100.

8. Scott, C. E., et al., *Predicting dissatisfaction following total knee arthroplasty in patients under 55 years of age.* Bone Joint J, 2016. 98-B(12): p. 1625-1634.
9. Schulze, A. and H. P. Scharf, *[Satisfaction after total knee arthroplasty. Comparison of 1990-1999 with 2000-2012].* Orthopade, 2013. 42(10): p. 858-65.
10. Howell, S. M., et al., *Does a kinematically aligned total knee arthroplasty restore function without failure regardless of alignment category?* Clin Orthop Relat Res, 2013. 471(3): p. 1000-7.
11. Bellemans, J., et al., *The Chitranjan Ranawat award: is neutral mechanical alignment normal for all patients? The concept of constitutional varus.* Clin Orthop Relat Res, 2012. 470(1): p. 45-53.
12. Lee, Y. S., et al., *Kinematic alignment is a possible alternative to mechanical alignment in total knee arthroplasty.* Knee Surg Sports Traumatol Arthrosc, 2017. 25(11): p. 3467-3479.
13. Calliess, T., et al., *PSI kinematic versus non-PSI mechanical alignment in total knee arthroplasty: a prospective, randomized study.* Knee Surgery, Sports Traumatology, Arthroscopy, 2017. 25(6): p. 1743-1748.
14. Dossett, H. G., et al., *A randomised controlled trial of kinematically and mechanically aligned total knee replacements: two-year clinical results.* Bone Joint J, 2014. 96-B(7): p. 907-13.
15. Waterson, H. B., et al., *The early outcome of kinematic versus mechanical alignment in total knee arthroplasty: a prospective randomised control trial.* Bone Joint J, 2016. 98-b(10): p. 1360-1368.
16. Young, S. W., et al., *The Chitranjan S. Ranawat Award: No Difference in 2-year Functional Outcomes Using Kinematic versus Mechanical Alignment in TKA: A Randomized Controlled Clinical Trial.* Clin Orthop Relat Res, 2017. 475(1): p. 9-20.
17. Gustke, K. A., et al., *A new method for defining balance: promising short-term clinical outcomes of sensor-guided TKA.* J Arthroplasty, 2014. 29(5): p. 955-60.
18. Gustke, K. A., et al., *Increased satisfaction after total knee replacement using sensor-guided technology.* Bone Joint J, 2014. 96-b(10): p. 1333-8.
19. Meneghini, R. M., et al., *Can Intraoperative Sensors Determine the "Target" Ligament Balance? Early Outcomes in Total Knee Arthroplasty.* J Arthroplasty, 2016. 31(10): p. 2181-7.
20. Paley, D., *Principles of Deformity Correction.* 2003, Heidelberg, Germany: Springer-Verlag.
21. Parratte, S., et al., *Effect of postoperative mechanical axis alignment on the fifteen-year survival of modern, cemented total knee replacements.* J Bone Joint Surg Am, 2010. 92(12): p. 2143-9.
22. Ritter, M. A., et al., *Postoperative alignment of total knee replacement. Its effect on survival.* Clin Orthop Relat Res, 1994(299): p. 153-6.
23. Schnaser, E., et al., *The Position of the Patella and Extensor Mechanism Affects Intraoperative Compartmental Loads During Total Knee Arthroplasty: A Pilot Study Using Intraoperative Sensing to Guide Soft Tissue Balance.* J Arthroplasty, 2015. 30(8): p. 1348-53 e3.
24. Chauhan, S. K., et al., *Computer-assisted total knee replacement. A controlled cadaver study using a multi-parameter quantitative CT assessment of alignment (the Perth CT Protocol).* J Bone Joint Surg Br, 2004. 86(6): p. 818-23.
25. Sikorski, J. M., *Alignment in total knee replacement.* J Bone Joint Surg Br, 2008. 90(9): p. 1121-7.
26. Calliess, T., et al., *PSI kinematic versus non-PSI mechanical alignment in total knee arthroplasty: a prospective, randomized study.* Knee Surg Sports Traumatol Arthrosc, 2017. 25(6): p. 1743-1748.
27. Dossett, H. G., et al., *Kinematically versus mechanically aligned total knee arthroplasty.* Orthopedics, 2012. 35(2): p. e160-9.
28. Hetaimish, B. M., et al., *Meta-analysis of navigation vs conventional total knee arthroplasty.* J Arthroplasty, 2012. 27(6): p. 1177-82.
29. Chareancholvanich, K., R. Narkbunnam, and C. Pornrattanamaneewong, *A prospective randomised controlled study of patient-specific cutting guides compared with conventional instrumentation in total knee replacement.* Bone Joint J, 2013. 95-B(3): p. 354-9.
30. Victor, J., et al., *Patient-specific guides do not improve accuracy in total knee arthroplasty: a prospective randomized controlled trial.* Clin Orthop Relat Res, 2014. 472(1): p. 263-71.
31. Stronach, B. M., et al., *Patient-specific total knee arthroplasty required frequent surgeon-directed changes.* Clin Orthop Relat Res, 2013. 471(1): p. 169-74.
32. Thienpont, E., P. E. Schwab, and P. Fennema, *Efficacy of Patient-Specific Instruments in Total Knee Arthroplasty: A Systematic Review and Meta-Analysis.* J Bone Joint Surg Am, 2017. 99(6): p. 521-530.
33. Mason, J. B., et al., *Meta-analysis of alignment outcomes in computer-assisted total knee arthroplasty surgery.* J Arthroplasty, 2007. 22(8): p. 1097-106.
34. MacDessi, S. J., M. A. Gharaibeh, and I. A. Harris, *How Accurately Can Soft Tissue Balance Be Determined in Total Knee Arthroplasty?* The Journal of Arthroplasty, 2018.

Example 4

A Novel Classification System for the Coronal Plane Alignment of the Knee—its Use in Healthy and Arthritic Patients Introduction The standard technique in total knee arthroplasty requires tibial and femoral cuts perpendicular to the mechanical axis of the limb. Component design has been based around this philosophy with compensatory external rotation of the femoral component to achieve equal flexion and extension gaps. The aims of this method are to create a horizontal joint line and a neutral mechanical axis which is believed to provide the best mechanical environment for the longevity of the prosthesis. This long-established gold standard technique has remained largely unchanged for the last 30 years. During this time, there has been a steady evolution in prosthesis design and the survivorship of the implants has improved significantly. Latest registry data suggests an <10% revision rate at 20 years. Over the same period the patient reported outcomes have not benefited from the same improvements, with up to 15% of patients remaining dissatisfied with their outcome.

Improvements in survivorship without corresponding improvements in outcomes has led some to suggest a shift in technique favoring recreation of the patient's own constitutional alignment. This is potentially at the expense of providing the ideal mechanical environment for the prosthesis. This commonly described as kinematic alignment by Howell et al.

The term "kinematic" has grown in popularity since it was first described. Howell et al. described a method to recreate the constitutional knee joint by recreating the movement around three axes that make up normal knee motion. A transverse axis in the femur about which the tibia flexes and extends; a transverse axis in the femur about which the patella moves; and a longitudinal axis in the tibia about which the tibia internally and externally rotates on the femur. Whilst this original description represents a theoretical ideal goal, the feasibility of achieving this with modern implants and techniques is somewhat unclear. Since its initial description, methods based on these original goals have gained popularity amongst arthroplasty surgeons without any high quality evidence to support them. In the existing literature, there is a great deal of ambiguity about the different aspects of kinematic alignment being pursued and the methods described to do so.

The purpose of the present Example is to propose a classification system for the coronal plane alignment of the knee (CPAK). This classification combines the previously described arithmetic HKA that estimates the pre-disease alignment of the limb, along with the joint line angle as a separate variable using new nomenclature for its estimation. The classification system aims to remove some of the confusion surrounding current terminology, as well as providing a framework for future research evaluating these techniques. We aim provide descriptive analyses and comparative measures using radiographic observational datasets of healthy volunteers and arthritic subjects undergoing total knee arthroplasty.

This has been validated using long leg alignment films of 500 knees from healthy volunteers as well as 500 consecutive arthritic patients undergoing total knee arthroplasty.

Methods

There have been several techniques described that attempt to measure the native joint line of an arthritic patient prior to arthroplasty surgery. Many of these involve complex algorithms based around clinically unindicated 3-dimensional imaging and as such this restricts their universal application. The goal of our new classification system was that it be based on the readily available gold standard for assessing the alignment of the lower limb, the weight bearing long leg alignment x-ray.

When purely considering alignment in the coronal plane, methods claiming to produce 'kinematic' alignment should recreate not just the constitutional alignment of the limb but also the native joint line obliquity.

With the unicompartmental joint space narrowing that commonly occurs as part of the arthritic process the alignment of the limb changes significantly throughout the disease process. By using bone as a surrogate for cartilage, the pre-disease alignment of the limb can be approximated until the point of significant bone loss by using the Medial Tibial Plateau Angle (MTPA) as well as the mechanical Lateral Distal Femoral Angle (mLDFA). Previous work by this group has shown that this arithmetic HKA (aHKA) is a strong indicator of pre-disease alignment. Calculation of aHKA is shown in FIG. 2.

Figure 13:
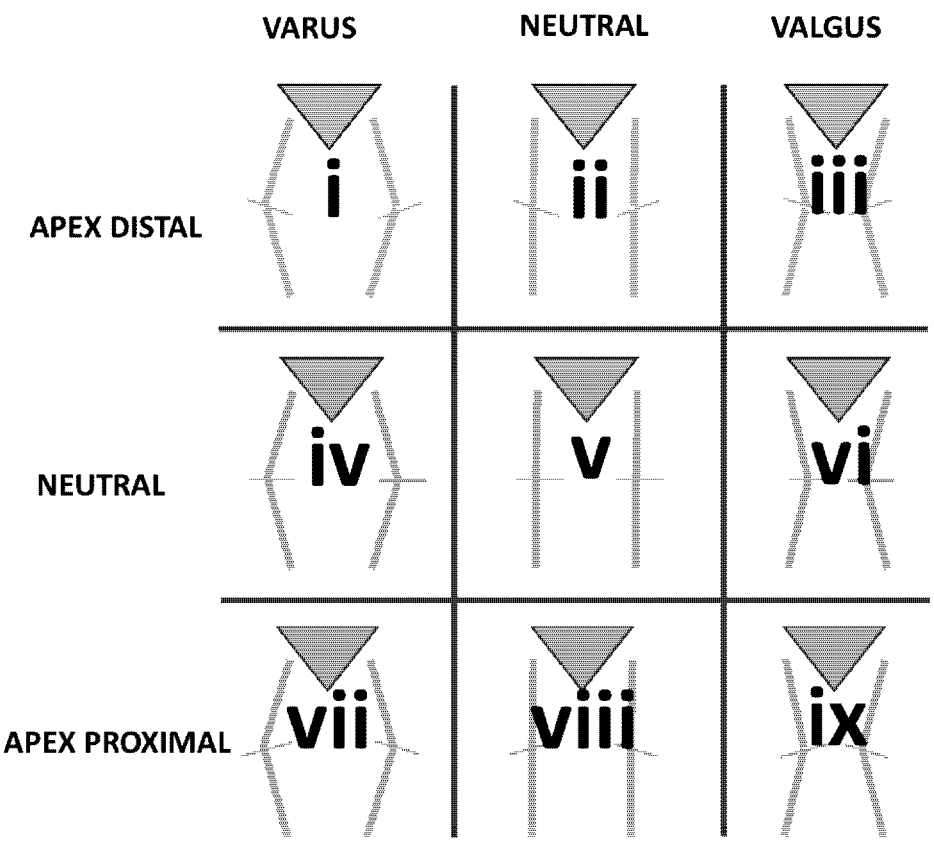
FIG. 13: Coronal Plane Alignment of the Knee classification (CPAK). 9 theoretical types of knee.

These two independent variables mean that in theory there are 9 different types of knees. See FIG. 13.

Figure 12:
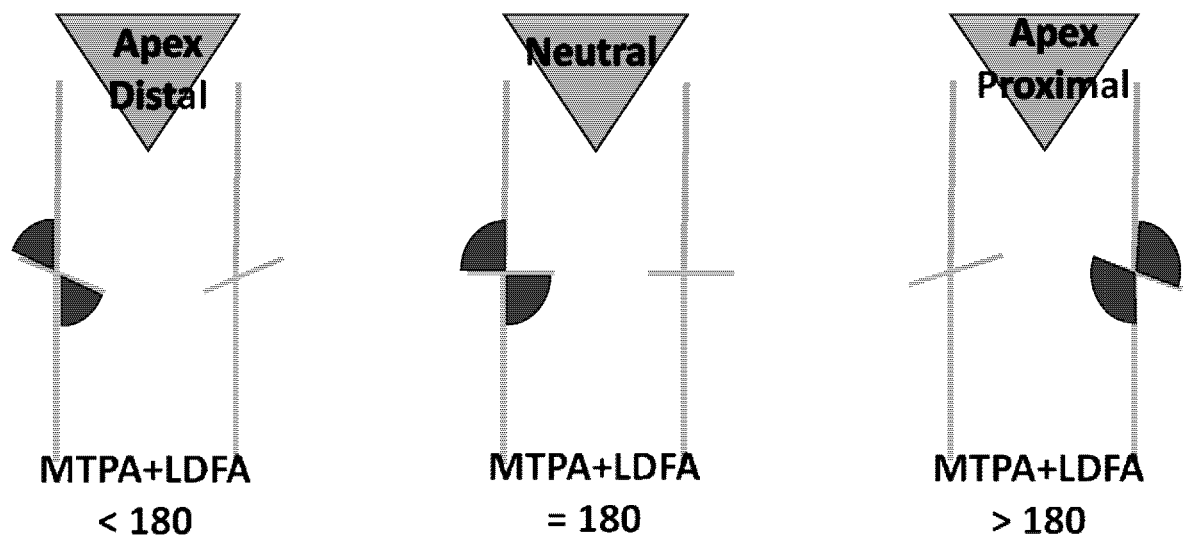
FIG. 12: Use of MTPA and LDFA to indicate joint line obliquity.

The nomenclature of joint line obliquity is another potential source of confusion. The joint line commonly referred to as varus is actually the product of tibial varus and femoral valgus in the neutrally aligned lower limb. For this reason, we prefer the terms of apex distal, neutral or apex proximal when describing the joint line. This describes whether the apex of the joint lines of both knees when extended to the midline is either below, level with or above the level of the joint. This is illustrated in FIG. 12.

An indication of joint line obliquity can also be provided by the measurement of the MTPA and the mLDFA. If the sum of these two angles is 180 then the joint line is neutral. A sum >180 indicates an apex proximal joint line and <180 indicates that the joint line is apex distal. See FIG. 12.

Patient Groups

The asymptomatic population used in this comparison were 250 young healthy adults aged between 20 and 27 used in a previous cross sectional prevalence study by one of the authors (JB) (1). These participants were recruited in a European country at high school and university campuses as well as movie theatres and job recruitment bureaus between October 2009 and March 2010. Fifty percent of the volunteers were female. Only healthy volunteers with no history of orthopaedic injury or disease were asked to participate. Both limbs were imaged and included in this population to give data from 500 knees.

The arthritic population consisted of 500 consecutive patients presenting for TKA by two of the authors (SJM, DBC) at a private hospital in New South Wales, Australia, between October 2016 and March 2018. These patients were aged between 44 and 88 years with a mean age of 66 years. 62% of patients in this group were female. Patients were included regardless of their underlying diagnosis and any previous history of surgery or trauma. To give a matched sample size to the asymptomatic population, only the limbs undergoing surgery were included to give data from 500 knees.

Radiographic Measurements

All of the healthy volunteers underwent full-leg standing digital radiography using the technique described by Paley (6). The volunteers stood barefoot in the "stand at attention" position with the feet together and the patellae orientated forward. The x-ray beam was centred on the knee with the tube at a distance of 305 cm. Three 350×430 mm cassettes were placed immediately behind the subject and the AGFA MIMOSA VIPS 1.3.00 software package (Agfa-Gevaert, Mortsol, Belgium) was used for digital stitching. A setting of 500 mA and a kilovoltage of 75 kV were used as the standard and individually adapted where necessary. The whole pelvis was included in the radiographs.

The arthritic patients underwent full-leg standing radiography as part of their routine pre-operative work-up. The x-rays were performed in a single radiology department using the same patient positioning technique as described above Classification Boundaries In order to classify the joints by type, boundaries need to be set for the definition of each variable. Type 5 represents neutral alignment and neutral joint line, the aim for a mechanical TKA. We have neutral alignment as an aHKA of 0 degrees +/−2 degrees. We have selected 2 degrees as this is the standard deviation of the aHKA data from the surveyed healthy population. A neutral joint line is defined as 180 degrees +/−3 degrees. 3 degrees is the standard deviation of the calculated joint line data from the surveyed healthy population. Using these parameters, graphs plotting aHKA against joint line allow visualization of the classification within the 9 CPAK types.

Results

Figure 14:
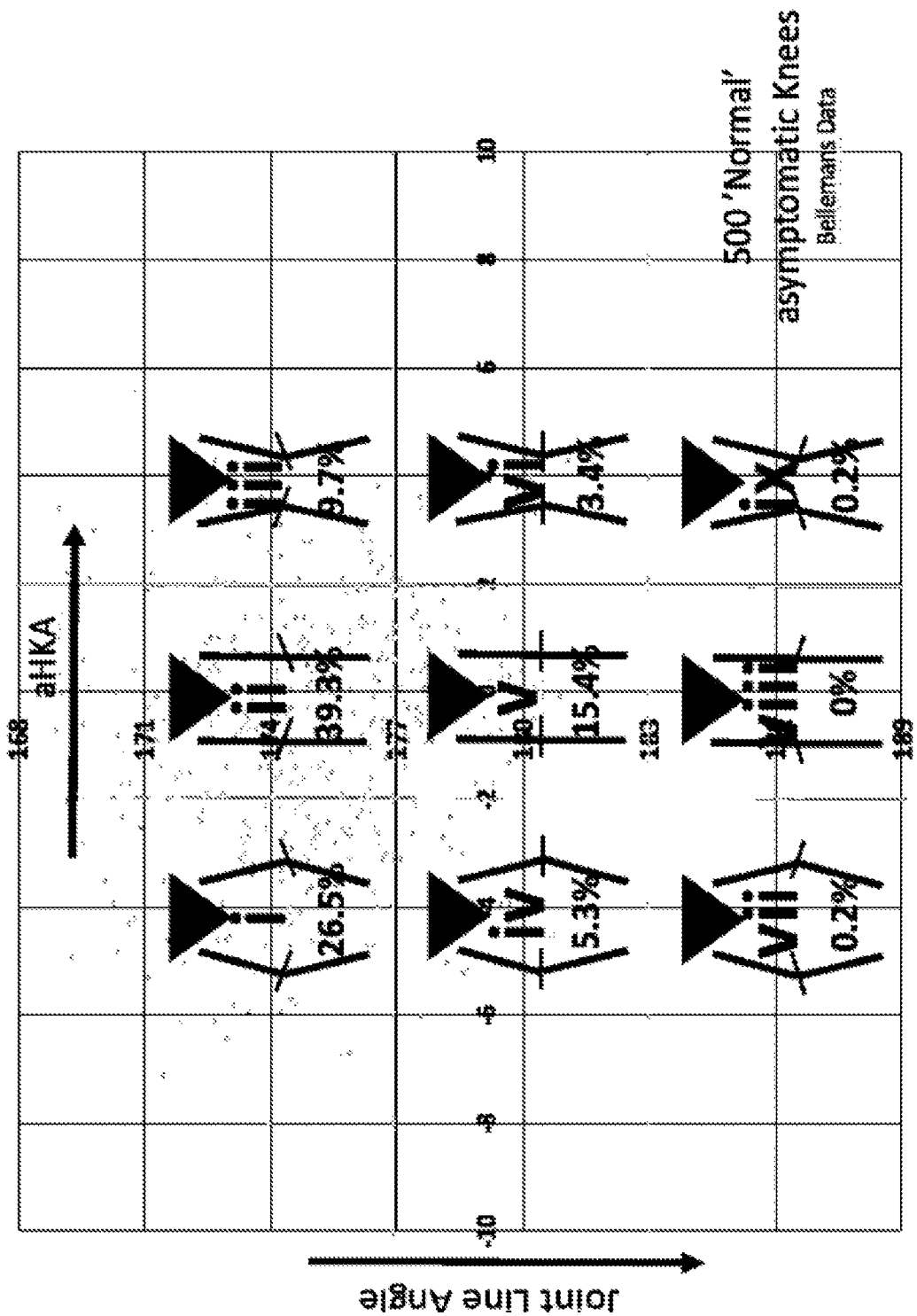
FIG. 14: Plot of aHKA against Joint Line Angle for a healthy population s. Showing distribution by percentage of the 9 CPAK types.
Figure 15:
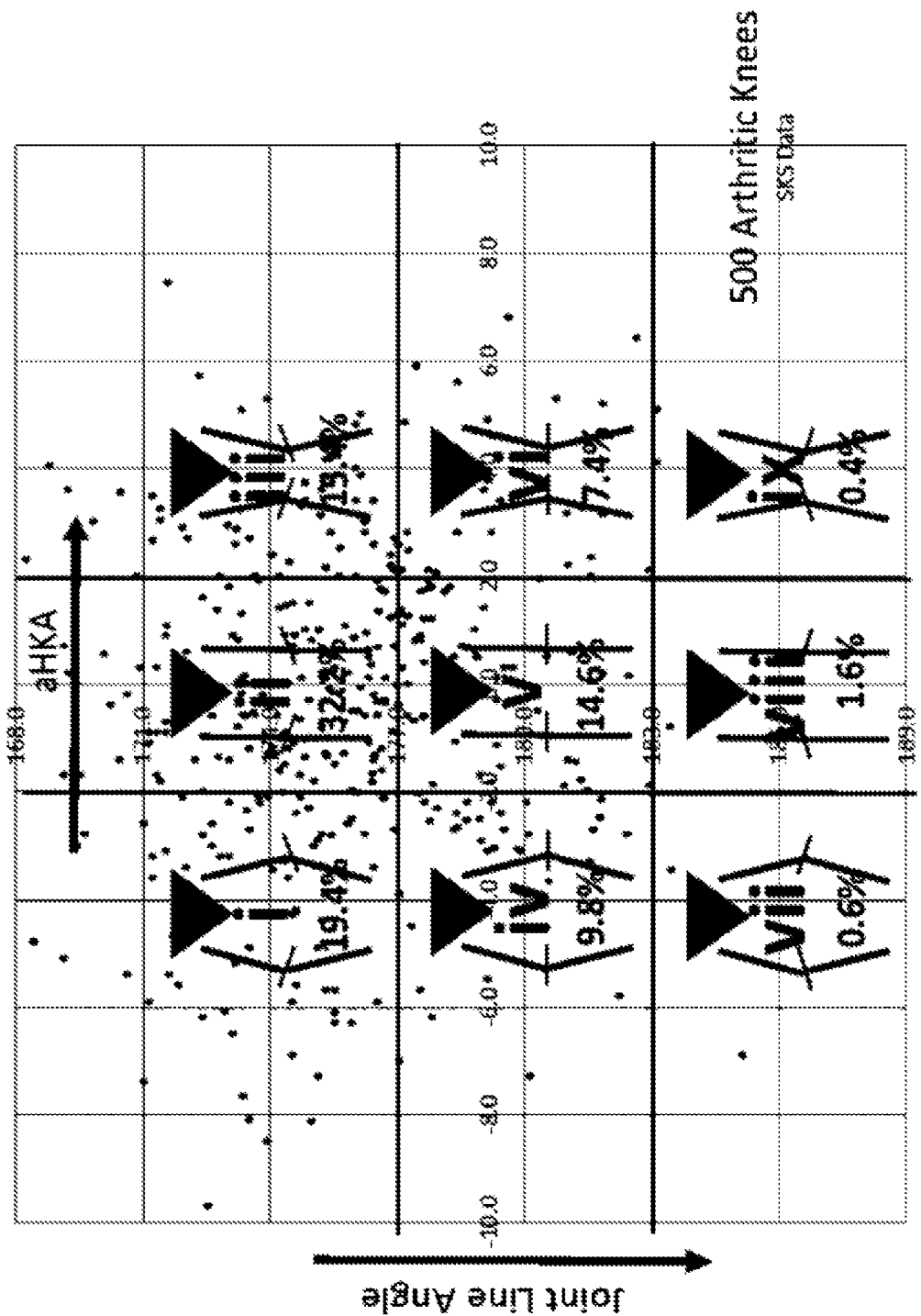
FIG. 15: Plot of aHKA against Joint Line Angle for an arthritic population s. Showing distribution by percentage of the 9 CPAK types.

These graphs show similar distributions by CPAK type for both the arthritic and healthy populations. FIGS. 14 and 15.

Discussion

The language surrounding the concept of kinematic alignment is confusing. One of the senior authors previously introduced the concept of constitutional varus. This group further developed this work to establish the role of arithmetic HKA (aHKA) in establishing an arthritic individual's constitutional alignment. We have now further classified these patients based not only on their pre-arthritic limb alignment but also their joint line.

Despite the aim of a neutral mechanical axis and horizontal joint line in conventional TKA techniques, the graphs demonstrate that only 13.8% of the healthy population and 10.2% of the arthritic population fall within this CPAK type 5. The distribution by CPAK type shows that over 70% of both groups have an apex distal joint line and over ⅓ of patients in both groups have varus alignment of the limb. This challenges the philosophy that aligning the knee in to a neutral mechanical alignment, along with a neutral joint line perpendicular to this weight bearing axis, is unlikely to restore the joint to its constitutional alignment.

The potential advantage of classifying knees in this manner is that it allows surgeons to conceptualise knees in to different alignment patterns. The classification allows determination of behave with regards to soft tissue and also to predict the capacity to achieve a balanced knee state with either mechanical or kinematic alignment techniques.

We believe that the CPAK classification system provides a simple and reproducible method for estimating the pre-disease alignment and joint line angle of the arthritic knee. The classification system can provide a clear and unique language for use when discussing kinematic alignment of the knee and as such could add value to future research performed on the topic.

Example 5

Coronal Plane Alignment of the Knee (CPAK) Classification: Prediction of Likelihood of Soft Tissue Balance in Total Knee Arthroplasty Introduction The Coronal Plane Alignment of the Knee (CPAK) Classification has been described in our previous study. It categories knees in to nine types, based on their arithmetic hip-knee-ankle (aHKA) angle and the joint line angle (JLA). In this paper, we noted a similar distribution of healthy knees and arthritic knees in a comparative analysis of 1000 knee radiographs.

In addition, we undertook a randomised controlled trial comparing knee balance by restoring the constitutional alignment within a restrictive safe zone to mechanically aligned total knee arthroplasties in 138 knees. The CPAK on-line calculator was used to determine the coronal plane resection angles and also to classify each knee in to their CPAK type. All knee surgeries were performed using computer-assisted optical navigation to ensure accuracy of surgical resections. Knee balance was determined using a wireless pressure sensor insert that has been validated in clinical studies to correlate with clinical outcomes. The primary outcome of balance was intercompartmental pressure difference of 15 psi or less between lateral and medial compartments at 10 degrees of knee flexion. The study found a significantly lower mean intercompartmental pressure difference in the kinematic alignment group compared to mechanical group at 10° of knee flexion (11.7 versus 32.0 psi; p<0.0001). In addition, the MA group had mean intercompartmental pressure differences that were greater than the balanced target of 15 psi compared to the KA group was within the balanced range (25.2 versus 14.8 psi at 45°, p=0.004; 19.1 vs 11.7 psi at 90°, p=002). Patients assigned to the KA group were significantly more likely to have a balanced knee than those in the MA group (80% versus 35.3%; p<0.0001).

The aim of this study is analyse the likelihood of achieving knee balance based on CPAK type. The purpose of this study is to enable surgeons to have a likelihood prediction based on CPAK type of achieving knee balance, by comparing the knee surgery being performed using the CPAK resection calculations or using mechanical alignment.

Methods and Analysis

Study Design

We conducted a randomised controlled, parallel-group superiority trial comparing intra-operative soft tissue balance in TKAs implanted to restore the Kinematic Alignment (KA) as the intervention group versus those aligned by traditional Mechanical Alignment (MA) as the control group. The major findings of this study have been described in a previous publication. The data from this initial study was used in this analysis to determine the likelihood of achieving knee balance based on CPAK type, comparing KA using the CPAK calculator to MA.

Intervention (KA) Group

In the KA group, the surgeon performed the initial bony resections according to the CPAK surgical plan that was defined prior to randomisation. This plan included an aim for femoral and tibial component position relative to the mechanical axis of the bones. These resections were guided and validated by the computer navigation system to ensure maximum accuracy. The rest of the procedure was completed as per the surgical technique described above.

Control (MA) Group

The surgeon performed the initial bony resections using the same computer navigation system aiming for tibial and femoral component position perpendicular to the mechanical axis of the bone and an overall HKA of 0 degrees. These resections were validated using the same computer navigation equipment to ensure maximum accuracy. The rest of the procedure was completed as per the surgical technique described above.

Inclusion Criteria

1. Patients who meet the indications for primary unilateral or bilateral total knee arthroplasty using the Smith & Nephew Legion™ posterior-stabilised total knee arthroplasty system.

2. Patients diagnosed with one or more of the following conditions:
   Osteoarthritis
   Rheumatoid inflammatory arthritis
   Post-traumatic osteoarthritis Exclusion Criteria 1. Revision TKA
2. Prior Grade 3 ligamentous knee injury to posterolateral corner (PLC) or lateral collateral ligament (LCL). Grade 3 medial collateral ligament (MCL) injuries treated conservatively may be included so long as they were deemed by the surgeon to have healed with a maximum of Grade 1 laxity.
3. Prior femoral, tibial or patellofemoral osteotomies
4. Extra-articular femoral or tibial malunion with deformity greater than 5 degrees in any plane
5. Ipsilateral foot/ankle or hip arthritis
6. Patients who are unable to provide consent or fulfil the study requirements due to cognitive incapacity or English-language deficiency Allocation A 1:1 randomisation scheme was generated using the computerised program at Randomization.com (http://www.randomization.com). To avoid unequal numbers of participants in each group, permuted blocks were used, with a block size of 4 and 33 blocks allowing for randomisation of a potential 132 subjects.

Pre-Operative Templating

Prior to the date of surgery, all patients underwent weight-bearing, long leg alignment radiographs. These were taken using the technique described by Paley [1]. Pre-operative Hip Knee Ankle (HKA) angle, Medial Proximal Tibial Angle (MPTA) and Lateral Distal Femoral Angle (LDFA) were measured for the operative knee using techniques described by Bellemans [2].

Figure 22:
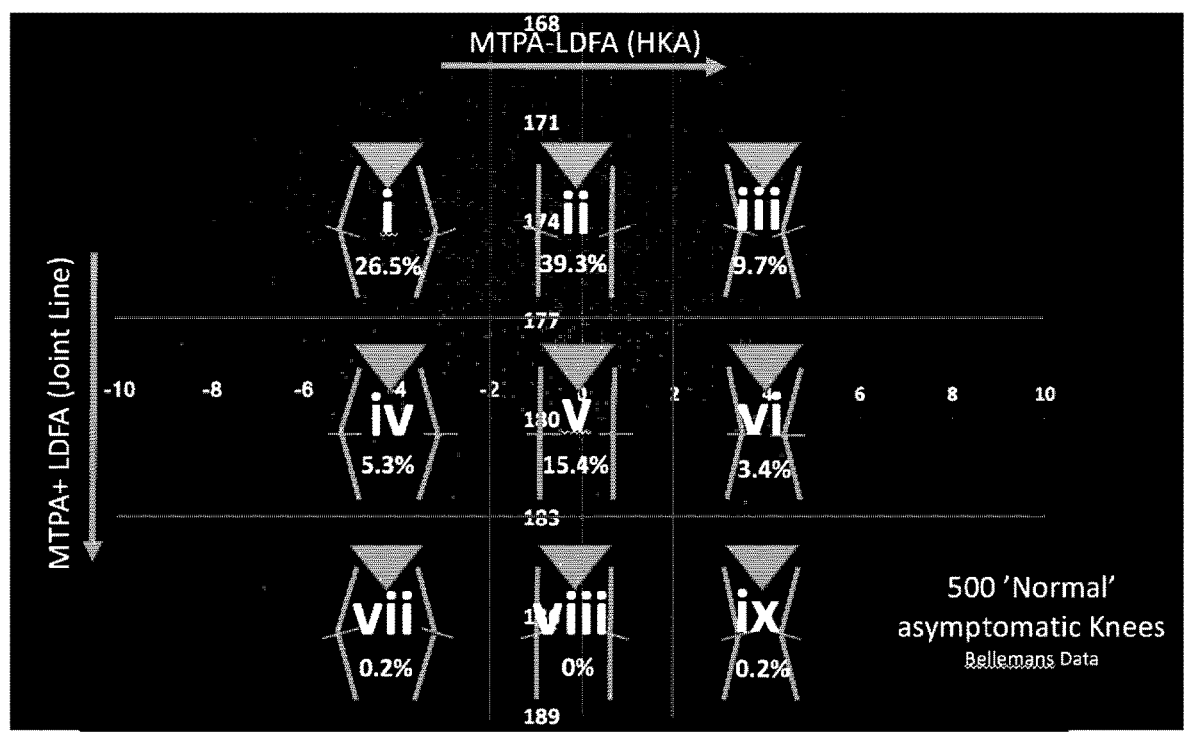
FIG. 22: CPAK classification with distribution of normal volunteers.

In order to define the kinematic alignment of each knee, we propose the Coronal Plane Alignment of the Knee (CPAK) classification so as to allow mapping of each patients' pre-disease alignment and the obliquity of their joint line using two frequently performed radiographic measurements (FIG. 22). Using Bellemans' original dataset, we can see that neutral mechanical axis of the limb with a horizontal joint line (CPAK Type V—FIG. 22) only occurs in 15% of healthy volunteers, despite this being the goal of traditional knee arthroplasty. A pre-operative plan was formulated based on these measurements for re-creation of the coronal plane alignment within a predetermined 'safe zone'.

This 'safe zone' for this study is defined as 86 to 93 degrees for recreation of both the LDFA and the MPTA and −5 degrees to +4 degrees for the HKA. The authors set the parameters of the 'safe zone' centred on the means from Bellemans' paper describing the normal distribution of these angles [11] and also based on studies comparing analysis of alignment against survivorship by Parratte [3] and Ritter [4]. It was felt by the senior knee arthroplasty authors (SJM, DBC) that this safe zone would allow 72% of patients in the KA group to have their constitutional alignment restored according to the data from Bellemans et al., whilst minimising risk of significant component malalignment that would increase the risk of implant failure. It has also been the experience of our group that errors of up to 1 degree commonly occur in individual implant positioning with the use optical navigation. This could result in undesirable alignment errors of up to +/−5 degrees for implant positioning, and up to +/−6 degrees for HKA.

The pre-operative plan involved defining the proximal tibial resection angle and distal femoral resection angles using the LDFA and MPTA measured from the pre-operative films. The resection angle were set to the nearest whole degree if this falls within the range of 86 to 93 degrees. If it falls outside of this range then it will be set to either 86 to 93 degrees, depending on which end of the safe zone is closer. If the pre-operative plan requires LDFA and MPTA resections that would lead to a HKA greater than 4 degrees, then the LDFA and MPTA were adjusted so the total HKA does not exceed the safe zone threshold. In order to reduce the risk of implant subsidence or loosening in the presence of osteoporotic bone, patients with a documented history of osteoporosis requiring bone anti-resorptive therapies, patients with documented insufficiency fractures or patients greater than 80 years of age had resection angle range for LFDA and MPTA narrowed to 87 to 93 degrees.

Figure 16:
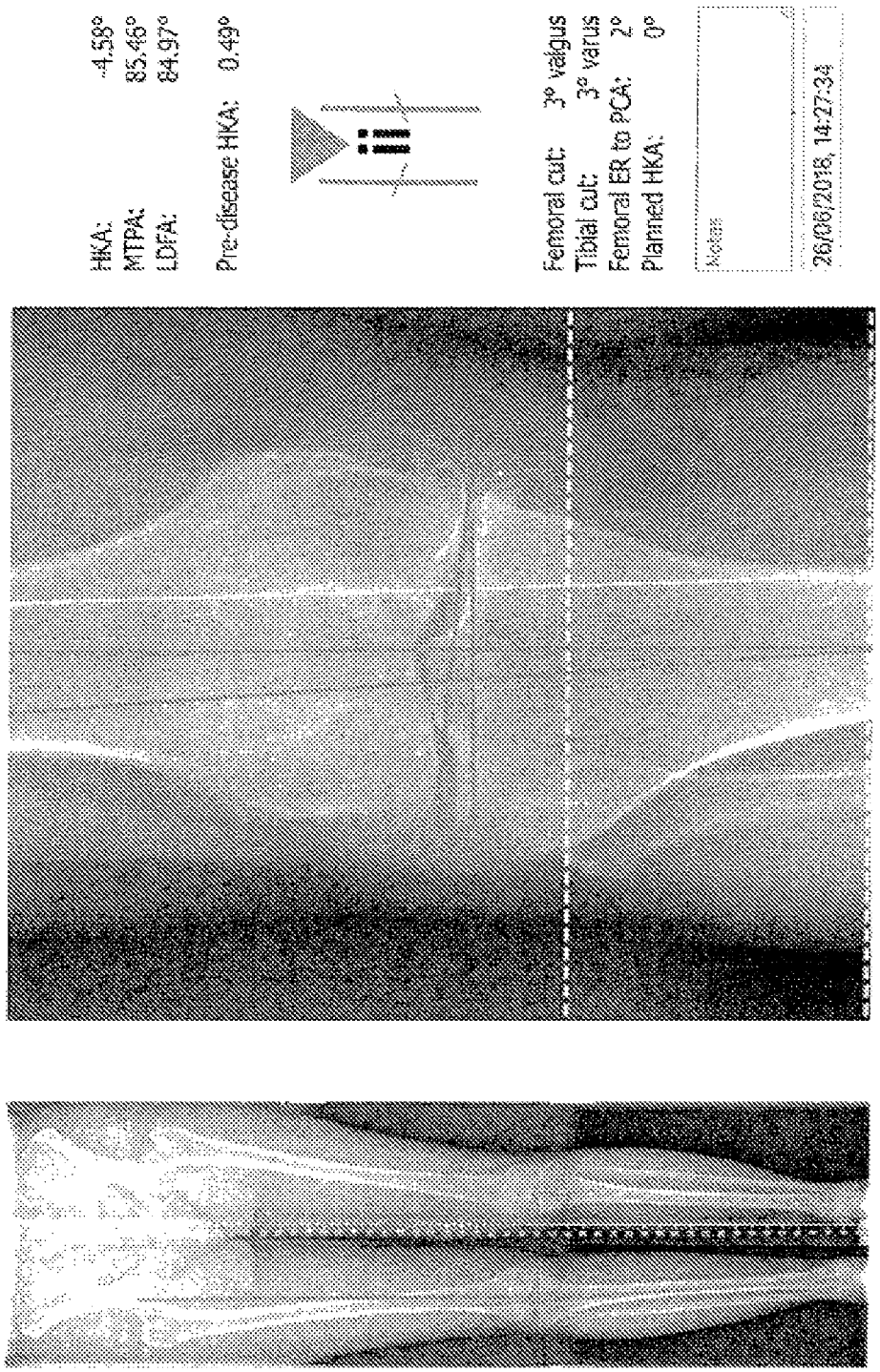
FIG. 16: Example of CPAK Plan Created by CPAK on-line calculator.

The CPAK web-based calculator was designed to assist with these calculations to reduce any potential error (See FIG. 16). Most surgical instrumentation, including the navigation system used for this study, measure distal femoral and proximal cuts as either 'varus' or 'valgus'. For the LDFA, 90 degrees is neutral, 86 degrees is 4 degrees of valgus and 93 degrees represents 3 degrees of varus. To avoid errors at the time of surgery, it the varus/valgus figures that correspond to the surgical navigation data that are produced and recorded in the surgical plan. The final surgical plan was recorded prior to randomisation.

Surgical Technique

Following randomisation, the patients were allocated to either the intervention group or the control group. All procedures were performed using optical navigation (OrthoMap Precision Navigation, Stryker, Kalamazoo, MI, USA). The distal femoral and proximal tibial resection were made as per the allocated group. Femoral component rotation was set in the KA group parallel to the native posterior condylar axis and in the MA group parallel to the surgical transepicondylar axis. In the KA group, if the planned tibial cut angle has been reduced in order to fall within the safe zone, then the femoral component was externally rotated by the same amount that the tibial cut was reduced in order to rebalance the flexion gap. A secondary check of flexion gap symmetry will also be undertaken using a gap tensiometer.

Trial components were inserted prior to any soft tissue release (other than those required by a standard approach). During trialling, the surgeon determined the most suitable size of tibial insert, and this will be replaced by a VERASENSE™ insert of the same size. The extensor mechanism will be approximated using a towel clip, and the knee cycled through a full range of movement. Occasionally it was necessary to change the thickness of the VERASENSE™ insert in response to the pressures being either too high or too low. In this case, the data recordings were repeated, and the new values will replace those recorded initially. Assessment of knee extension with the computer navigation system was performed concurrently to ensure that an extension loss of no more than 5 degrees is apparent.

Following this, the surgeon supported the posterior thigh with one hand and rest the heel in the other to reduce the amount of varus and valgus stress placed on the knee. The knee will then be flexed to 90 degrees (using the optical navigation to quantify the flexion) and the pressure values captured in this position. This was repeated at 45 degrees and 10 degrees. The readings will be recorded on the study data collection form by a non-operative member of the surgical team. These steps were repeated by the surgical assistant, and the data recorded for a second time.

Primary Outcome Measure

The primary outcome measure of this study was the initial difference in pressure between the medial and lateral compartments at 10 degrees of flexion (10-degree pressure delta). Because the compartment pressures was assessed by both the operating surgeon and an assistant, the absolute difference of the two readings will constitute the primary outcome measure. Hence a difference of 30 psi or less was considered in the balanced range when comparing intercompartmental pressure difference.

Intra-Operative Outcome Measures

Tibiofemoral Compartmental Pressure Loads—Initial medial and lateral compartmental pressure and final medial and lateral pressure loads will be compared in both groups at 10 degrees, 45 degrees and 90 degrees of knee flexion. Optimal knee balance will be defined as a pressure difference of less than 15 psi between compartments at 10 degrees, 45 degrees and 90 degrees of knee flexion, with no pressure exceeding 40 psi.

Requirements for Balancing—Additional balancing procedures were also recorded for each case including bone resections, ligament releases and change in polyethylene thickness.

Sample Size and Data Analysis

The senior authors have previously recorded the initial and final intra-compartment pressures of 280 consecutive TKAs using the VERASENSE™ device. The mean initial 10-degree pressure difference was 30 psi (SD 30 psi). The manufacturers recommend a pressure difference between lateral and medial compartments of <15 psi in order for the knee to be balanced. Using a 5% significance, a standard deviation of 30 and an 80% power to detect a difference of 15 psi, a sample size of 125 will be required. As the primary outcome measure is an intraoperative measurement, loss to follow-up will not be significant.

Normality of data distribution will be assessed and the Student's t-test will be used to compare differences in means with continuous variables. The Chi-squared test and Fishers exact test will be used for categorical data analysis as appropriate. Intention-to-treat analysis will be performed in the primary analysis. In addition, a per-protocol analysis including participants according to treatment received will also be added as a secondary analysis.

Results

A total of 132 patients were screened for suitability for this trial. Two patients refused to participate, and one patient did not meet the inclusion criteria. A further four patients were allocated to treatment groups but were not included in the final analysis due to technology failures during the surgery resulting in data not being able to be collected. This left a final cohort for analysis of 125 patients with 138 knees undergoing analysis. A total of 13 patients underwent bilateral knee surgeries. 70 knees were assigned to KA and 68 knees to MA.

The mean age of the cohort was 68.3 years (range 36-89 years, SD 9.3). There were 60 left knees and 78 right knees. There was 73 women and 52 men in the cohort. Mean pre=operative HKA was −3.3 degrees (range −17.7 to 19.9 degrees).

Primary Outcome Measure—Intercompartmental Pressure Difference

Figure 17:
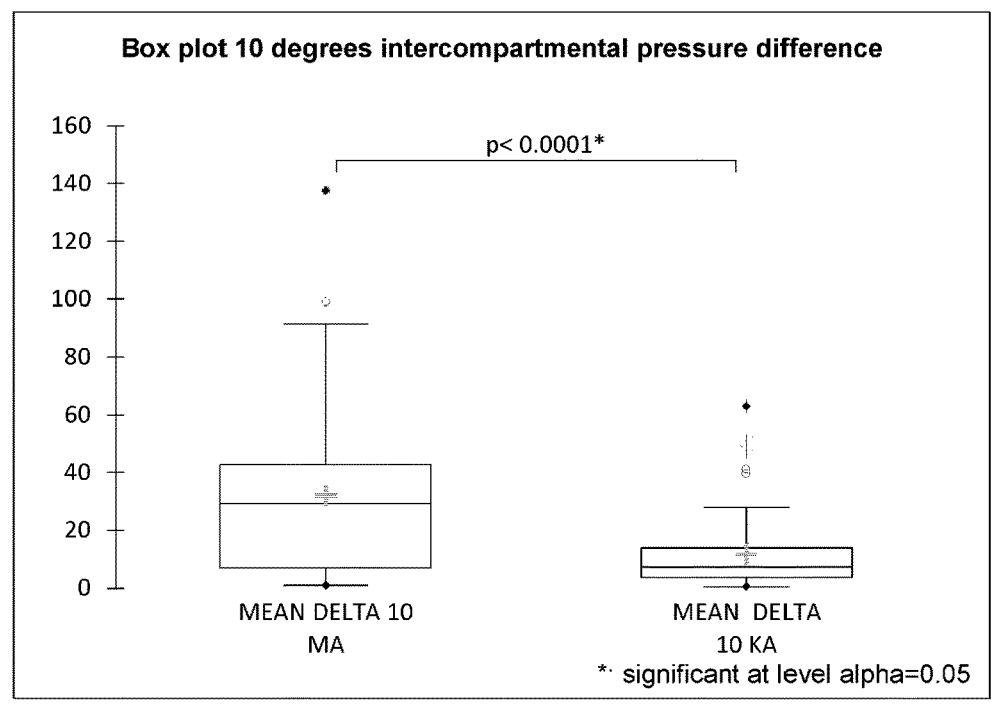
FIG. 17: Intercompartmental Pressure Difference at 10 degrees. In this box plot, normal range of psi of 15 or less as the intercompartmental pressure difference is the mean of the 2 observers.

The mean intercompartmental pressure difference at 10 degrees for all groups was 64.6 PSI in the MA group and 24 PSI in the KA group (normal range 0-30 PSI, p<0.0001). See FIG. 17.

Figure 18:
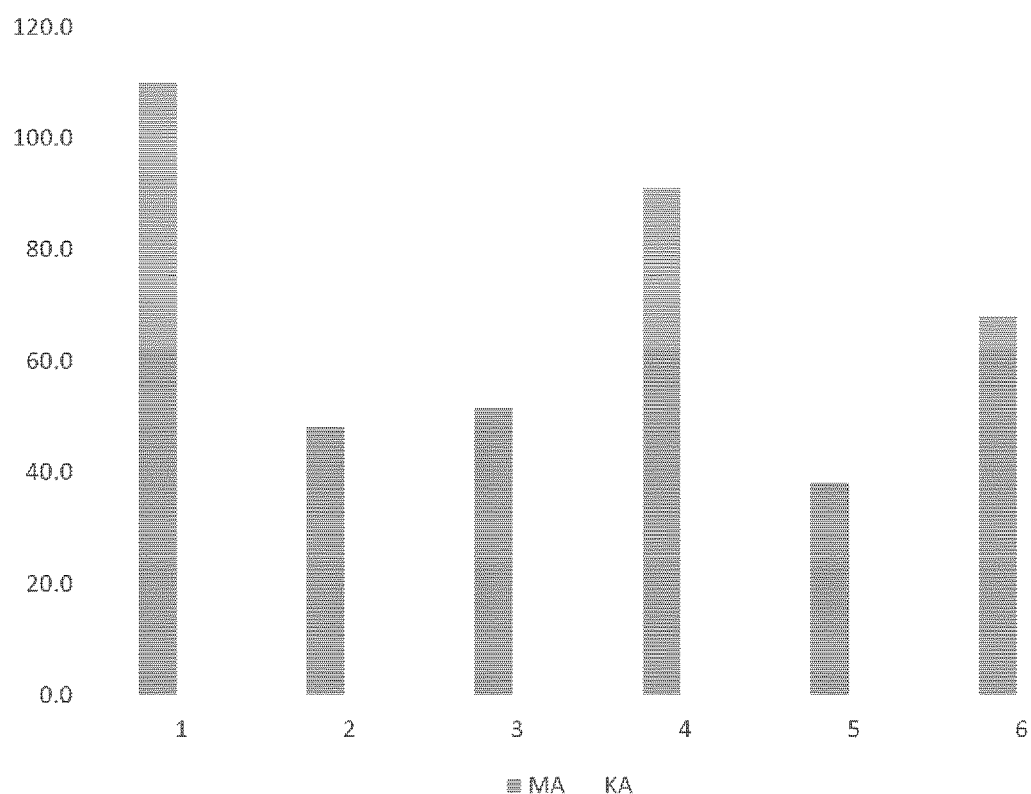
FIG. 18: Intercompartmental Pressure Difference per CPAK Type at 10 degrees. Note that a balanced knee state was considered a delta of 30 PSI or less as it was the sum of 2 observers.

Table 14 and FIG. 18 show mean in mean intercompartmental pressure difference at 10 degrees per CPAK group. CPAK types 1 and 4 shows greatest mean difference between groups.

TABLE 14

Mean Intercompartmental Difference Between Groups Per CPAK Type.

| CPAK type | Number | MA MEAN DELTA | KA MEAN DELTA | Diff |
|---|---|---|---|---|
| 1 | 23 | 110.2 | 13.0 | 97.2 |
| 2 | 53 | 48.0 | 25.1 | 22.9 |
| 3 | 28 | 51.5 | 32.6 | 18.9 |
| 4 | 15 | 91.2 | 23.2 | 67.9 |
| 5 | 12 | 38.0 | 13.7 | 24.3 |
| 6 | 7 | 68.0 | 36.5 | 31.5 |

Note that a balanced knee state was considered a delta of 30 PSI or less as it was the sum of 2 observers.

Balanced Knee State

Figure 19:
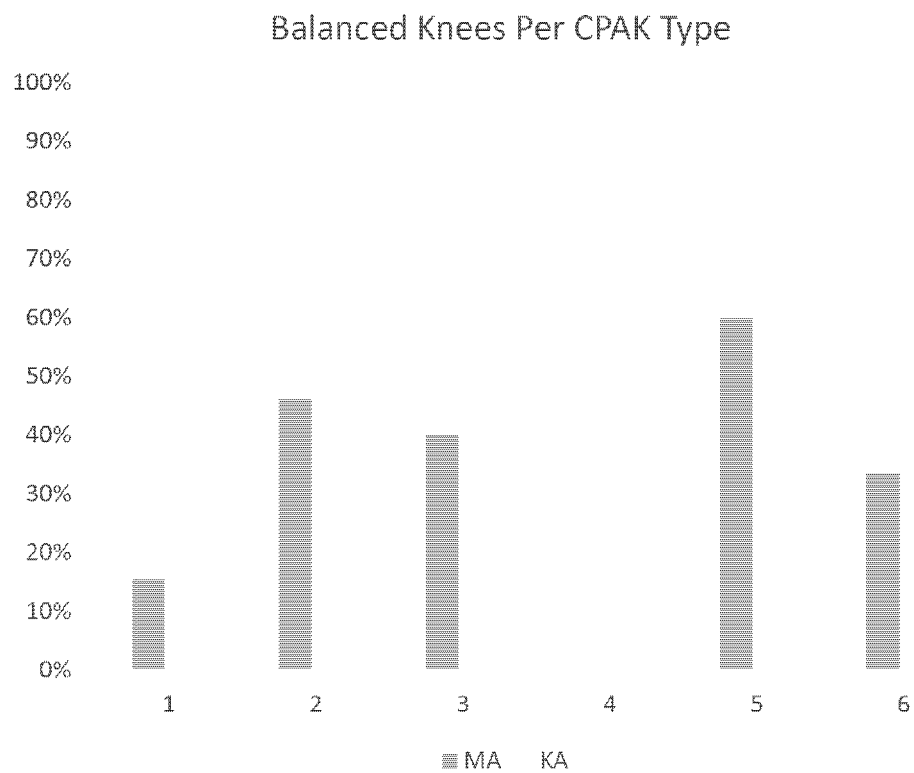
FIG. 19: Balanced Knees per CPAK Type.

When comparing the proportion of balanced knees in each group, 80% were balanced in the KA group and 35% in the MA group. Table 15 and FIG. 19 shows proportion and percentage of cases balanced per CPAK group.

TABLE 15

CPAK Type and Balance

| CPAK | n per CPAK | MA (n) | KA (n) | MA Balanced (n) | % MA Balanced | KA Balanced (n) | % KA Balanced |
|---|---|---|---|---|---|---|---|
| 1 | 23 | 13 | 10 | 2 | 15% | 10 | 100% |
| 2 | 53 | 26 | 27 | 12 | 46% | 21 | 78% |
| 3 | 28 | 15 | 13 | 6 | 40% | 8 | 62% |
| 4 | 15 | 6 | 9 | 0 | 0% | 8 | 89% |

TABLE 15-continued

CPAK Type and Balance

| CPAK | n per CPAK | MA (n) | KA (n) | MA Balanced (n) | % MA Balanced | KA Balanced (n) | % KA Balanced |
|---|---|---|---|---|---|---|---|
| 5 | 12 | 5 | 7 | 3 | 60% | 7 | 100% |
| 6 | 7 | 3 | 4 | 1 | 33% | 2 | 50% |

Requirements for Knee Balancing

Figure 20:
FIG. 20: Histogram of Recuts Per CPAK type.
Figure 21:
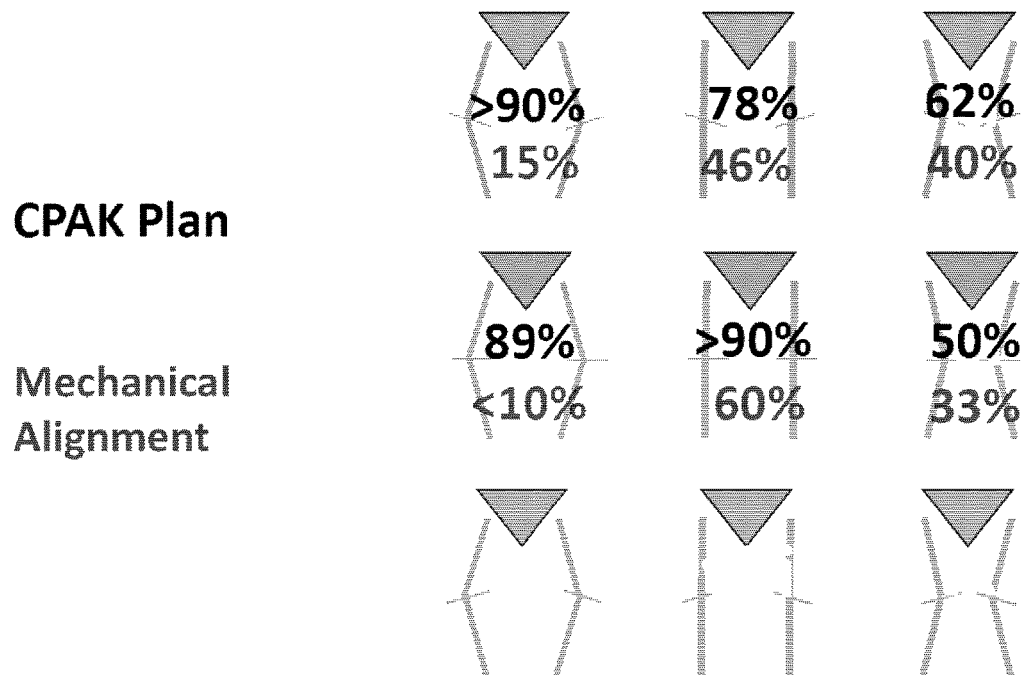
FIG. 21: Likelihood Ratios of Achieving Knee Balance Based on CPAK Type. (note for values greater than 90% or less than 10%, a cut off value of >90% or <10% respectively is used).

There was a higher proportion of cases requiring bone recuts to achieve knee balance in the MA versus than KA group (49% versus 9% respectively). This finding was also consistent when analysed per CPAK group. See table 16 and FIG. 20.

TABLE 16

Requirements for Recuts Per CPAK Group

| CPAK | MA (n) | MA | KA (n) | KA |
|---|---|---|---|---|
| 1 | 9 | 69% | 0 | 0% |
| 2 | 11 | 42% | 4 | 15% |
| 3 | 7 | 47% | 0 | 0% |
| 4 | 3 | 50% | 1 | 11% |
| 5 | 2 | 40% | 0 | 0% |
| 6 | 1 | 33% | 1 | 25% |

Conclusions

In this study, we were able to demonstrate that reproducing the constitutional alignment of the lower limb using the CPAK Classification resulted in a significantly greater probability that knee balance would be achieved. In addition, the rate of knee balancing was significantly less in those patients treated with KA surgery with the CPAK Plan which may reduce the risk of post-operative knee pain, ligament trauma and secondary effects related to such interventions.

The CPAK classification offers a pragmatic approach to defining the normal and arthritic knee alignment. It considers both HKA and JLA in its definition and allows boundaries to be set when undertaking KA TKA based on surgeon preference, prior published literature and patient factors. We also believe this classification can offer consistency in reporting amongst future studies.

This is the first classification system for knee alignment that is capable of predicting the likelihood of achieving knee balance. It compares the CPAK plan to the current gold standard of alignment in knee arthroplasty which is mechanical knee alignment. In doing so, it offers clinicians valuable information prior to commencement of the operation on what the probability of balance will be based on the technique used.

Certain CPAK types have a higher likelihood of achieving a balanced knee state with CPAK surgery compared to mechanical alignment and may guide surgeon decision-making. In particular, types 1 and 4 knees behave very differently with nearly 905 or more knees being balanced in the CPAK group and 15% or less when mechanical alignment was used. Across all groups, the knee arthroplasties implanted using CPAK plan had better balance than those knees implanted in mechanical alignment.

REFERENCES

1. Paley, D., *Principles of Deformity Correction.* 2003, Heidelberg, Germany: Springer-Verlag.
2. Bellemans, J., et al., *The Chitranjan Ranawat award: is neutral mechanical alignment normal for all patients? The concept of constitutional varus.* Clin Orthop Relat Res, 2012. 470(1): p. 45-53.
3. Parratte, S., et al., *Effect of postoperative mechanical axis alignment on the fifteen-year survival of modern, cemented total knee replacements.* J Bone Joint Surg Am, 2010. 92(12): p. 2143-9.
4. Ritter, M. A., et al., *Postoperative alignment of total knee replacement. Its effect on survival.* Clin Orthop Relat Res, 1994(299): p. 153-6.

Example 6

A Validation Study of the Coronal Plane Alignment of the Knee (CPAK) Calculator

Introduction

With the evolution of new strategies in knee alignment, pre-operative radiographic templating is a vital part of planning in total knee arthroplasty (TKA). Multiple methods have been used, including short- and long-leg radiographs, CT scout films, and 3-dimensional computed models (1-3). Long-leg radiographs (LLR) are a common and reliable technique to measure the mechanical axis of the hip-knee-ankle (HKA) angle before and after the procedure (4, 5). The utility of LLRs also assists the surgeon to establish the relation between the mechanical axis and the joint line. Current categorisation of the joint line has been neutral, varus, or valgus with respect to the mechanical axis, and restoration of the joint line perpendicular to this axis has been a standard assumption in knee arthroplasty (6).

In the prior Examples, we described the Coronal Plane Alignment of the Knee (CPAK) classification that distinguishes between lower limb alignment and joint line as two independent variables, and elaborates on the concept that not all native knees have a joint line parallel to the horizontal. Depending on the degree of the bone loss amongst other factors, the joint line may also form acute or obtuse angles to the horizontal. In the CPAK description, a neutral, varus, or valgus knee may have a joint line that is neutral, acute angulated (apex proximal), or obtuse angulated (apex distal). The classification therefore describes nine categories of coronal knee alignment (Types i-ix). Calculation of the joint line angles requires measurement of two smaller component angles: the Lateral Distal Femoral Angle (LDFA) and the Medial Proximal Tibial Angle (MPTA). The LDFA is the angle formed by the mechanical axis of the femur and the femoral joint line. The MPTA is the angle formed by the mechanical axis of the tibia and the tibial joint line. The concept of these angles is not new, as it has previously been described by Park et al. (7).

We are not aware of any web-based calculators that permit knee arthroplasty surgeons to calculate these parameters, using recognized variables with clinical applicability to execution of a surgical plan within pre-determined boundaries. Hence, we have developed an online calculator that is capable of determining multiple surgical parameters required in TKA surgery, particularly if restoration of the constitutional alignment of the lower limb alignment is the aim. These measurements include the arthritic HKA, the pre-arthritic HKA, the distal femoral and proximal tibial joint line resection angles and classification via the CPAK model.

With little known about the accuracy of such a planning tool, the aim of this study is to assess the inter- and intra-observer reliability of the online calculator for pre-operative planning in TKA. Our hypothesis is that the measuring tool has high inter-observer concordance and is a reliable planning tool for coronal knee alignment angles in TKA.

Methods

Twenty-five pre-operative, de-identified LLRs for patients undergoing TKA were accessed from a private practice research database. Four observers were included: three consultant orthopaedic surgeons and an orthopaedic registrar: WGJ, NF, DC, and SM. Study approval was obtained by our institutional review board.

Weight-bearing LLRs included landmarks from the anterior superior iliac crest to the tibio-talar joint. The X-ray beam was set at 0 degrees, centred between the inferior pole of the patella and the tibial tubercle. Medial malleoli were spaced 15 cm apart, with weight distributed equally between the lower limbs. Film-to-focus distance was 183 cm. Radiologic dose equated to 4.5 mSv.

The CPAK calculator in an on-line, password-protected website. Long-leg radiographs are temporarily uploaded onto the site for the purpose of the calculations only; none of the radiographs or the data generated is stored locally or remotely, and are deleted when the calculations are complete. The website takes the user step-by-step through the points on the radiograph required to generate the data: centre of the femoral head, centre of the ankle, centre of the distal femur, centre of the tibial plateau, distal point of the medial and lateral femoral condyles, and distal point of the medial and lateral tibial plateaus. The planning mode allows the surgeon to select resection boundaries for the HKA, LDFA and MPTA. The calculator then displays the alignment classification—Types i to ix (see FIG. 16); HKA; LDFA; MPTA; pre-disease HKA; femoral and tibial cut suggestions, and femoral external rotation to posterior condylar angle.

Each observer was asked to undertake radiographic planning on each of the 25 LLRs using the CPAK measurement tool. One week later, each observer repeated the calculations on the same radiographs, which were presented in a different order. All the data points were collected for each radiograph. There were no missing values.

The primary outcome of this study was agreement between observers as well as intra-observer agreement.

Statistical Analysis

Data was collected in Microsoft® Excel for Mac, version 15.31, and data were analysed using Graphpad Prism Mac 7.0. Pearson correlation coefficients, r, were calculated between scores, using 95% confidence intervals and two-tailed p-values, with p<0.05 considered significant. Bland-Altman analysis was used to quantify agreement between continuous data, using mean differences and limits of agreement.

Results

HKA Calculation Results

|  | First round of calculations | | | Second round of calculations | | |
| --- | --- | --- | --- | --- | --- | --- |
|  | Pearson Coefficient | r-Squared | p-value | Pearson Coefficient | r-Squared | p-value |
| WGJ | 0.999 | 0.998 | <0.0001 | 0.999 | 0.998 | <0.0001 |
| NF | 0.998 | 0.996 | <0.0001 | 0.999 | 0.998 | <0.0001 |
| DC | 0.999 | 0.999 | <0.0001 | 0.999 | 0.998 | <0.0001 |
| SM | 0.998 | 0.996 | <0.0001 | 0.999 | 0.998 | <0.0001 |

Bias, or Average Difference in the HKA Calculations (Using Bland-Altman Analysis)

|  | First round of calculations | | | Second round of calculations | | |
| --- | --- | --- | --- | --- | --- | --- |
|  | Bias | Standard Deviation | 95% CI of Limits of Agreement | Bias | Standard Deviation | 95% CI of Limits of Agreement |
| WGJ | −0.085 deg | 0.270 | −0.614-0.444- | −0.037 | 0.273 | −0.572-0.498- |
| NF | 0.281 deg | 0.350 | −0.475-0.911 | 0.146 | 0.245 | −0.333-0.625- |
| DC | −0.065 deg | 0.198 | −0.453-0.323 | −0.142 | 0.241 | −0.614-0.330- |
| SM | −0.068 deg | 0.358 | −0.769-0.633 | 0.034 | 0.315 | −0.584-0.652- |

There was near perfect positive correlation assessing inter-observer reliability for both first and second measures of the HKA (Table 1; Pearson's coefficients and R-squared 0.99 for all observers; p<0.0001). Mean difference in HKA measures using Bland-Altman plots was low for all observers on first and second round calculations. Observer mean differences were all below 0.3 degrees with 95% confidence interval limits of agreement all under 1 degree.

Inter-observer Pearson's coefficient for the $1^{st}$ HKA calculation were 0.999, 0.998, 0.999, and 0.998 for WGJ, NF, DC, and SM respectively compared to the mean. R squared values were 0.998, 0.996, 0.999, and 0.996 respectively. P values were <0.0001 across all observers. For the $2^{nd}$ HKA calculation, Pearson's coefficient 0.999, 0.999, 0.999, and 0.999 for WGJ, NF, DC, and SM respectively compared to the mean observation. R squared values were 0.998, 0.998, 0.998, and 0.998 respectively. P values were <0.0001 across all observers.

Figure 23:
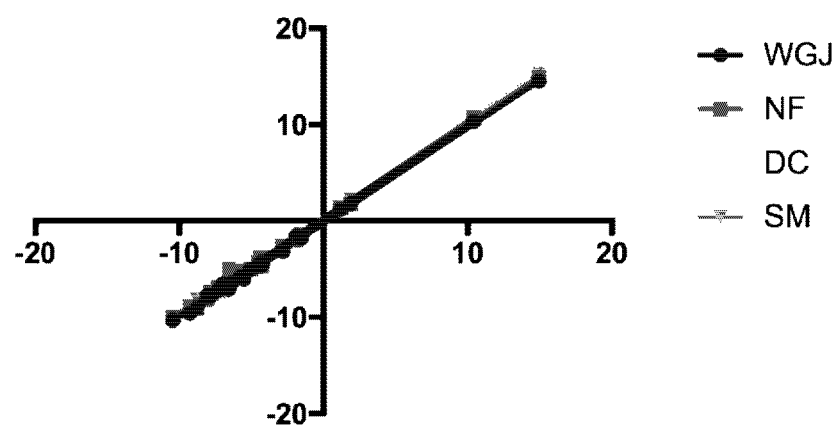
FIG. 23: Correlation of HKA—$1^{st}$ Measurement
Figure 24:
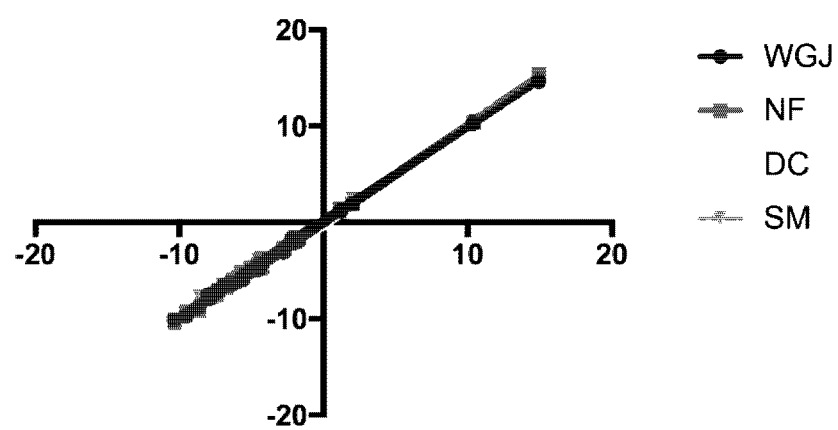
FIG. 24: Correlation of HKA—$2^{nd}$ Measurement
Figure 25:
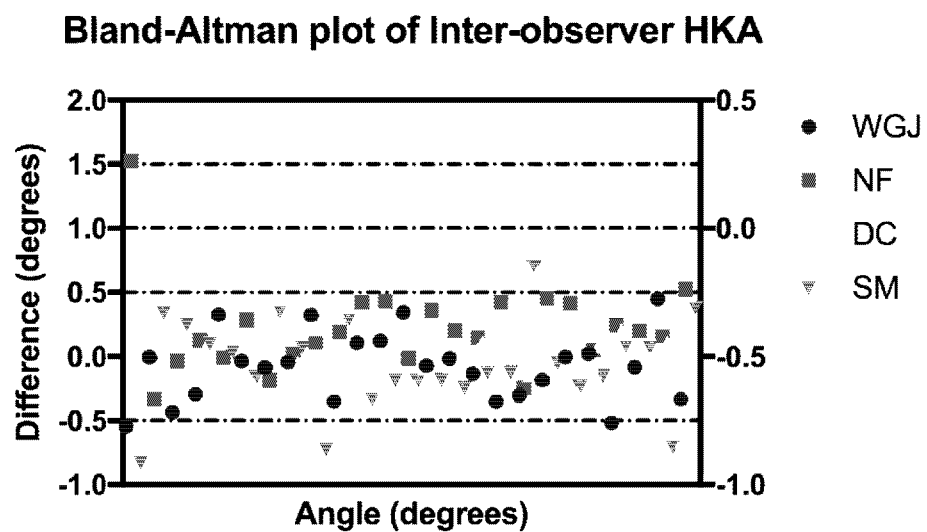
FIG. 25: Bland-Altman Plot of Inter-observer HKA

Bias, or average difference in the $1^{st}$ HKA calculation for WGJ compared to the mean, using Bland-Altman analysis was −0.0848 degrees, std dev 0.27, 95% limits of agreement: −0.614, 0.444. For NF, bias of 0.281 degrees, std dev 0.35, 95% limits of agreement: −0.475, 0.911. For DC, bias of −0.0652 degrees, std dev 0.198, 95% limits of agreement: −0.453, 0.323. For SM, bias of −0.068 degrees, std dev 0.358, 95% limits of agreement: −0.769, 0.633. For the $2^{nd}$ HKA calculation, the WGJ bias was −0.037 degrees, std dev 0.273, 95% limits of agreement −0.572, 0.498. For NF, bias of 0.146 degrees, std dev 0.245, 95% limits of agreement −0.333, 0.625. For DC, bias of −0.142 degrees, std dev 0.241, 95% limits of agreement −0.614, 0.33. For SM, bias of 0.034 degrees, std dev 0.315, 95% limits of agreement −0.584, 0.652. See FIGS. 23 to 25.

MPTA Calculation Results

Inter-observer Pearson's coefficient for the $1^{st}$ MTPA calculation were 0.979, 0.959, 0.966, and 0.955 for WGJ, NF, DC, and SM respectively compared to the mean. R squared values were 0.958, 0.919, 0.934, and 0.912 respectively. P values were <0.0001 across all observers. For the $2^{nd}$ MTPA calculation, Pearson's coefficient 0.975, 0.934, 0.952, and 0.956 for WGJ, NF, DC, and SM respectively compared to the mean. R squared values were 0.950, 0.873, 0.907, and 0.914 respectively. P values were <0.0001 across all observers.

Figure 26:
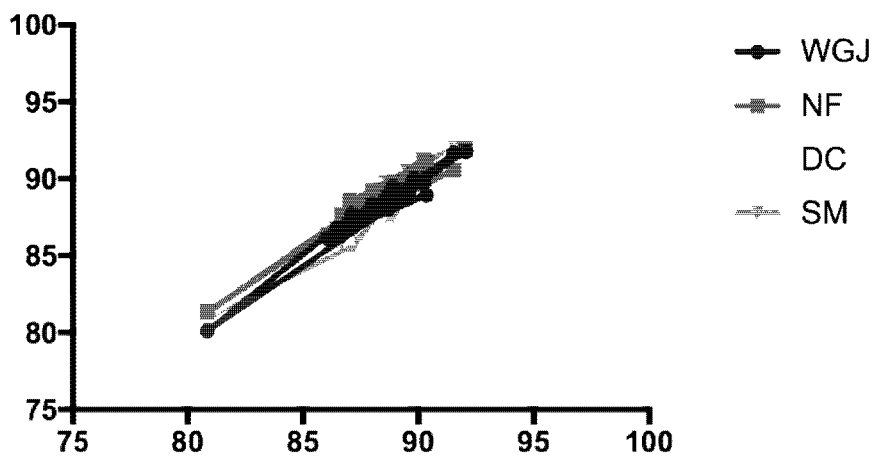
FIG. 26: Correlation of MTPA—$1^{st}$ Measurement
Figure 27:
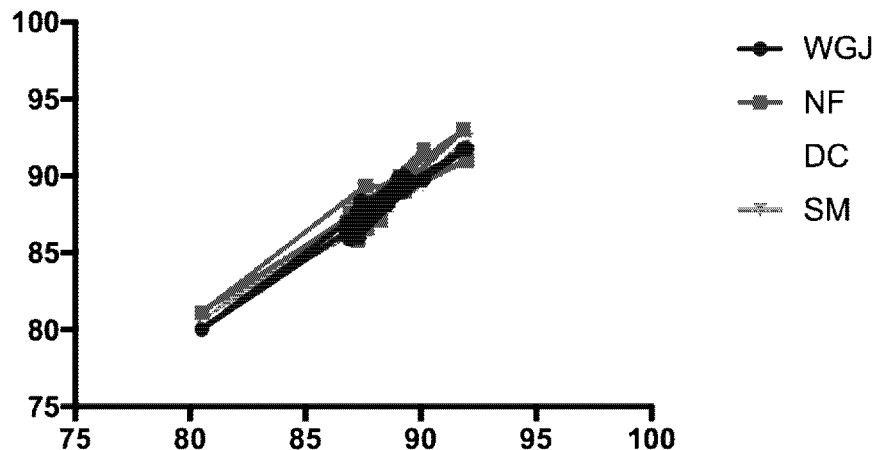
FIG. 27: Correlation of MTPA—$2^{nd}$ Measurement
Figure 28:
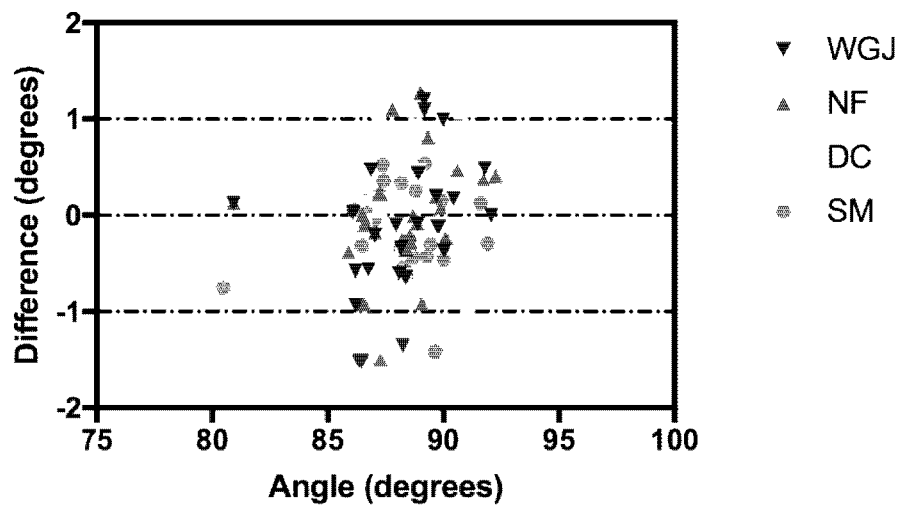
FIG. 28: Bland-Altman Plot of Inter-observer MTPA

Bias, or average difference in the $1^{st}$ MTPA calculation for WGJ compared to the mean, using Bland-Altman analysis was −0.149 degrees, std dev 0.452, 95% limits of agreement: −1.035, 0.738. For NF, bias of 0.314 degrees, std dev 0.0.620, 95% limits of agreement: −0.9, 1.529. For DC, bias of −0.015 degrees, std dev 0.599, 95% limits of agreement: −1.19, 1.16. For SM, bias of −0.151 degrees, std dev 0.732, 95% limits of agreement: −1.585, 1.283. For the $2^{nd}$ MTPA calculation, the WGJ bias was −0.126 degrees, std dev 0.517, 95% limits of agreement −1.14, 0.887. For NF, bias of 0.092 degrees, std dev 0.814, 95% limits of agreement −1.504 degrees, 1.688. For DC, bias of 0.084 degrees, std dev 0.675, 95% limits of agreement −1.24, 1.408. For SM, bias of −0.050 degrees, std dev 0.628, 95% limits of agreement −1.281, 1.182. See FIGS. 26 to 28.

LDFA Calculation Results

Inter-observer Pearson's coefficient for the $1^{st}$ LDFA calculation were 0.977, 0.940, 0.971, and 0.977 for WGJ, NF, DC, and SM respectively compared to the mean observation. R squared values were 0.955, 0.883, 0.943, and 0.954 respectively. P values were <0.0001 across all observers. For the $2^{nd}$ LDFA calculation, Pearson's coefficient 0.979, 0.982, 0.988, and 0.985 for WGJ, NF, DC, and SM respectively compared to the mean observation. R squared values were 0.959, 0.964, 0.976, and 0.969 respectively. P values were <0.0001 across all observers.

Figure 29:
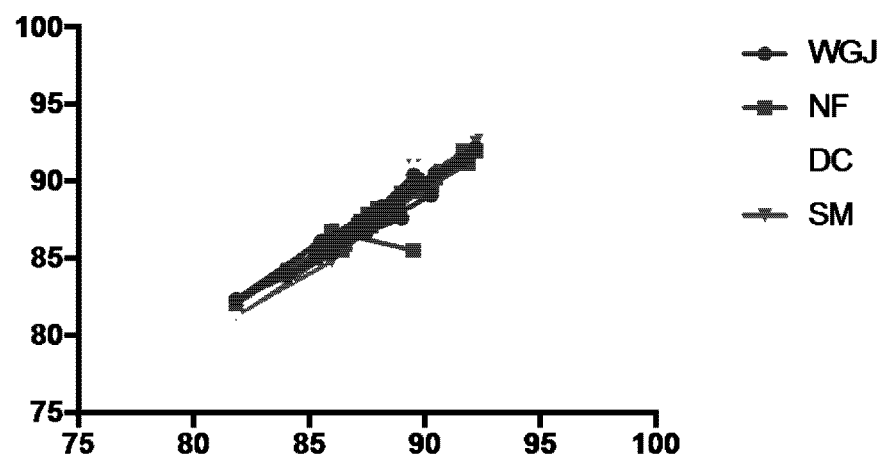
FIG. 29: Correlation of LDFA—$1^{st}$ Measurement
Figure 30:
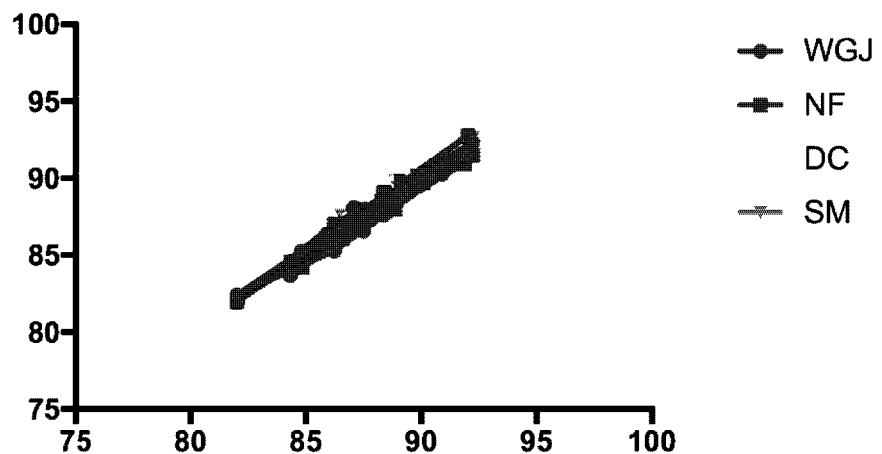
FIG. 30: Correlation of LDFA—$2^{nd}$ Measurement
Figure 31:
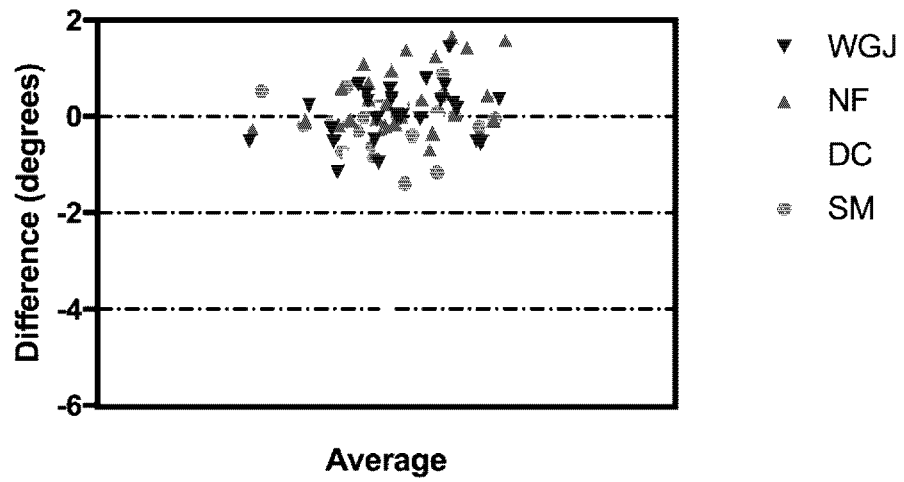
FIG. 31: Bland-Altman Plot of Inter-observer LDFA

Bias, or average difference in the $1^{st}$ LDFA calculation for WGJ compared to the mean, using Bland-Altman analysis was −0.159, std dev 0.531, 95% limits of agreement: −1.2, 0.881. For NF, bias of −0.308, std dev 0.858, 95% limits of agreement: −1.991, 1.374. For DC, bias of −0.403, std dev 0.679, 95% limits of agreement: −0.921, 1.728. For SM, bias of −0.064, std dev 0.586, 95% limits of agreement: −1.085, 1.213. For the $2^{nd}$ MTPA calculation, the WGJ bias was −0.198, std dev 0.517, 95% limits of agreement −1.21, 0.815. For NF, bias of −0.026, std dev 0.485, 95% limits of agreement −0.976, 0.925. For DC, bias of 0.204, std dev 0.459, 95% limits of agreement −0.696, 1.104. For SM, bias of 0.019, std dev 0.457, 95% limits of agreement −0.877, 0.916. See FIGS. 29 to 31.

Intra-Observer Analysis

Comparison of measurements of the HKA, for WGJ, from the $1^{st}$ to $2^{nd}$ measurement had an Intra-observer Pearson's of 0.999, 95% CI of 0.999 to 0.999, R squared 0.999, and P<0.0001. For MTPA, Pearson's value was 0.997, 95% CI of 0.992 to 0.999, R squared 0.993, and P<0.0001. For LDFA, Pearson's value was 0.997, 95% CI of 0.993 to 0.999, R squared 0.994, P<0.0001.

Figure 32:
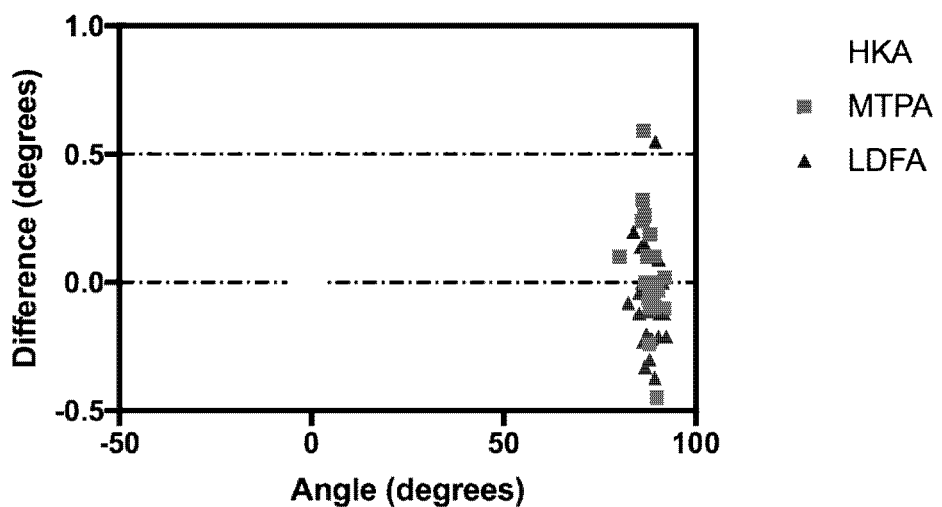
FIG. 32: Bland-Altman plot of Intra-observer WGJ

The intra-observer bias, or mean average difference, for WGJ using Bland-Altman analysis for HKA was 0.007, with a std dev of 0.141, and 95% limits of agreement −0.269 to 0.283. For MTPA, the bias was 0.024, std dev 0.199, 95% limits of agreement −0.367 to 0.415. For LDFA, the bias was −0.057, std dev 0.199, 95% limits of agreement −0.447 to 0.333. See FIG. 32.

For NF, comparison of measurements of the HKA from the $1^{st}$ to $2^{nd}$ measurement had an Intra-observer Pearson's of 0.997, 95% CI of 0.992 to 0.999, R squared 0.993, and P<0.0001. For MTPA, Pearson's value was 0.921, 95% CI of 0.826 to 0.965, R squared 0.848, and P<0.0001. For LDFA, Pearson's value was 0.897, 95% CI of 0.778 to 0.954, R squared 0.805, P<0.0001.

Figure 33:
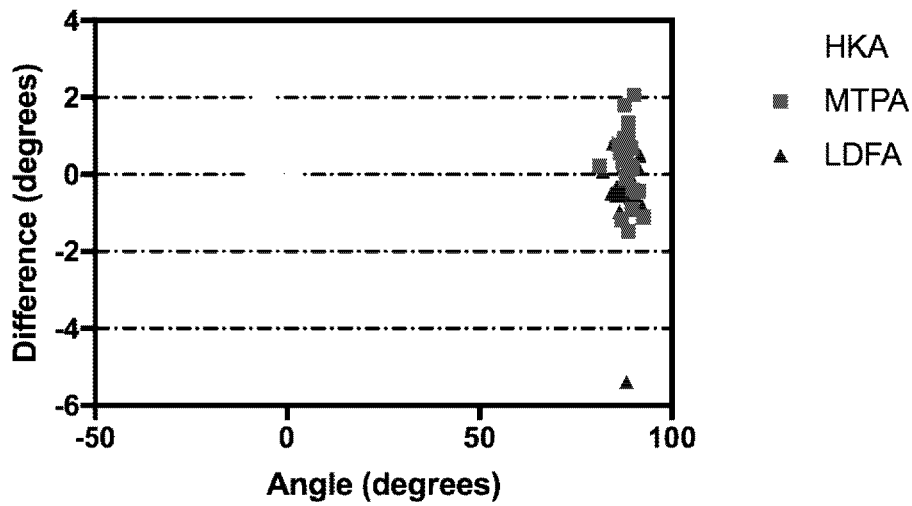
FIG. 33: Bland-Altman plot of NF Intra-observer

The intra-observer bias, or mean average difference, for NF using Bland-Altman analysis for HKA was 0.126, with a std dev of 0.490, and 95% limits of agreement −0.834 to 1.087. For MTPA, the bias was 0.268, std dev 0.897, 95% limits of agreement −1.477 to 2.014. For LDFA, the bias was −0.378, std dev 1.123, 95% limits of agreement −2.579 to 1.823. See FIG. 33.

For DC, comparison of measurements of the HKA from the 1st to 2nd measurement had an Intra-observer Pearson's of 0.999, 95% CI of 0.997 to 0.999, R squared 0.997, and P<0.0001. For MTPA, Pearson's value was 0.913, 95% CI of 0.81 to 0.961, R squared 0.833, and P<0.0001. For LDFA, Pearson's value was 0.922, 95% CI of 0.829 to 0.966, R squared 0.851, P<0.0001.

Figure 34:
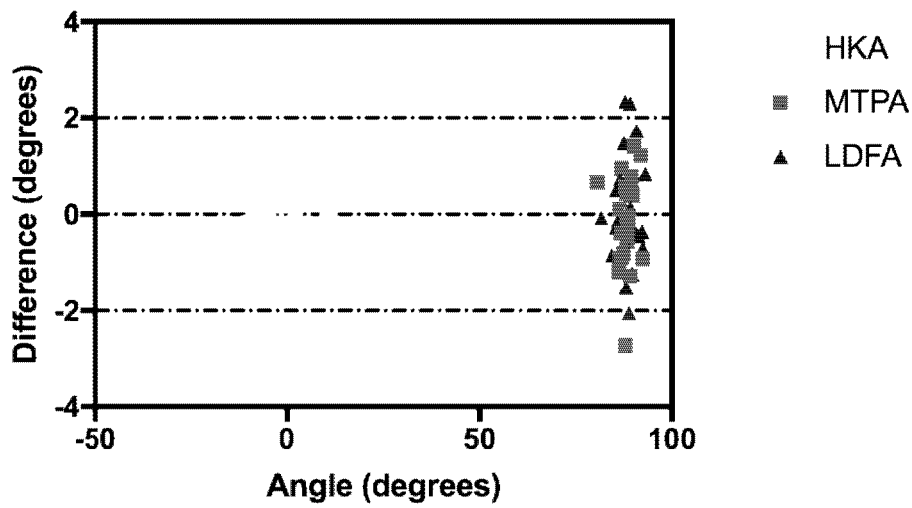
FIG. 34: Bland-Altman plot of DC Intra-observer WGJ

The intra-observer bias, or mean average difference, for DC using Bland-Altman analysis for HKA was 0.131, with a std dev of 0.323, and 95% limits of agreement −0.501 to 0.764. For MTPA, the bias was −0.053, std dev 0.950, 95% limits of agreement −1.915 to 1.81. For LDFA, the bias was 0.104, std dev 1.08, 95% limits of agreement −2.013 to 2.222. See FIG. 34.

For SM, comparison of measurements of the HKA from the 1st to 2nd measurement had an Intra-observer Pearson's of 0.999, 95% CI of 0.997 to 0.999, R squared 0.997, and P<0.0001. For MTPA, Pearson's value was 0.883, 95% CI of 0.749 to 0.947, R squared 0.779, and P<0.0001. For LDFA, Pearson's value was 0.972, 95% CI of 0.935 to 0.988, R squared 0.944, P<0.0001.

Figure 35:
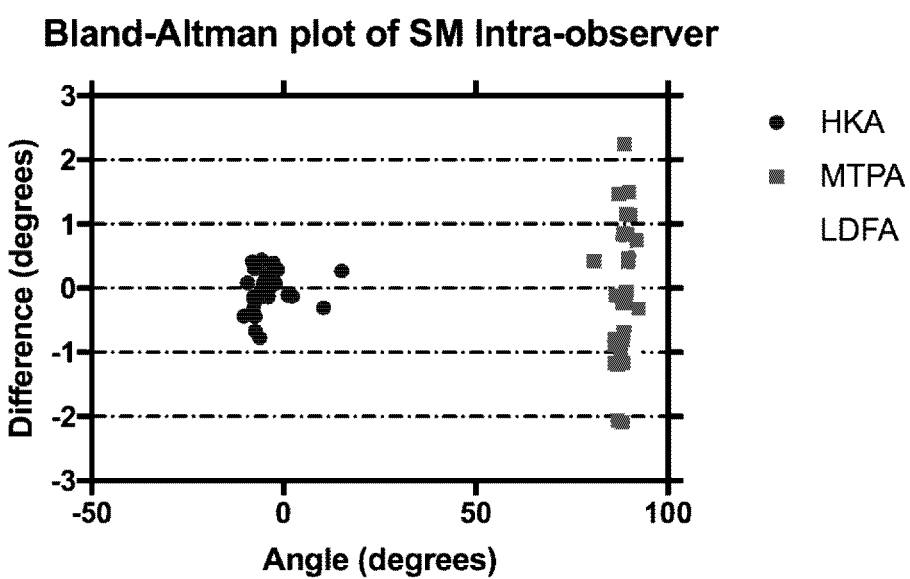
FIG. 35: Bland-Altman plot of SM Intra-observer WGJ

The intra-observer bias, or mean average difference, for SM using Bland-Altman analysis for HKA was −0.047, with a std dev of 0.328, and 95% limits of agreement −0.691 to 0.596. For MTPA, the bias was −0.055, std dev 1.138, 95% limits of agreement −2.285 to 2.175. For LDFA, the bias was −0.050, std dev 0.636, 95% limits of agreement −1.296 to 1.195. See FIG. 35.

Discussion

This study found high inter-observer and intra-observer reliability between observers confirming the accuracy of the on-line calculator. Levels of agreement between observers and measures were high and independent of level of experience. Levels of agreement were also high for determining the HKA, MPTA and the LDFA. Hence we feel the results support the use of this calculator as an accurate tool to plan for TKA surgery.

The CPAK classification includes varus, neutral, and valgus classification of knee alignment, and adds three types of joint line anatomies. The apex distal alignment accounts for medial tibial deformity and bone loss in the varus and neutrally aligned arthritic knee (Types i and ii). Knees categorized as apex distal alignment in varus (Type i) are the ones described by Bellemans as "constitutional varus" (8). When the CPAK calculator was used to map the knees from the Bellemans' article, approximately 66% of arthritic knees fall into one of these two categories. Some degree of lateral femoral condyle bone loss may be present in apex distal deformity in neutral and valgus knees.

The apex proximal group represent rare categories in knee alignment. One main reason for this is that in varus and neutral knees in the apex proximal group, medial compartment bone loss is greater in the femur than in the tibia. Wear patterns involving the medial femoral condyle are rare in osteoarthritic knees (9). The lateral compartment of the tibia is worn in apex proximal alignment in neutral and valgus knees, which also represents an uncommon pattern (9).

The joint-line neutral group of varus, neutral, and valgus mechanically aligned knees represents the current dogma of mechanical alignment. Knees in these three groups have a tibiofemoral joint line that is parallel to the ground on weight bearing. Varying degrees of bone loss to the distal femur or proximal tibia may be present depending on the category. The surgeon's goal is to generate post-operative alignment of a neutral mechanical axis with a neutral joint line perpendicular to it, falling into the middle category of this group (Type v). An HKA within 3 degrees of neutral reduces the risk of implant failure in the medium to long term (10, 11).

In addition to categorizing knee types in a paradigm that accurately represents the true proportions of natural knee alignment, the CPAK classification aims to assist the orthopaedic surgeon templating bony cuts to the femur and tibia. This is done through the calculator as it suggests the varus/valgus angle of the femoral and tibial resection to achieve neutrality of the mechanical axis and the joint line. While intra-operative bony resection is also determined by sagittal and axial plane alignment, and ligaments and other soft tissues crossing the knee, CPAK endeavours to minimize errors in coronal plane resection.

For the present Example, the CPAK calculator generated data from long-leg radiographs exclusively. The long-leg films typically allow more accurate determination of the LDFA and MPTA angles through the mechanical axis that may be affected by extra-articular deformity in the shafts of the femur and tibia. Previous studies, including a study by Park et al., have determined that the short-leg radiograph may not accurately describe the mechanical axis of the limb (7). While many orthopaedic surgeons may not routinely request long-leg radiographs for their patients undergoing TKA, it is the gold standard for coronal alignment, and preferable for the use of the CPAK classification.

Accurate coronal knee alignment can enhance the longevity of total knee prostheses. The proposed mechanism is through physiologic load distributions through the polyethylene components (12-15). Disproportionate contact stresses within medial and lateral compartments may result in increased wear on the bearing surface. Intra-operative measurements of contact stresses within the compartments was described by Shelton et al. in knees with varying alignments, without significant stress differences (16). However, contact forces may be different upon weight bearing. More accurate measurements in the planning stages of knee arthroplasty could help reduce the residual deformity in the coronal plane post-operatively. This especially benefits patients with significant pre-operative deformity and bone loss.

Literature on the effects of coronal plane alignment on patellofemoral tracking is scarce. Coronal plane alignment may alter contact stresses between the patella and femur, according to Slevin et al. (17). Consequences of these contact stresses, including wear of native patella cartilage in the non-resurfaced knee or on resurfaced patellar components, have not been well described. In contrast, sagittal plane alignment and component rotation have been more thoroughly studied and do influence patellofemoral tracking (18, 19). Further research exploring patellofemoral tracking with respect to the coronal plane alignment would be of value.

Our study included 25 radiographs and four observers; despite the benefit of including multiple observers on reproducibility, an analysis of more radiographs by more users would add to the power analysis of the calculator. Moreover, the range of radiographs did not include many knees with severe coronal plane deformity (greater than 7 degrees). Testing the calculator in significant deformity would explore its limitations in these patients.

Our study used actual-size radiographs to obtain calculations, which maximises image resolution. Currently, there is no minimum radiograph size that will be refused by the CPAK calculator. It would be useful to look at radiographs of differing resolution to study this. And finally, the CPAK calculator currently only exists in English, limiting its use to surgeons fluent in that language. Future version would benefit from validation in other languages.

Conclusion

This study has validated the accuracy of the CPAK on-line calculator. High levels of agreement were observed amongst all observers. Level of surgical experience did not influence the agreement amongst observers.

REFERENCES

1. Holme T J, Henckel J, Hartshorn K, Cobb J P, Hart A J. Computed tomography scanogram compared to long leg radiograph for determining axial knee alignment. Acta orthopaedica. 2015; 86(4):440-3.
2. Boonen B, Kerens B, Schotanus M G, Emans P, Jong B, Kort N P. Inter-observer reliability of measurements performed on digital long-leg standing radiographs and assessment of validity compared to 3D C T-scan. The Knee. 2016; 23(1):20-4.
3. Zhang Y Z, Lu S, Zhang H Q, Jin Z M, Zhao J M, Huang J, et al. Alignment of the lower extremity mechanical axis by computer-aided design and application in total knee arthroplasty. International journal of computer assisted radiology and surgery. 2016; 11(10):1881-90.
4. Babazadeh S, Dowsey M M, Bingham R J, Ek E T, Stoney J D, Choong P F. The long leg radiograph is a reliable method of assessing alignment when compared to computer-assisted navigation and computer tomography. The Knee. 2013; 20(4):242-9.
5. Bowman A, Shunmugam M, Watts A R, Bramwell D C, Wilson C, Krishnan J. Inter-observer and intra-observer reliability of mechanical axis alignment before and after total knee arthroplasty using long leg radiographs. The Knee. 2016; 23(2):203-8.
6. Insall J, Scott W N, Ranawat C S. The total condylar knee prosthesis. A report of two hundred and twenty cases. The Journal of bone and joint surgery American volume. 1979; 61(2):173-80.
7. Park A, Stambough J B, Nunley R M, Barrack R L, Nam D. The Inadequacy of Short Knee Radiographs in Evaluating Coronal Alignment After Total Knee Arthroplasty. The Journal of arthroplasty. 2016; 31(4):878-82.
8. Bellemans J, Colyn W, Vandenneucker H, Victor J. The Chitranjan Ranawat award: is neutral mechanical alignment normal for all patients? The concept of constitutional varus. Clinical orthopaedics and related research. 2012; 470(1):45-53.
9. Raju P K, Kini S G, Verma A. Wear patterns of tibiofemoral articulation in osteoarthritic knees: analysis and review of literature. Archives of orthopaedic and trauma surgery. 2012; 132(9):1267-71.
10. Abdel M P, Oussedik S, Parratte S, Lustig S, Haddad F S. Coronal alignment in total knee replacement: historical review, contemporary analysis, and future direction. The bone & joint journal. 2014; 96-b(7):857-62.
11. Thienpont E, Schwab P E, Fennema P. A systematic review and meta-analysis of patient-specific instrumentation for improving alignment of the components in total knee replacement. The bone & joint journal. 2014; 96-b (8):1052-61.
12. Jeffery R S, Morris R W, Denham R A. Coronal alignment after total knee replacement. The Journal of bone and joint surgery British volume. 1991; 73(5):709-14.
13. D'Lima D D, Chen P C, Colwell C W, Jr. Polyethylene contact stresses, articular congruity, and knee alignment. Clinical orthopaedics and related research. 2001(392): 232-8.
14. Werner F W, Ayers D C, Maletsky L P, Rullkoetter P J. The effect of valgus/varus malalignment on load distribution in total knee replacements. Journal of biomechanics 2005; 38(2):349-55.
15. Li Z, Esposito C I, Koch C N, Lee Y Y, Padgett D E, Wright T M. Polyethylene Damage Increases With Varus Implant Alignment in Posterior-stabilized and Constrained Condylar Knee Arthroplasty. Clinical orthopaedics and related research. 2017; 475(12):2981-91.
16. Shelton T J, Nedopil A J, Howell S M, Hull M L. Do varus or valgus outliers have higher forces in the medial or lateral compartments than those which are in-range after a kinematically aligned total knee arthroplasty? limb and joint line alignment after kinematically aligned total knee arthroplasty. The bone & joint journal. 2017; 99-b (10):1319-28.
17. Slevin O, Schmid F A, Schiapparelli F F, Rasch H, Amsler F, Hirschmann M T. Coronal femoral TKA position significantly influences in vivo patellar loading in unresurfaced patellae after primary total knee arthroplasty. Knee surgery, sports traumatology, arthroscopy: official journal of the ESSKA. 2017; 25(11):3605-10.
18. Keshmiri A, Maderbacher G, Baier C, Sendtner E, Schaumburger J, Zeman F, et al. The influence of component alignment on patellar kinematics in total knee arthroplasty. Acta orthopaedica. 2015; 86(4):444-50.
19. Mannan A, Smith T O. Favourable rotational alignment outcomes in PSI knee arthroplasty: A Level 1 systematic review and meta-analysis. The Knee. 2016; 23(2):186-90.

The invention claimed is:

1. A computer-implemented method for planning a total knee replacement surgical procedure on a knee of a leg of a patient comprising:
   obtaining by a processor anatomical data for the leg of the patient via analysis of one or more digital representations of the leg;
   calculating by the processor a lateral distal femoral angle (LDFA) and a medial proximal tibial angle (MPTA) from the anatomical data;
   determining by the processor an arithmetic hip-knee-ankle angle (aHKA) from the LDFA and the MPTA;
   setting a proximal tibial resection plane angle;
   determining by the processor a distal femoral resection plane angle from the proximal tibial resection plane angle and the aHKA, wherein the distal femoral resection plane angle is determined such that a resulting hip-knee-ankle angle (HKA) is equal to the aHKA;
   generating by the processor a surgical plan including the proximal tibial resection plane angle and the distal femoral resection plane angle;
   outputting via a user interface the surgical plan and the resulting hip-knee-ankle angle (HKA), and
   resecting a portion of a tibia based at least partly on the proximal tibial resection plane angle,
   wherein the surgical plan on the user interface is configured for interactive adjustments and visualization of the proximal tibial resection plane angle and the distal femoral resection plane angle.

2. The method of claim 1, wherein the anatomical data is obtained using at least one x-ray image.

3. The method of claim 2, wherein the at least one x-ray image is a long leg x-ray.

4. The method of claim 3, wherein the long leg x-ray includes at least a portion of a pelvis and ankles bones and an entire femur and tibia bone of the patient.

5. The method of claim 3, wherein the at least one x-ray image is of a frontal plane of the patient.

6. The method of claim 1, wherein the step of determining the LDFA includes determining a femoral mechanical axis and a femoral joint line from the anatomical data.

7. The method of claim 6, wherein the step of determining the LDFA further includes the step of determining a lateral angle between the femoral mechanical axis and the femoral joint line.

8. The method of claim 1, wherein the step of determining the MPTA includes determining a tibial mechanical axis and a tibial joint line from the anatomical data.

9. The method of claim 8, wherein step of determining the MPTA further includes the step of determining a medial angle between the tibial mechanical axis and the tibial joint line.

10. The method of claim 1, wherein the step of determining the aHKA includes the step of calculating a difference between the LDFA and the MPTA.

11. The method of claim 1, wherein the proximal tibial resection plane angle and the distal femoral resection plane angle are defined in a coronal plane.

12. The method of claim 1, further including the step of comparing the determined distal femoral resection plane angle to a preset range of distal femoral resection plane angles and changing the distal femoral resection plane angle if the distal femoral resection plane angle is outside the preset range.

13. The method of claim 1, further including the step of classifying an alignment of the patient's knee as:
 (a) valgus if the aHKA is positive;
 (b) varus if the aHKA is negative; or
 (c) neutral if the aHKA is substantially zero.

14. The method of claim 13, further including the step of computing a joint line obliquity value, wherein the joint line obliquity value is equal to a sum of LDFA and the MPTA.

15. The method of claim 14, further including the step of classifying the alignment of the patient's knee as:
 (a) an apex distal joint line if the joint line obliquity value is less than 180°;
 (b) an apex proximal joint line if the joint line obliquity value is greater than 180°; or
 (c) a neutral joint line if the joint line obliquity is substantially equal to 180°.

16. The method of claim 1, wherein a distal femoral resection plane corresponding to the distal femoral resection plane angle and a proximal tibial resection plane corresponding to the proximal tibial resection plane angle are parallel.

17. The method of claim 1, further including a step of selecting anatomical landmarks on the one or more digital representations of the legs, the selected anatomical landmarks being used by the processor to calculate LDFA and the MPTA.

18. A computer-implemented method for planning a total knee replacement surgical procedure on a knee of a leg of a patient comprising:
 obtaining by a processor anatomical data for the leg of the patient via analysis of one or more digital representations of the leg;
 selecting one or more anatomical landmarks on the one or more digital representations of the leg,
 calculating by the processor a lateral distal femoral angle (LDFA) and a medial proximal tibial angle (MPTA) from the anatomical data and the selected anatomical landmarks;
 determining by the processor an arithmetic hip-knee-ankle angle (aHKA) from the LDFA and the MPTA;
 setting a distal femoral resection plane angle;
 determining by the processor a proximal tibial resection plane angle from the distal femoral resection plane angle and the aHKA,
 wherein the proximal tibial resection plane angle is determined such that a resulting hip-knee-ankle angle (HKA) is equal to the aHKA,
 generating by the processor a surgical plan including the proximal tibial resection plane angle and the distal femoral resection plane angle;
 resecting a portion of a femur based at least partly on the femoral resection plane angle, and
 outputting via a user interface the surgical plan and the resulting hip-knee-ankle angle (HKA), wherein the surgical plan on the user interface is configured for interactive adjustment and visualization of the proximal tibial resection plane angle and the distal femoral resection plane angle.

19. The method of claim 18, wherein the anatomical data is obtained from at least one x-ray image of a frontal plane of the patient.

20. The method of claim 18, wherein the step of determining the aHKA includes the step of calculating a difference between the LDFA and the MPTA.

21. The method of claim 18, wherein the proximal tibial resection plane angle and the distal femoral resection plane angle are defined in a coronal plane.

22. The method of claim 18, wherein a distal femoral resection plane corresponding to the distal femoral resection plane angle and a proximal tibial resection plane corresponding to the proximal tibial resection plane angle are parallel.

* * * * *